(12) United States Patent
Gunji et al.

(10) Patent No.: US 8,017,363 B2
(45) Date of Patent: Sep. 13, 2011

(54) METHOD FOR PRODUCTION OF L-LYSINE USING METHANOL-UTILIZING BACTERIUM

(75) Inventors: Yoshiya Gunji, Kawasaki (JP); Hisashi Yasueda, Kawasaki (JP); Reiko Hirai, Kawasaki (JP); Seiko Hirano, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 505 days.

(21) Appl. No.: 12/184,598

(22) Filed: Aug. 1, 2008

(65) Prior Publication Data

US 2010/0190216 A1 Jul. 29, 2010

Related U.S. Application Data

(63) Continuation of application No. PCT/JP2007/051796, filed on Feb. 2, 2007.

(30) Foreign Application Priority Data

Feb. 2, 2006 (JP) .................................. 2006-025617

(51) Int. Cl.
*C12P 13/08* (2006.01)
(52) U.S. Cl. ..................................... 435/115; 435/252.3
(58) Field of Classification Search .................. 435/115, 435/252.3
See application file for complete search history.

(56) References Cited

U.S. PATENT DOCUMENTS

| | | | |
|---|---|---|---|
| 6,040,160 A | 3/2000 | Kojima et al. |
| 6,858,406 B1 | 2/2005 | Vrlijc et al. |
| 6,878,533 B2 | 4/2005 | Tsujimoto et al. |
| 6,911,332 B2 | 6/2005 | Usuda et al. |
| 7,026,149 B2 | 4/2006 | Usuda et al. |
| 7,029,893 B2 | 4/2006 | Usuda et al. |
| 7,060,475 B2 | 6/2006 | Usuda et al. |
| 7,160,704 B2 | 1/2007 | Takeshita et al. |
| 7,163,810 B2 | 1/2007 | Yasueda et al. |
| 7,169,587 B2 | 1/2007 | Gunji et al. |
| 7,192,747 B2 | 3/2007 | Ono et al. |
| 7,192,748 B2 | 3/2007 | Usuda et al. |
| 7,205,132 B2 | 4/2007 | Hirano et al. |
| 7,211,416 B2 | 5/2007 | Asahara et al. |
| 7,211,421 B2 | 5/2007 | Tsujimoto et al. |
| 7,217,543 B2 | 5/2007 | Gunji et al. |
| 7,220,570 B2 | 5/2007 | Usuda et al. |
| 7,223,572 B1 | 5/2007 | Gunji et al. |
| 7,335,506 B2 | 2/2008 | Gunji et al. |
| 2002/0061578 A1 | 5/2002 | Kato et al. |
| 2003/0049805 A1 | 3/2003 | Nagase et al. |
| 2003/0054506 A1 | 3/2003 | Otsuna et al. |
| 2003/0124687 A1 | 7/2003 | Gunji et al. |
| 2003/0232338 A1 | 12/2003 | Usuda et al. |
| 2004/0091891 A1 | 5/2004 | Iomantas et al. |
| 2004/0146974 A1 | 7/2004 | Gunji et al. |
| 2004/0166570 A1 | 8/2004 | Asahara et al. |
| 2005/0003495 A1 | 1/2005 | Gunji et al. |
| 2005/0176121 A1 | 8/2005 | Takeshita et al. |
| 2006/0019355 A1 | 1/2006 | Ueda et al. |
| 2006/0019356 A1 | 1/2006 | Usuda et al. |
| 2006/0030010 A1 | 2/2006 | Usuda et al. |
| 2006/0030011 A1 | 2/2006 | Usuda et al. |
| 2006/0040365 A1 | 2/2006 | Kozlov et al. |
| 2006/0141588 A1 | 6/2006 | Nakamura et al. |
| 2007/0172932 A1 | 7/2007 | Hirano et al. |
| 2007/0249017 A1 | 10/2007 | Usuda et al. |
| 2008/0038825 A1 | 2/2008 | Gunji et al. |

FOREIGN PATENT DOCUMENTS

| | | |
|---|---|---|
| EP | 1253195 A1 | 10/2002 |
| EP | 1266966 | 12/2002 |
| EP | 2006391 | 12/2008 |
| WO | WO00/61723 | 10/2000 |
| WO | WO 2006/059715 A1 | 6/2006 |

OTHER PUBLICATIONS

Bouvier, J., et al., "Nucleotide Sequence and Expression of the *Escherichia coli dapB* Gene," J. Biol. Chem. 1984;259(23):14829-14834.

Gunji, Y., et al., "Characterization of the L-Lysine Biosynthetic Pathway in the Obligate Methylotroph *Methylophilus methylotrophus*," Biosci. Biotechnol. Biochem. 2004;68(7):1449-1460.

Gunji, Y., et al., "Enhancement of L-Lysine Production in Methylotroph *Methylophilus methylotrophus* by Introducing a Mutant LysE Exporter," J. Biotechnol. 2006;127:1-13.

Haziza, C., et al., "Nucleotide Sequence of the asd Gene of *Escherichia coli*: Absence of a Typical Attenuation Signal," The EMBO Journal 1982;1(3):379-384.

Ishino, S., et al., "Nucleotide Sequence of the Meso-Diaminopimelate D-Dehydrogenase Gene from *Corynebacterium glutamicum*," Nuc. Acids. Res. 1987;15(9):3917.

Tsujimoto, N., et al., "L-Lysine Biosynthetic Pathway of *Methylophilus methylotrophus* and Construction of an L-Lysine Producer," J. Biotechnol. 2006;124:327-337.

International Search Report for PCT Patent App. No. PCT/JP2007/051796 (Mar. 6, 2007).

Bellmann, A., et al., "Expression Control and Specificity of the Basic Amino Acid Exporter LysE of *Corynebacterium glutamicum*," Microbiology (2001);147:1765-1774.

Eggeling L., et al., "Improved L-Lysine Yield with *Corynebacterium glutamicum* : Use of *dapA* Resulting in Increased Flux Combined with Growth Limitation," Appl Microbial Biotechnol(1998);49:24-30.

(Continued)

*Primary Examiner* — Tekchand Saidha
(74) *Attorney, Agent, or Firm* — Shelly Guest Cermak; Cermak Nakajima LLP

(57) ABSTRACT

A method for production of L-lysine is provided which includes the steps of cultivating a methanol-utilizing bacterium in a culture medium to produce and accumulate L-lysine in the culture medium and collecting the L-lysine from the culture medium, wherein the methanol-utilizing bacterium contains DNA encoding dihydrodipicolinate synthetase which is desensitized to feedback inhibition by L-lysine and DNA encoding a LysE protein that can enhance the excretion of L-lysine out of the methanol-utilizing bacterium, and the bacterium is modified so as to increase the intracellular activities of diaminopimelic acid dehydrogenase, diaminopimelic acid decarboxylase, dihydrodipicolinic acid reductase and aspartate-semialdehyde dehydrogenase.

17 Claims, 5 Drawing Sheets

OTHER PUBLICATIONS

Motoyama H., et al., "Overproduction of L-Lysine from Methanol by *Methylobacillus glycogenes* Derivatives Carrying a Plasmid with a Mutated *dapA* Gene," Applied and Environmental Microbiology, Jul. 2001,vol. 67,No. 7,p. 3064-3070.

Ishikawa K., et al., "Disruption of *metF* Increased L-Lysine Production by *Methylophilus methylotrophus* from Methanol," Biosci. Biotechnol. Biochem., 2008;72(5):1317-1324.

Presentation slides and speech by Yoshiya Gunji at the Annual Meeting of the Society for Biotechnology, Japan, held at Meijyou University on Sep. 23, 2004 in Japanese and the English translation.

International Preliminary Report on Patentability for PCT Patent App. No. PCT/JP2007/051796 (Aug. 14, 2008).

Supplementary European Search Report for EP Patent App. No. 07713790.9 (Feb. 16, 2010).

METHOD FOR PRODUCTION OF L-LYSINE USING METHANOL-UTILIZING BACTERIUM

This application is a continuation under 35 U.S.C. §120 to PCT Patent Application No. PCT/JP2007/051796, filed on Feb. 2, 2007, which claims priority under 35 U.S.C. §119 to Japanese Patent Application No. 2006-025617, filed Feb. 2, 2006, both of which are incorporated by reference. The Sequence Listing in electronic format filed herewith is also hereby incorporated by reference in its entirety (File Name: US-368_Seq_List_Copy_1; File Size: 74 KB; Date Created: Aug. 1, 2008).

BACKGROUND OF THE INVENTION

1. Field of the Invention

The present invention relates to microbial industries. More specifically, the present invention relates to a method of producing L-lysine by fermentation, and a microorganism used for the production method.

2. Brief Description of the Related Art

L-amino acids such as L-lysine, L-glutamic acid, L-threonine, L-leucine, L-isoleucine, L-valine, and L-phenylalanine are industrially produced by fermentation using microorganisms that belong to the genus *Brevibacterium, Corynebacterium, Bacillus, Escherichia, Streptomyces, Pseudomonas, Arthrobacter, Serratia, Penicillium, Candida* or the like. Strains isolated from nature, or artificial mutants thereof, have been used to improve the productivity of these microorganisms. Moreover, various technologies have been disclosed to increase the ability to produce L-amino acids, such as using recombinant DNA technology to enhance L-amino acid biosynthetic enzyme activity.

As for bacteria belonging to the genus *Escherichia*, for example, a method of producing L-lysine by using a strain in which dihydrodipicolinate synthase activity is enhanced has been disclosed (JP 56-018596 A and U.S. Pat. No. 4,346,170).

Furthermore, a method of producing L-lysine is disclosed in WO 95/16042 (U.S. Pat. No. 6,040,160), wherein a strain is transformed with a plasmid containing the following: a DNA encoding *Escherichia* dihydrodipicolinate synthase having a mutation to desensitize feedback inhibition by L-lysine, a DNA encoding aspartokinase that is desensitized to feedback inhibition by L-lysine, a DNA encoding dihydrodipicolinate reductase, and a DNA encoding diaminopimelate dehydrogenase derived from a coryneform bacterium.

Furthermore, production of L-lysine has been reported to be improved by enhancing an activity of aspartate-semialdehyde dehydrogenase or phosphoenolpyruvate carboxylase, and activities of nicotinamide adenine dinucleotide transhydrogenase or aspartase in an *Escherichia* bacterium having a DNA encoding a *Escherichia* dihydrodipicolinate synthase that has a mutation desensitizing feedback inhibition to L-lysine, a DNA encoding an aspartokinase which is desensitized to feedback inhibition to L-lysine, a DNA encoding a dihydrodipicolinate reductase, and a DNA encoding a diaminopimelate dehydrogenase derived from a coryneform bacterium (WO 01/53459 (EP 1,253,195 A)).

As for coryneform bacteria, WO 95/11985 (U.S. Pat. No. 5,830,716) discloses that L-lysine productivity can be improved by increasing the intracellular activity of nicotinamide dinucleotide transhydrogenase.

Furthermore, a method of producing L-lysine using a strain in which phosphoenolpyruvate carboxylase activity is enhanced and a method of producing L-lysine using a strain in which aspartate-semialdehyde dehydrogenase activity is enhanced are disclosed in JP 60-87788 A and JP 06-102028 B, respectively.

It has also been reported that by introducing a dihydrodipicolinate synthase gene in addition to a mutant aspartokinase gene which is desensitized to feedback inhibition, L-lysine productivity can be improved (Applied and Environmental Microboiology 57(6), 1746-1752 (1991)).

Moreover, a method of significantly improving the yield of L-lysine without suppressing growth by introducing into a coryneform bacterium a plurality of L-lysine biosynthetic genes, specifically, mutant aspartokinase, dihydrodipicolinate reductase, dihydrodipicolinate synthase, diaminopimelate decarboxylase, and diaminopimelate dehydrogenase in combination, has also been disclosed (WO 96/40934 (EP 841,395, US 2003-0054506A)).

Also, in recent years, the LysE protein and gene encoding it were discovered. The LysE protein functions to export L-lysine specifically to the outside of a microorganism. Also, it has been reported that by increasing the LysE gene in a cell, the L-lysine-producing ability of the cell is also increased (Molecular Microbiology 22:815-826 (1996) or WO 97/23597 (U.S. Pat. No. 6,858,406)).

It has also been reported that the production of some L-amino acids can be improved by increasing the expression of the proteins responsible for amino acid export in *Escherichia coli* (JP 2000-189180 A (EP 1,016,710 A)). For example, it has been reported that production of cystine, cysteine, and the like can be improved by enhancing the expression of the ORF306 gene in *Escherichia coli* (EP 885,962 B).

Production of L-amino acids has been considerably increased by breeding of microorganisms and improving production methods as mentioned above. However, in order to respond to further increases in demand in the future, development of more efficient and less expensive methods is still desirable.

Methanol is known to be a raw material for fermentation and is available in large quantities at a low cost. Methods of producing L-amino acids by fermentation using methanol are known, and include those using microorganisms that belong to the genus *Achromobacter* or *Pseudomonas* (JP 45-25273 A), *Protaminobacter* (JP 49-125590 B), *Protaminobacter* or *Methanomonas* (JP 50-25790 A), *Microcyclus* (JP 52-18886 A), *Methylobacillus* (JP 04-91793 A), *Bacillus* (JP 03-505284 A), and the like.

Methods of producing L-amino acids by breeding bacteria belonging to the genus *Methylophilus* using artificial mutagenesis and recombinant DNA technology have been developed, resulting in enhancing the activities of dihydrodipicolinate synthase and aspartokinase (WO 00/61723 (EP 1,188,822 A, U.S. Pat. No. 7,223,572)). It was recognized that a big hurdle in the amino acid production by fermentation of methanol using a methanol-assimilating bacterium is the amino acid export process. In order to solve the problems, a mutant was developed with L-lysine-exporting activity in a methanol-assimilating bacterium from a LysE protein that is isolated from a bacterium belonging to the genus *Corynebacterium* and involved in export of L-lysine. It was shown that L-lysine can be efficiently produced by: breeding bacteria belonging to the genus *Methylophilus* using artificial mutagenesis, a recombinant DNA technology, and a modified L-lysine exporter, and the inventors have developed a method of producing an L-amino acid using a bacterium belonging to the genus *Methylophilus* (WO 00/61723 (EP 1,188,822 A, U.S. Pat. No. 7,223,572) or JP 2004-166594 A (US 2005-003495 A)).

However, for the production of L-amino acids by fermentation of methanol using a methanol-assimilating bacterium, there has been no report of significant improvements in L-lysine yield by enhancing expression of an L-lysine export gene in combination with a plurality of L-lysine biosynthetic genes.

It is known that enhancement of either ddh or lysA in a coryneform bacterium can improve the amount of produced Lys. It has also been disclosed that enhancement of ddh and lysA in combination can improve the Lys production rate and the amount of produced Lys.

However, enhancing either of these genes in a bacterium belonging to the genus *Methylophilus* is not known to increase, and may slightly decrease the amount of L-lysine that is produced.

SUMMARY OF THE INVENTION

It is an aspect of the present invention to provide a method of efficiently producing L-lysine using methanol. Methanol is abundantly and inexpensively available.

A remarkable improvement in L-lysine yield is reported herein, essentially by enhancing a gene encoding an L-lysine exporter in combination with a plurality of L-lysine biosynthetic genes. That is, L-lysine yield is improved by enhancing expression of the diaminopimelate decarboxylase gene and the diaminopimelate dehydrogenase gene in addition to a DNA encoding a mutant LysE protein and a DNA encoding dihydrodipicolinate synthase which is desensitized to feedback inhibition by L-lysine in a bacterium belonging to the genus *Methylophilus*, which was never achieved by enhancing expression of only one of the genes. Moreover, the L-lysine-producing ability of a bacterium belonging to the genus *Methylophilus* is further improved by enhancing expression of the dihydrodipicolinate reductase gene and the aspartate-semialdehyde dehydrogenase gene in addition to the above-mentioned genes, and L-lysine production is significantly improved by enhancing expression of the aspartokinase gene.

A very stable strain was constructed by enhancing the expression of the biosynthetic genes with a plasmid and incorporating multiple copies of the genes into the chromosome of a methanol-assimilating bacterium. Gene expression can be further enhanced using a plasmid in combination, to thereby obtain a methanol-assimilating bacterium having a significantly improved L-lysine yield.

That is, the present invention provides the following.

It is an aspect of the present invention to provide a methanol-assimilating bacterium comprising:

a DNA encoding dihydrodipicolinate synthase which is desensitized to feedback inhibition by L-lysine; and a DNA encoding a LysE protein that has been mutated to promote the export of L-lysine to the outside of said bacterium, wherein said bacterium is modified to enhance intracellular activities of the following enzymes: diaminopimelate dehydrogenase, diaminopimelate decarboxylase, dihydrodipicolinate reductase, and aspartate-semialdehyde dehydrogenase.

It is a further aspect of the present invention to provide the methanol-assimilating bacterium as described above, further comprising:

a DNA encoding aspartokinase which is desensitized to feedback inhibition by L-lysine.

It is a further aspect of the present invention to provide the methanol-assimilating bacterium as described above, wherein DNAs encoding the enzymes or the LysE protein introduced into said bacterium by a method selected from the group consisting of:

i) introducing said DNA into the chromosomal DNA, and ii) transforming the bacterium with a plasmid(s) comprising said DNAs, and iii) combinations thereof.

It is a further aspect of the present invention to provide the methanol-assimilating bacterium as described above, wherein the DNA encoding dihydrodipicolinate synthase, the DNA encoding dihydrodipicolinate reductase, the DNA encoding aspartate-semialdehyde dehydrogenase, and the DNA encoding aspartokinase are all from, or are native to, a bacterium belonging to the genus *Escherichia*, the DNA encoding diaminopimelate decarboxylase is from, or native to, a bacterium belonging to the genus *Methylophilus*, and the DNA encoding diaminopimelate dehydrogenase and the DNA encoding the mutant LysE are from, or native to, a bacterium belonging to the genus *Brevibacterium*.

It is a further aspect of the present invention to provide the methanol-assimilating bacterium as described above, wherein said bacterium belongs to the genus *Methylophilus*.

It is a further aspect of the present invention to provide the methanol-assimilating bacterium as described above, wherein said bacterium is *Methylophilus methylotrophus* AJ110196 (FERM BP-10434).

It is a further aspect of the present invention to provide a method of producing L-lysine comprising culturing the methanol-assimilating bacterium as described above in a medium; and collecting L-lysine from the medium or the bacterium.

It is a further aspect of the present invention to provide the method of producing L-lysine as described above, wherein the main carbon source in the medium is carbon.

It is a further aspect of the present invention to provide *Methylophilus methylotrophus* AJ110196 (FERM BP-10434).

DESCRIPTION OF THE PREFERRED EMBODIMENTS

Figure 1:
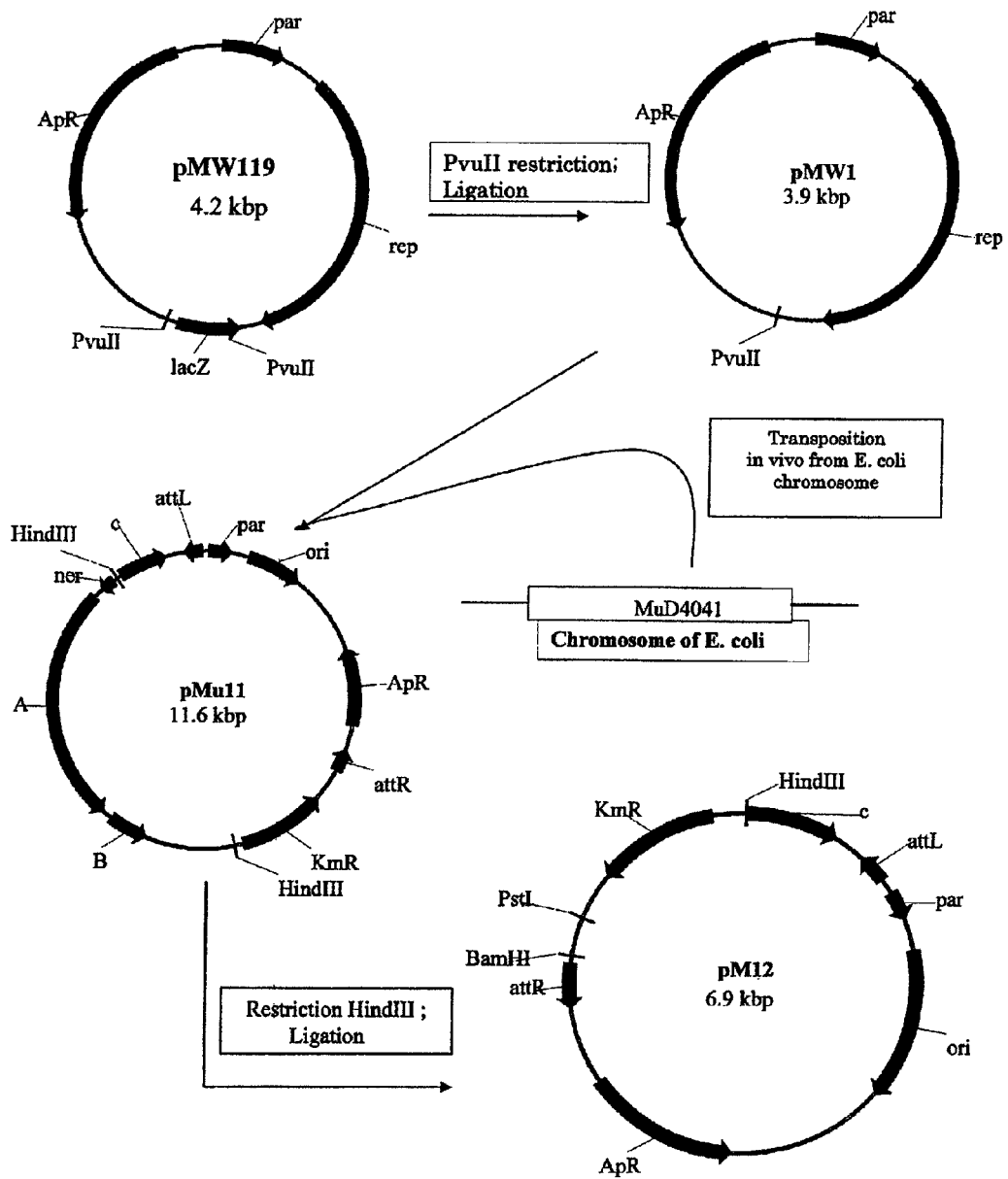
FIG. 1 is an illustration showing the construction of plasmid pM12.

Hereinafter, the present invention will be described in detail.

The present invention provides a methanol-assimilating bacterium which carries a DNA encoding dihydrodipicolinate synthase that is desensitized to feedback inhibition by L-lysine, and a DNA encoding a mutant LysE that promotes the export of L-lysine to the outside of the bacterium when the DNA is introduced into the methanol-assimilating bacterium. Furthermore, the bacterium has been further modified to enhance the intracellular activities of diaminopimelate dehydrogenase, diaminopimelate decarboxylase, dihydrodipicolinate reductase, and aspartate-semialdehyde dehydrogenase.

The methanol-assimilating bacterium can grow in a medium containing methanol as the main carbon source, and may be a member of the genus *Methylophilus* and the like. Specific examples include *Methylophilus* bacteria such as *Methylophilus methylotrophus*. Examples of *Methylophilus methylotrophus* include the AS1 strain (NCIMB10515). *Methylophilus methylotrophus* AS1 strain (NCIMB10515) is available from the National Collections of Industrial and Marine Bacteria (Address: NCIMB Lts., Tony Research Station 135, Abbey Road, Aberdeen AB9 8DG, United Kingdom).

DNA encoding dihydrodipicolinate synthase which is desensitized to feedback inhibition by L-lysine The DNA encoding dihydrodipicolinate synthase which is desensitized to feedback inhibition by L-lysine (hereinafter, also referred to as the dapA* gene) is not particularly limited, however, it is preferably, for example, a DNA encoding a dihydrodipicolinate synthase derived from, or native to, a bacterium belonging to the genus *Escherichia* and having a mutation to desensitize to feedback inhibition by L-lysine.

Examples of the DNA encoding wild-type dihydrodipicolinate synthase derived from a bacterium belonging to the genus *Escherichia* include a DNA encoding the amino acid sequence of SEQ ID NO: 41. Examples of the mutation to desensitize the feedback inhibition by L-lysine include a mutation that replaces the histidine residue at position 118 in the amino acid sequence of SEQ ID NO: 41 with a tyrosine residue (H118Y mutation). Therefore, examples of the dapA* gene include a DNA encoding the amino acid sequence of SEQ ID NO: 41 in which the histidine residue at position 118 is replaced with a tyrosine residue.

The dapA* gene may be a DNA encoding a protein having at least 80%, preferably at least 90%, more preferably at least 95%, particularly preferably at least 98% homology to the entire amino acid sequence of SEQ ID NO: 41, having the H118Y mutation, and having dihydrodipicolinate synthase activity.

Moreover, the dapA* gene may be a DNA encoding a protein having the amino acid sequence of SEQ ID NO: 41, but which includes substitution, deletion, insertion, addition, or the like of one or several amino acids so long as the protein has the H118Y mutation and the dihydrodipicolinate synthase activity is not impaired.

Although the number of amino acids which constitutes "several" may differ depending on their relative positions in the three-dimensional structure of the protein, or the types of amino acid residues being altered, it is specifically 1 to 20, preferably 1 to 10, and more preferably 1 to 5. The above-mentioned substitution of amino acids is preferably a conservative substitution. Examples of conservative substitutions include: substitution of ser or thr for ala; substitution of gln, his, or lys for arg; substitution of glu, gln, lys, his, or asp for asn; substitution of asn, glu, or gln for asp; substitution of ser or ala for cys; substitution of asn, glu, lys, his, asp, or arg for gln; substitution of gly, asn, gln, lys, or asp for glu; substitution of pro for gly; substitution of asn, lys, gln, arg, or tyr for his; substitution of leu, met, val, or phe for ile; substitution of ile, met, val, or phe for leu; substitution of asn, glu, gln, his, or arg for lys; substitution of ile, leu, val or phe for met; substitution of trp, tyr, met, ile, or leu for phe; substitution of thr or ala for ser; substitution of ser or ala for thr; substitution of phe or tyr for trp; substitution of his, phe, or trp for tyr; and substitution of met, ile, or leu for val. The above-mentioned amino acid substitutions, deletions, insertions, additions, inversions, or the like may be the result of a naturally-occurring mutation (mutant or variant) due to an individual difference, or a difference of bacterial species harboring the dihydrodipicolinate synthase gene.

The dapA* gene may be a DNA which is able to hybridize with a complementary strand of the nucleotide sequence of SEQ ID NO: 40 or a probe that can be prepared from the sequence under stringent conditions so long as the gene encodes a protein having the H118Y mutation and having dihydrodipicolinate synthase activity. The term "stringent conditions" refers to conditions where a so-called specific hybrid is formed and a non-specific hybrid is not formed. It is difficult to clearly define the conditions with a numerical value, but examples thereof include conditions corresponding to a salt concentration and temperature of washing which are typical for a standard Southern hybridization, e.g., washing at 60° C. with 1×SSC and 0.1% SDS, preferably at 60° C. with 0.1×SSC and 0.1% SDS, and more preferably at 68° C. with 0.1×SSC and 0.1% SDS, once or preferably twice or three times.

The dapA* gene may be obtained by site-specific mutagenesis, or from the RSFD80 plasmid as described below.

It is known that the wild-type dihydrodipicolinate synthase derived from coryneform bacteria is not subject to feedback inhibition by L-lysine (J Gen Microbiol. 1988 December; 134 (12):3221-9.). Therefore, it is not always necessary to use a DNA encoding a dihydrodipicolinate synthase which is desensitized to feedback inhibition by L-lysine.

DNA encoding mutant LysE that promotes export of L-lysine to the outside of the bacterium when the DNA is introduced into methanol-assimilating bacterium Examples of the DNA encoding mutant LysE that promotes export of L-lysine to the outside of a bacterium when the DNA is introduced into a methanol-assimilating bacterium include the LysE24 gene (US 2003-0124687), lysE56 gene (US 2004-0146974), and lysE24 m5 (WO 2006/059715).

The expression "promoting export of L-lysine to the outside of a bacterium" means that when a methanol-assimilating bacterium containing the DNA is cultured in a medium, the amount of L-lysine exported into the medium increases as compared with the methanol-assimilating bacterium not containing the DNA. An increase in the export of the L-lysine to the outside of the cell occurs when there is an increase in L-lysine accumulation in the medium during the culture of the methanol-assimilating bacterium containing the DNA as compared with the accumulation when the methanol-assimilating bacterium not containing the DNA is cultured.

The DNA encoding mutant LysE that promotes export of L-lysine to the outside of a bacterium when the DNA is introduced into the methanol-assimilating bacterium is preferably, but is not limited to, a DNA encoding the LysE protein derived from a bacterium belonging to the genus *Brevibacterium* and having a mutation for promoting export of L-lysine to the outside of a bacterium when the DNA is introduced into the methanol-assimilating bacterium, and examples thereof include the LysE24 gene (US 2003-0124687), lysE56 gene (US 2004-0146974), and lysE24 m5 (WO 2006/059715).

(1) lysE24 Gene

The lysE24 gene is a DNA encoding a mutant of a protein having a loop region and six hydrophobic helixes that is involved in the export of L-lysine to the outside of a bacterium (wild-type lysE protein: SEQ ID NO: 55), wherein the mutant lysE protein does not have the above-mentioned loop region and promotes export of L-lysine, L-arginine, or both to the outside of a bacterium when the DNA is introduced into the methanol-assimilating bacterium. Examples of the LysE24 gene include the LysE24 gene described in JP 2004-166594 A (US 2005-003495).

An example includes a DNA encoding the protein of SEQ ID NO: 51. In addition, the protein may be a protein having not less than 80%, preferably not less than 90%, more preferably not less than 95%, particularly preferably not less than 98% homology to the entire amino acid sequence of SEQ ID NO: 51 so long as the gene can promote export of L-lysine to the outside of a bacterium when it is introduced into a methanol-assimilating bacterium.

Moreover, the gene may be a DNA encoding a protein having the sequence of SEQ ID NO: 51, but which includes substitutions, deletions, insertions, additions, or the like of one or several amino acids so long as the activity for promoting export of L-lysine to the outside of a cell is not impaired.

Moreover, the lysE24 gene may be a DNA which is able to hybridize with a complementary strand of the nucleotide sequence of SEQ ID NO: 50 or a probe that can be prepared from the nucleotide sequence under stringent conditions so long as the gene encodes a protein having the activity for promoting export of L-lysine to the outside of a cell.

The definitions of the terms "several" and "stringent conditions" and preferable amino acid substitutions are the same as described above.

The lysE24 gene can be obtained from, for example, the plasmid pRSlysE24 described in JP 2004-166594 A (US 2005-003495). E. coli JM109 strain transformed with pRSlysE24 was designated as AJ13830, and deposited at National Institute of Advanced Industrial Science and Technology, International Patent Organism Depository on Jun. 4, 2001 and given an accession number of FERM P-18369. Then, the deposit was converted to an international deposit under the provisions of the Budapest Treaty on May 13, 2002, and given the accession number FERM BP-8040.

(2) lysE56 Gene

An example of the lysE56 gene includes a gene encoding a protein having the amino acid sequence of SEQ ID NO: 55 in which at least the glycine residue at position 56 is replaced with another amino acid residue (US 2004-0146974). The gene may also encode a protein having the amino acid sequence of SEQ ID NO: 55 having not less than 80%, preferably not less than 90%, more preferably not less than 95%, particularly preferably not less than 98% homology to SEQ ID NO: 55, in which the glycine residue at position 56 is replaced with another amino acid residue, so long as the gene can promote export of L-lysine to the outside of a methanol-assimilating bacterium.

(3) lysE24 m5 Gene

This gene includes a DNA having the nucleotide sequence of the lysE24 gene, which has been modified so that each reading frame includes a stop codon, and promotes export of L-lysine, L-arginine, or both to the outside of a methanol-assimilating bacterium when the DNA is introduced into the bacterium. Specific examples thereof include the DNA having the nucleotide sequence of SEQ ID NO: 56 (WO 2006/059715). The gene may be a DNA which is able to hybridize with a complementary strand of the nucleotide sequence of SEQ ID NO: 56 or a probe that can be prepared from the nucleotide sequence under stringent conditions so long as the gene encodes a protein having activity for promoting export of L-lysine to the outside of a cell.

<ddh Gene>

The diaminopimelate dehydrogenase activity can be enhanced using a gene encoding diaminopimelate dehydrogenase (hereinafter, also referred to as the ddh gene).

An example of the ddh gene includes, but is not limited to, a DNA encoding diaminopimelate dehydrogenase derived from, or native to, a coryneform bacterium (SEQ ID NO: 53).

The ddh gene may be a DNA encoding a protein having not less than 80%, preferably not less than 90%, more preferably not less than 95%, particularly preferably not less than 98% homology to the entire amino acid sequence of SEQ ID NO: 53 and having the diaminopimelate dehydrogenase activity.

The ddh gene may also be a DNA encoding the protein having a sequence of SEQ ID NO: 53, but which includes one or several amino acid substitutions, deletions, insertions, additions, or the like so long as diaminopimelate dehydrogenase activity is not impaired.

Moreover, the ddh gene may be a DNA which is able to hybridize with a complementary strand of the nucleotide sequence of SEQ ID NO: 52 or a probe that can be prepared from the nucleotide sequence under stringent conditions so long as the gene encodes a protein having the diaminopimelate dehydrogenase activity.

The definitions of the terms "several" and "stringent conditions" and preferable amino acid substitution are the same as described above.

The ddh gene from coryneform bacterium can be obtained by amplification through PCR using two oligonucleotide primers (for example, SEQ ID NOS: 11 and 12 described in WO/9516042, U.S. Pat. No. 6,040,160), which are prepared based on the known nucleotide sequence of ddh from Corynebacterium glutamicum (Ishino, S. et al., Nucleic Acid Res., 15, 3917 (1987)) and using the chromosomal DNA of Brevibacterium lactofermentum or Corynebacterium glutamicum as the template.

<lysA Gene>

The diaminopimelate decarboxylase activity can be enhanced using the diaminopimelate decarboxylase gene (hereinafter, also referred to as the lysA gene). An example of the lysA gene includes, but is not limited to, a DNA encoding diaminopimelate decarboxylase derived from, or native to, a bacterium belonging to the genus Methylophilus (SEQ ID NO: 49).

The lysA gene may be a DNA encoding a protein having not less than 80%, preferably not less than 90%, more preferably not less than 95%, particularly preferably not less than 98% homology to the entire amino acid sequence of SEQ ID NO: 49 and having the diaminopimelate decarboxylase activity.

The lysA gene may also be a DNA encoding a protein having the sequence of SEQ ID NO: 49, but which includes one or several amino acid substitutions, deletions, insertions, additions, or the like so long as diaminopimelate decarboxylase activity is not impaired.

Moreover, the lysA gene may be a DNA which is able to hybridize with a complementary strand of the nucleotide sequence of SEQ ID NO: 48 or a probe that can be prepared from the nucleotide sequence under stringent conditions so long as the gene encodes a protein having diaminopimelate decarboxylase activity.

The definitions of the terms "several" and "stringent conditions" and preferable amino acid substitutions are the same as described above.

The lysA gene of Methylophilus methylotrophus can be obtained by PCR using two oligonucleotide primers prepared based on the known sequence and using the chromosomal DNA of Methylophilus methylotrophus as the template.

<dapB Gene>

The dihydrodipicolinate reductase activity can be enhanced using a gene encoding dihydrodipicolinate reductase (hereinafter, also referred to as the dapB gene). An example of the dapB gene includes, but is not limited to, a DNA encoding dihydrodipicolinate reductase derived from, or native to, a bacterium belonging to the genus *Escherichia* (SEQ ID NO: 43).

The dapB gene may be a DNA encoding a protein having not less than 80%, preferably not less than 90%, more preferably not less than 95%, particularly preferably not less than 98% homology to the entire amino acid sequence of SEQ ID NO: 43 and having dihydrodipicolinate reductase activity.

The dapB gene may also be a DNA encoding the protein having a sequence of SEQ ID NO: 43, but which includes one or several amino acid substitutions, deletions, insertions, additions, so long as the dihydrodipicolinate reductase activity is not impaired.

Moreover, the dapB gene may be a DNA which is able to hybridize with a complementary strand of the nucleotide sequence of SEQ ID NO: 42 or a probe that can be prepared from the nucleotide sequence under stringent conditions so long as the gene encodes a protein having the dihydrodipicolinate reductase activity.

The definitions of the terms "several" and "stringent conditions" and preferable amino acid substitutions are the same as described above.

The dihydrodipicolinate reductase gene (dapB) can be amplified by PCR using two oligonucleotide primers prepared based on the known nucleotide sequence and using the chromosomal DNA of *E. coli* as a template.

<asd Gene>

The aspartate-semialdehyde dehydrogenase activity can be enhanced using the gene encoding aspartate-semialdehyde dehydrogenase (hereinafter, also referred to as the asd gene). An example of the asd gene includes, but is not limited to, a DNA encoding aspartate-semialdehyde dehydrogenase derived from, or native to, a bacterium belonging to the genus *Escherichia* (SEQ ID NO: 45).

The asd gene may be a DNA encoding a protein having not less than 80%, preferably not less than 90%, more preferably not less than 95%, particularly preferably not less than 98% homology to the entire amino acid sequence of SEQ ID NO: 45 and having the aspartate-semialdehyde dehydrogenase activity.

The asd gene may also be a DNA encoding a protein having the sequence of SEQ ID NO: 45, but which includes one or several amino acid substitutions, deletions, insertions, additions, or the like so long as the aspartate-semialdehyde dehydrogenase activity is not impaired.

Moreover, the asd gene may be a DNA which is able to hybridize with a complementary strand of the nucleotide sequence of SEQ ID NO: 44 or a probe that can be prepared from the nucleotide sequence under stringent conditions so long as the gene encodes a protein having aspartate-semialdehyde dehydrogenase activity.

The definitions of the terms "several" and "stringent conditions" and preferable amino acid substitutions are the same as described above.

The aspartate-semialdehyde dehydrogenase gene (asd) can be amplified by PCR using two oligonucleotide primers prepared based on the known nucleotide sequence and using the chromosomal DNA of *E. coli* as the template.

<lysC* Gene>

The methanol-assimilating bacterium of the present invention may further include a DNA encoding aspartokinase that is desensitized to feedback inhibition by L-lysine.

Examples of a DNA encoding aspartokinase that is desensitized to feedback inhibition by L-lysine (hereinafter, also referred to as lysC* gene) preferably include, but are not limited to, a DNA encoding aspartokinase derived from, or native to, a bacterium belonging to the genus *Escherichia* and having a mutation to desensitize to feedback inhibition by L-lysine.

An example of the DNA encoding the wild-type aspartokinase derived from a bacterium belonging to the genus *Escherichia* includes the DNA encoding the amino acid sequence of SEQ ID NO: 47. An example of the mutation to desensitize feedback inhibition by L-lysine includes a mutation that replaces the threonine residue at position 352 with an isoleucine residue in the amino acid sequence of SEQ ID NO: 47 (T352I mutation). Therefore, an example of the lysC* gene includes a DNA encoding the amino acid sequence of SEQ ID NO: 47 in which the threonine residue at position 352 is replaced with an isoleucine residue.

The lysC* gene may be a DNA encoding a protein having not less than 80%, preferably not less than 90%, more preferably not less than 95%, particularly preferably not less than 98% homology to the entire amino acid sequence of SEQ ID NO: 47, having the T352I mutation, and having the aspartokinase activity.

The lysC* gene may also be a DNA encoding the protein having the sequence of SEQ ID NO: 47, but which includes one or more amino acid substitutions, deletions, insertions, additions, or the like so long as it has the T352I mutation and aspartokinase activity is not impaired.

Moreover, the lysC* gene may be a DNA which is able to hybridize with a complementary strand of the nucleotide sequence of SEQ ID NO: 46 or a probe that can be prepared from the nucleotide sequence under stringent conditions so long as the gene has the T352I mutation and encodes a protein having aspartokinase activity.

The definitions of the terms "several" and "stringent conditions" and preferable amino acid substitutions are the same as described above.

The lysC* gene may be obtained by site-specific mutagenesis, or from the RSFD80 plasmid as described below.

It is not always necessary that the DNA encoding aspartokinase that is desensitized to feedback inhibition by L-lysine be mutated. That is, a wild-type protein may be used so long as the protein is not subject to feedback inhibition by L-lysine.

The phrase "intracellular activity is enhanced" means that the intracellular enzymatic activity is increased as compared with a wild-type strain (for example, the *M. methylotrophus* AS1 strain) or the parent strain (a strain in which intracellular activities of all of the enzymes specified in the present invention are not enhanced), and also means that the bacterium has enzymatic activity that the wild-type or parent strain do not have. Specifically, although a bacterium belonging to the genus *Methylophilus* does not have the dapA* gene, lysE gene, and ddh gene encoding diaminodipicolinate dehydrogenase, if the intracellular enzymatic activities are detected or one or more copies of the dapA* gene, mutant lysE gene, and ddh gene is amplified, then such a bacterium is considered to have increased intracellular activities.

Examples of a procedure for enhancing an intracellular activity include, but are not limited to, the following procedures and combinations thereof.

(1) increasing the copy number by transformation with a plasmid carrying a DNA encoding each protein.

(2) increasing the copy number by incorporating the DNA encoding each protein into the chromosome.

(3) increasing expression by modifying a promoter sequence of the gene encoding each protein.

Examples of a procedure for introducing the dapA* gene, mutant lysE gene, and ddh gene include, but are not limited to, the following procedures:

(1) increasing the copy number by transformation with a plasmid carrying a DNA encoding each protein.

(2) increasing the copy number by incorporating the DNA encoding each protein into the chromosome.

In addition, these procedures may be combined with modifying the promoter sequence.

The increase in enzymatic activity can be confirmed by the methods described in the following references: Yugari. Y et al. (Biochim Biophys. Acta 62 612-614 1962) for dihydrodipicolinate synthase (E4.2.1.52), Misono, H et al. (J. Biol, Chem. 255, 10599-10605 1980) for a diaminodipicolinate dehydrogenase (EC:1.4.1.16), White. P. J et al. ((1965) Biochem, J, 96, 75-84) for a diaminopimelate decarboxylase (EC4.1.1.20), Kimura, H et al. (J. Biochem, 77, 405-413, 1975) for a dihydrodipicolinate reductase (EC:1.3.1.26), Black, S et al. (J. Biol Chem. 213 39-50 1955) for a aspartate-semialdehyde reductase (EC 1.2.1.11), and Truffa-Bachi et al. (The Enzymes (3$^{rd}$ ed.) 8, 509-553) for an aspartokinase (EC:2.7.2.4). *Methylophilus methylotrophus* AS1 strain (NCIMB10515) may be used as a control for any of these methods.

An increase in the enzymatic activity can be confirmed by comparing the amount of mRNA for the gene encoding each enzyme with that of the wild-type or unmodified strain. Examples of methods to confirm expression include Northern hybridization and RT-PCR (Molecular Cloning (Cold spring Harbor Laboratory Press, Cold spring Harbor (USA), 2001)). The activity or expression is increased as compared to that of the wild-type or unmodified strain, and it is desirably increased, for example, not less than 1.5-fold, preferably not less than 2-fold, more preferably not less than 3-fold, further more preferably not less than 5-fold, further more preferably not less than 10-fold as compared to that of the wild-type or unmodified strain. In particular, the enzymatic activity of a dihydrodipicolinate synthase is increased preferably not less than 10-fold, more preferably not less than 15-fold, and still more preferably not less than 20-fold.

The increase in the copy number can be confirmed by Southern hybridization using a probe complementary to the target gene. The gene is amplified preferably by 3 or more copies, more preferably by 5 or more copies, and still more preferably by 10 or more copies. In particular, 2 or more copies of the dapB gene, lysA gene, ddh gene, or asd gene is preferably present, and more preferably 3 or more copies; 3 or more copies of the lysC* gene is preferably present, and more preferably 4 or more copies; and 10 or more copies of the dapA gene or mutant lysE gene is preferably present, and more preferably 12 or more copies, and still more preferably 15 or more copies.

The methanol-assimilating bacterium has an L-lysine producing ability, which has been imparted by the above-mentioned modification, such as by enhancing the expression of each of the following genes: mutant lysE, dapA*, lysA, ddh, dapB, asd, and lysC*. The term "L-lysine producing ability" as used herein refers to an ability to cause accumulation of L-lysine in a medium to such a degree that L-lysine can be collected from the medium when the methanol-assimilating bacterium of the present invention is cultured in the medium.

The methanol-assimilating bacterium may be a mutant strain with an auxotrophic mutation, an analogue resistant mutation, and a metabolic regulation mutation, for example, and has been modified as described above.

For example, the bacterium may be a mutant strain which is auxotrophic for L-homoserine, or L-threonine and L-methionine (JP 48-28078 B and JP 56-6499 B), a mutant strain that is auxotrophic for inositol or acetic acid (JP 55-9784 A and JP 56-8692 A), or a mutant strain that is resistant to oxalysine, lysine hydroxamate, S-(2-aminoethyl)-cysteine, γ-methyllysine, α-chlorocaprolactam, DL-α-amino-ε-caprolactam, α-amino-lauryllactam, aspartic acid analogue, sulfa drug, quinoid or N-lauroylleucine, and has been modified as described above.

Auxotrophic mutations, analogue resistant mutations, and metabolic regulation mutations may be introduced after the modifications as described above, such as gene amplification.

A method of enhancing expression of the dihydrodipicolinate synthase gene (dapA* gene) and the aspartokinase gene (lysC* gene), both of which are not subject to feedback inhibition by L-lysine, will be described. The expression of mutant lysE gene, dapB gene, lysA gene, ddh gene, and asd gene can also be enhanced by the same method.

The expression of the dapA* gene and lysC* gene can be enhanced by transforming a host, such as a bacterium belonging to the genus *Methylophilus*, with a recombinant DNA prepared by ligating such DNA fragments with a vector that functions in the *Methylophilus* bacterium and preferably a multi-copy type vector. The increase in copy number of the genes results in enhancing the intracellular activities of enzymes encoded by target genes of dihydrodipicolinate synthase and aspartokinase. Hereinafter, dihydrodipicolinate synthase, aspartokinase, and aspartokinase III are also referred to as DDPS, AK, and AKIII, respectively.

The genes encoding DDPS and AK may be derived from any microorganism, so long the genes are able to express DDPS and AK activity in bacteria belonging to the genus *Methylobacillus*. Such microorganisms may be wild-type strains, or mutant strains derived therefrom. Specifically, examples of such microorganisms include *E. coli* (*Escherichia coli*) K-12 strain and *Methylophilus methylotrophus* AS1 strain (NCIMB10515). Since nucleotide sequences for the genes encoding DDPS (Richaud, F. et al., J. Bacteriol., 297 (1986)) and AKIII (Cassan, M., Parsot, C., Cohen, G. N. and Patte, J. C., J. Biol. Chem., 261, 1052 (1986)) are known, these genes can be obtained by PCR using primers synthesized based on the known nucleotide sequences of these genes, and using chromosomal DNA of a microorganism such as *E. coli* K-12 as the template. Hereinafter, dapA and lysC derived from *E. coli* will be exemplified, but the genes which may be used are not limited thereto.

The DDPS and AK are preferably not subject to feedback inhibition by L-lysine. It is known that wild-type DDPS derived from *E. coli* is subject to feedback inhibition by L-lysine, and that wild-type AKIII derived from *E. coli* is subject to suppression and feedback inhibition by L-lysine. Therefore, a mutation must be introduced into the genes that eliminates the feedback inhibition by L-lysine.

However, it is not always necessary to mutate the DDPS and AK genes because, for example, DDPS derived from a bacterium belonging to the genus *Corynebacterium* is not subject to feedback inhibition by L-lysine.

The dapA* and the lysC* which respectively encode DDPS and AK that are desensitized to feedback inhibition by L-lysine can be obtained by PCR using a plasmid containing the genes as the template, and using two oligonucleotide primers prepared based on the known nucleotide sequences.

The broad-host-range plasmid RSFD80 is known to contain the dapA* and lysC* genes (WO 95/16042). The *E. coli* JM109 strain transformed with this plasmid was designated as AJ12396, and deposited at the National Institute of Bioscience and Human-Technology, Agency of Industrial Science and Technology, Ministry of International Trade and Industry (currently, National Institute of Advanced Industrial Science and Technology, International Patent Organism Depositary) on Oct. 28, 1993 under the accession number FERM P-13936. Then, the deposit was converted to an international deposit under the provisions of the Budapest Treaty on Nov. 1, 1994 and given the accession number FERM BP-4859. RSFD80 can be obtained from the AJ12396 strain by a known method.

The dapA* in RSFD80 has the nucleotide sequence of the wild-type dapA gene (SEQ ID NO: 40) in which the C at nucleotide number 597 is replaced with a T, and thereby mutant DDPS encoded by the gene has the amino acid sequence of SEQ ID NO: 41 in which the histidine residue at position 118 is replaced with a tyrosine residue. The lysC* in RSFD80 has the nucleotide sequence of the wild-type lysC gene (SEQ ID NO: 46) in which the C at nucleotide number 1638 is replaced with a T, and mutant AKIII encoded by the gene has the amino acid sequence of SEQ ID NO: 47 in which the threonine residue at position 352 is replaced with an isoleucine residue.

Any plasmid may be used for gene cloning so long as it can replicate in microorganisms such as bacteria belonging to the genus *Escherichia*. Specifically, examples of such plasmids include pBR322, pTWV228, pMW119, and pUC19.

Vectors that function in bacteria belonging to the genus *Methylophilus* include, for example, a plasmid that can autonomously replicate in bacteria belonging to the genus *Methylophilus*. Specifically, examples thereof include RSF1010, which is a broad-host-range vector, and derivatives thereof, for example, pAYC32 (Chistorerdov, A. Y., Tsygankov, Y. D. Plasmid, 16, 161-167 (1986)), pMFY42 (Gene, 44, 53 (1990)), pRP301, and pTB70 (Nature, 287, 396, (1980)). Examples also include pBBR1 which is a broad-host-range vector having a different incompatibility from RSF1010, and derivatives thereof, such as pBHR1 (Antoine, R. and Locht, C., Molecular Microbiology, 6, 1785-99. (1992).).

To prepare a recombinant DNA via ligation of dapA*, lysC*, and DNAs encoding another protein into a vector that functions in bacteria belonging to the genus *Methylophilus*, the vector is digested with a restriction enzyme suitable for the terminus of the DNA fragment containing the genes. The ligation is usually performed with a ligase such as T4 DNA ligase. The genes may be introduced by separate vectors or the same vector.

The usual methods well known to those with skill in the art can be used for digestion, ligation of DNA, preparation of chromosomal DNA, PCR, preparation of plasmid DNA, transformation, design of oligonucleotides used as primers, and the like. Such methods are described in Sambrook, J., Fritsch, E. F., and Maniatis, T., "Molecular Cloning A Laboratory Manual, Second Edition", Cold Spring Harbor Laboratory Press (1989) and the like.

Any method can be used to introduce recombinant DNA prepared as described above into a bacterium belonging to the genus *Methylophilus*, so long as it provides sufficient transformation efficiency. For example, electroporation can be used (Canadian Journal of Microbiology, 43, 197 (1997)).

The DDPS and AK activities may also be enhanced by the presence of multiple copies of dapA* and lysC* on the chromosomal DNA of a bacterium belonging to the genus *Methylobacillus*. Multiple copies of dapA* and lysC* may be introduced into the chromosomal DNA of the bacterium belonging to the genus *Methylobacillus* by homologous recombination, which can be performed by using a sequence present on chromosomal DNA in multiple copies as a target. A repetitive DNA or an inverted repeat present at the end of a transposable element can also be used as the sequence present on the chromosomal DNA in multiple copies. Alternatively, as disclosed in JP 02-109985 A, multiple copies of dapA* and/or lysC* can be introduced into the chromosomal DNA by incorporating them into a transposon and transferring it. In both of the methods, the activities of DDPS and AK are amplified as a result of increased copy numbers of dapA* and lysC* in the transformant strains. In particular, the transposon is preferably a mini-Mu derived from Mu phage.

In addition to the above-described gene amplification methods, the DDPS activity and AK activity can be amplified by replacing expression control sequences such as promoters of dapA* and lysC*, with stronger ones (see JP 01-215280 A). Examples of known strong promoters include, for example, lac promoter, trp promoter, trc promoter, tac promoter, PR promoter of lambda phage, PL promoter, tet promoter, amyE promoter, and spac promoter. Use of these strong promoters will enhance expression of dapA* and lysC*, and thus DDPS activity and AK activity are increased. Enhancing the expression control sequences can be combined with increasing the copy number of dapA* and lysC*.

The bacterium of the present invention is not particularly limited so long as it is a methanol-assimilating bacterium which carries a DNA encoding a dihydrodipicolinate synthase which is desensitized to feedback inhibition by L-lysine and a DNA encoding a mutant LysE protein that promotes export of L-lysine to the outside of the bacterial cell when the DNA is introduced into the methanol-assimilating bacterium, wherein said bacterium is further modified to enhance intracellular activities of diaminopimelate dehydrogenase, diaminopimelate decarboxylase, dihydrodipicolinate reductase, and aspartate-semialdehyde dehydrogenase. Examples thereof include *Methylophilus methylotrophus* AJ110196 strain (FERM BP-10434) and microorganisms derived from AJ110196 (derivative strains). The term "derivative strains" as used herein refers to strains that are obtained from the parent strain AJ110196, which may be modified so that expression of the DNA encoding a dihydrodipicolinate synthase which is desensitized to feedback inhibition by L-lysine and the DNA encoding a mutant LysE protein that promotes export of L-lysine to the outside of the bacterial cell when the DNA is introduced into the methanol-assimilating bacterium are further enhanced, or so that intracellular activities of diaminopimelate dehydrogenase, diaminopimelate decarboxylase, dihydrodipicolinate reductase, and aspartate-semialdehyde dehydrogenase are further enhanced, or as described below, may be modified so as to have another property.

In addition to enhancing expression of the above-mentioned six or seven kinds of genes, other enzymes involved in the L-lysine biosynthesis may also be enhanced. Such enzymes include diaminopimelic acid pathway enzymes (JP 2003-135066 A) such as phosphoenolpyruvate carboxylase (JP 60-87788 A), aspartate aminotransferase (JP 06-102028 B), and diaminopimelate epimerase; and an aminoadipic acid pathway enzyme such as homoaconitate hydratase. Moreover, activity of 6-phosphogluconate dehydratase or an Entner-Doudoroff pathway enzyme such as 2-keto-3-deoxy-6-phosphogluconate aldolase may be enhanced (JP 2004-166595 A, U.S. Pat. No. 7,217,543).

Furthermore, the methanol-assimilating bacterium of the present invention may have decreased activity of an enzyme that catalyzes a reaction that generates a compound other than L-lysine, and branches off from the L-lysine biosynthetic pathway, or may be deficient in such an enzyme. Examples of an enzyme that catalyzes a reaction that generates a compound other than L-lysine and branches off from the L-lysine biosynthetic pathway include homoserine dehydrogenase (WO 95/23864) and L-lysine decarboxylase (JP 2004-

254544 A). Decreasing enzymatic activities can be achieved by a technology such as gene disruption using homologous recombination.

The methanol-assimilating bacterium of the present invention may be further modified to be auxotrophic for L-methionine (JP 2004-248669 A, U.S. Pat. No. 7,211,416). Such modification can be achieved by a natural mutation or a inducing a mutation of the methanol-assimilating bacterium so that the bacterium cannot grow in a medium without L-methionine or by disruption of the metA (JP 2004-248669 A, U.S. Pat. No. 7,211,416) or metF genes (SEQ ID NO: 58).

<3> Production of L-Lysine

L-lysine can be produced by culturing the *Methylophilus* bacterium having L-lysine producing ability in a medium to produce and accumulate L-lysine in culture, and collecting L-lysine from the culture medium.

The microorganism can be cultured by a method typically used in the culture of a methanol-assimilating microorganism. The medium used for the present invention may be either natural or synthetic so long as it contains a carbon source, nitrogen source, inorganic ions, and other trace amount organic components as required.

If methanol is used as the main carbon source, L-lysine can be produced at a low cost. When methanol is used as the main carbon source, methanol is added to the medium in an amount of between 0.001 to 30%. As the nitrogen source, ammonium sulfate or the like is used by adding it to the medium. In addition to these, trace amount components such as potassium phosphate, sodium phosphate, magnesium sulfate, ferrous sulfate, and manganese sulfate can be added in small amounts.

The culture is performed under aerobic conditions by shaking, aeration by stirring, or the like at pH of between 5 to 9, and temperature of between 20 to 45° C., and the culture is typically complete within 24 to 120 hours.

L-lysine can usually be collected from culture by a combination of ion exchange resin method, precipitation method, and other known methods.

EXAMPLES

The present invention will be further specifically explained with reference to the following non-limiting examples.

The reagents used in the following examples were obtained from Wako Pure Chemicals Industries, Ltd. or Nacalai Tesque, Inc. unless otherwise indicated. The compositions of the medium used in each example are shown below. pH was adjusted with NaOH or HCl for all of the medium.

LB Medium:
Tryptone/peptone (manufactured by Difco) 10 g/L
yeast extract (manufactured by Difco) 5 g/L
NaCl 10 g/L
pH 7.0
These were steam-sterilized at 120° C. for 20 minutes.
LB Agar Medium:
LB medium
Bacto agar 15 g/L
This was steam-sterilized at 120° C. for 20 minutes.
SEII Medium:
$K_2HPO_4$ 1.9 g/L
$NaH_2PO_4$ 1.56 g/L
$MgSO_4.7H_2O$ 0.2 g/L
$(NH_4)_2SO_4$ 5 g/L
$CuSO_4.5H_2O$ 5 µg/L
$MnSO_4.5H_2O$ 25 µg/L
$ZnSO_4.7H_2O$ 23 µg/L
$CaCl_2.2H_2O$ 72 m g/L
$FeCl_3.6H_2O$ 9.7 m g/L
Methanol 0.5% (vol/vol) pH 7.0
The components other than methanol were steam-sterilized at 121° C. for 15 minutes. After the components were sufficiently cooled, methanol was added.
SEII Production Medium:
$K_2HPO_4$ 1.9 g/L
$NaH_2PO_4$ 1.56 g/L
$MgSO_4.7H_2O$ 0.2 g/L
$(NH_4)_2SO_4$ 5 g/L
$CuSO_4.5H_2O$ 5 µg/L
$MnSO_4.5H_2O$ 25 µg/L
$ZnSO_4.7H_2O$ 23 µg/L
$CaCl_2.2H_2O$ 72 mg/L
$FeCl_3.6H_2O$ 9.7 mg/L
Sodium pyruvate 2.5 g/L
$CaCO_3$ (manufactured by Kanto Chemical Co., Inc.) 30 g/L
Methanol 2% (vol/vol) pH 7.0
The components other than methanol were steam-sterilized at 121° C. for 15 minutes. After the components were sufficiently cooled, methanol was added.
SEII Agar Medium:
$K_2HPO_4$ 1.9 g/L
$NaH_2PO_4$ 1.56 g/L
$MgSO_4.7H_2O$ 0.2 g/L
$(NH_4)_2SO_4$ 5 g/L
$CuSO_4.5H_2O$ 5 µg/L
$MnSO_4.5H_2O$ 25 µg/L
$ZnSO_4.7H_2O$ 23 µg/L
$CaCl_2.2H_2O$ 72 mg/L
$FeCl_3.6H_2O$ 9.7 mg/L
Sodium pyruvate 1.0 g/L
Methanol 1% (vol/vol)
pH 7.0
Bacto Agar (manufactured by Difco) 15 g/L
The components other than methanol were steam-sterilized at 121° C. for 15 minutes. After the components were sufficiently cooled, methanol and if required, 20 g/L L-methionine solution were added after filter sterilization.

Example 1

Construction of the Mini-Mu System, pMIV-Km, pMIV-Km-EA, pAET7

A gene incorporation system using the bacteriophage Mu-phage isolated from *Escherichia coli* was used to increase the copy number of the lysE24 gene (a DNA encoding a mutant LysE protein) and the mutant dapA gene (a DNA encoding a dihydrodipicolinate synthase which is desensitized to feedback inhibition by L-lysine) on the chromosome.

Figure 2:
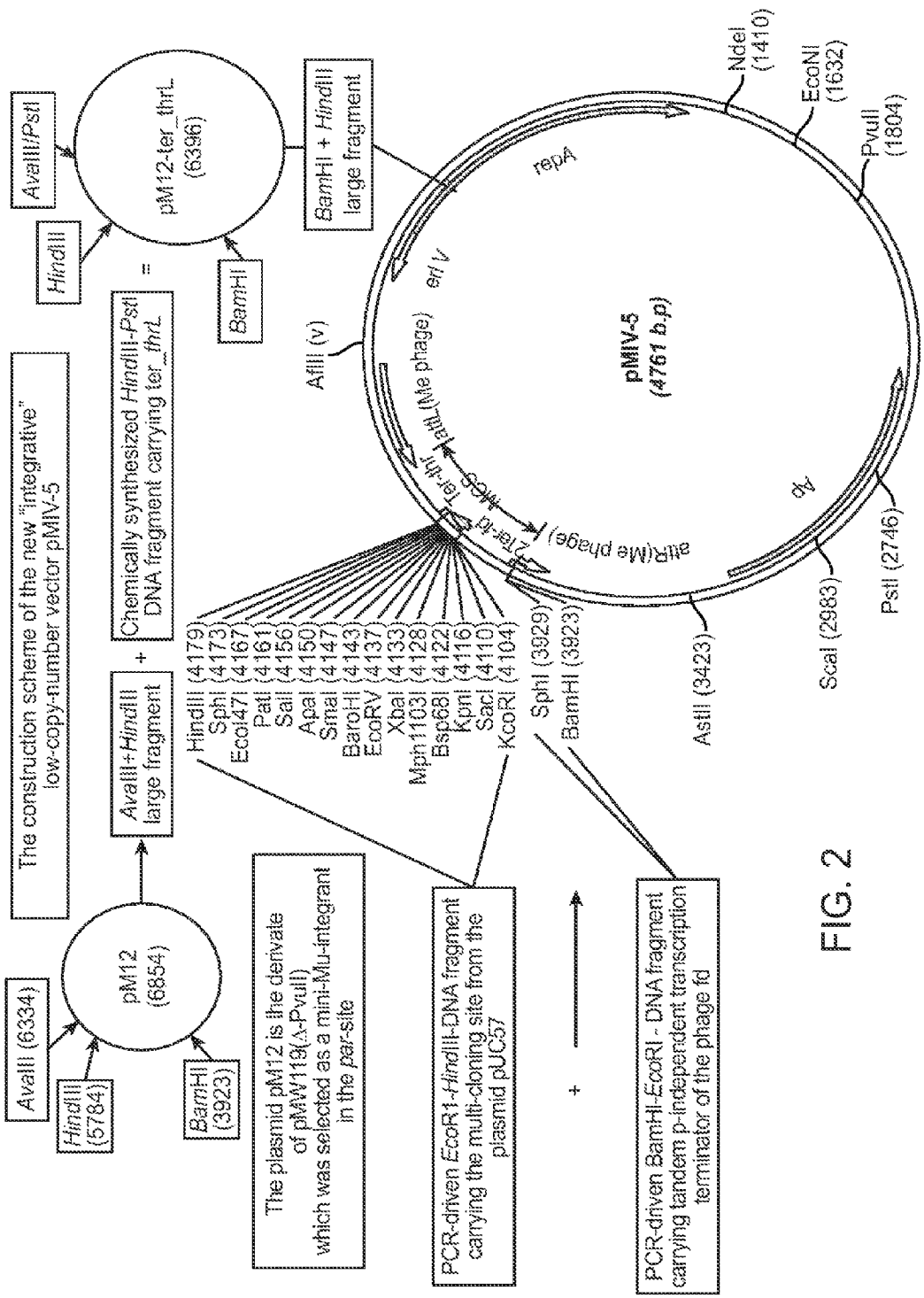
FIG. 2 is an illustration showing the construction of plasmid pMIV5.

Construction of pMIV5 (FIGS. 1 and 2)

In order to incorporate Mu-phage into the chromosome of *Escherichia coli*, a drug resistance gene located between the recognition sequences attL and attR, and a transferase (Mu transposase) are required. It is not always necessary that both of them are incorporated into the same vector, and first, the pMIV5 plasmid was constructed, which contains the recognition sequences attL and attR and a kanamycin resistance gene, while the pAET7 plasmid with the Mu transposase was constructed separately. Both of the plasmids can function when they are present in the same bacterium, resulting in the transfer of the region located between attL and attR to the chromosomal DNA of the strain.

The pMIV5 plasmid was constructed as follows. First, pMW119 (available from TOYOBO Co., Ltd.) is digested with the PvuII restriction enzyme and separated by agarose gel electrophoresis to collect a fragment of about 3.9 kbp. This fragment was ligated with the DNA Ligation Kit (Takara Bio Inc.), to obtain the pMW1 plasmid. Subsequently, mini-Mu-phage was transferred to the pMW1 plasmid in E. coli cells. Specifically, pMD4041 (Journal of Bacteriology 158, 488-495 (1984)) was introduced into the Escherichia coli K12 strain, and a strain resistant to kanamycin and sensitive to ampicillin was selected to obtain a strain in which the plasmid pMD4041 was eliminated and mini-Mu 4041 was transferred to the chromosome. A factor that represses Mu transfer of mini-Mu4041, for example, c repressor, has a temperature-sensitive mutation. Therefore, when the strain is cultured at 42° C., c repressor of mini-Mu on the chromosome is deactivated, and transfer of mini-Mu4041 is significantly activated to cause effective transfer of mini-Mu to the chromosome, resulting in cell death. The strain with lysogenized mini-Mu4041 on the chromosome was transformed with pMW1 at 30° C. This strain with the plasmid pMW1 was cultured in LB medium until the number of cells reached $2 \times 10^8$ cells/ml and treated at 42° C. for 1 hour. In order to obtain a plasmid with mini-Mu4041 transferred to the pMW1 plasmid, plasmid DNA was prepared from the cells and used to transform an Escherichia coli strain. Plasmids were prepared from 50 strains of transformants having kanamycin resistance and ampicillin resistance, and the structures of the plasmids were determined by treating with a restriction enzyme, to thereby select the plasmid of interest. This plasmid was designated as pMu11. In the plasmid pMu11, mini-Mu4041 was transferred to the par region in the pMW1. More specifically, in pMW119 containing fragments of the known plasmids pBR322 and pSC101, mini-Mu4041 was inserted into the position 259, where the boundary position between the plasmids was defined as position 0. The plasmid was digested with the HindIII restriction enzyme and separated by agarose gel electrophoresis to collect a fragment of about 6.9 kbp, and this fragment was ligated with the DNA Ligation Kit (Takara Bio Inc.), to construct the pM12 plasmid (FIG. 1). pM12 was digested with HindIII-AvaIII (EcoT22I) and used as a vector into which the terminator region of the PCR-amplified thr operon of E. coli was inserted. PCR amplification was performed using the chromosomal DNA of E. coli as the template and p-ter-thrL-f (SEQ ID NO: 1) and p-ter-thrL-r (SEQ ID NO: 2) as primers, under the following conditions for 25 cycles: denaturation at 94° C. for 20 seconds, annealing at 55° C. for 30 seconds, and extension at 72° C. for 60 seconds. The resulting plasmid was digested with the EcoRI-HindIII restriction enzyme, and the PCR-amplified multi-cloning site region and the PCR-amplified ρ-factor independent transcription termination factor fragment from a bacteriophage fd were inserted into the plasmid. The multi-cloning site region was amplified by PCR using the pUC57 plasmid (Fermentus AB, available from LITHUANIA) as the template and pUC57-MCS-f (SEQ ID NO: 3:) and pUC57-MCS-r (SEQ ID NO: 4) as primers, and PCR was performed under the following conditions for 25 cycles: denaturation at 94° C. for 20 seconds, annealing at 55° C. for 30 seconds, and extension at 72° C. for 30 seconds. The amplified fragment was digested with EcoRI-BamHI, the recognition sites of which had been added into the primer. The ρ-factor independent transcription termination factor fragment was amplified by PCR using the genomic DNA of the bacteriophage fd as the template and ter-fd-f (SEQ ID NO: 5) and ter-fd-r (SEQ ID NO: 6:) as primers, and PCR was performed under the following conditions for 25 cycles: denaturation at 94° C. for 20 seconds, annealing at 55° C. for 30 seconds, and extension at 72° C. for 30 seconds. The amplified fragment was digested with EcoRI-HindIII, recognition sites of which had been added into the primer. The three fragments were ligated with the DNA Ligation kit (Takada Bio Inc.) to construct the pMIV5 plasmid (FIG. 2). Then, the plasmid was digested with EcoRV, and a kanamycin resistance gene fragment obtained by cleaving a commercially-available plasmid (pUC4K) with HincII was inserted into the plasmid to construct the pMIV5-Km plasmid.

pMIV-Km-lysE24dapA

A gene of interest was inserted into the pMIV5-Km plasmid and used to incorporate the gene with mini-Mu, and the plasmid was used to transfer the gene fragment of interest to the chromosome. Specifically, the plasmid pMIV5-Km was digested with SmaI, followed by a dephosphorylation treatment. On the other hand, the fragment lysE24+dapA* was obtained by amplification through PCR using a known plasmid containing the pRSlysEdapA gene (JP 2003-61687A), as the template and pRS-1s (SEQ ID NO: 8:) and dapA-r (SEQ ID NO: 7:) as primers. PCR was performed under the following conditions for 25 cycles: denaturation at 94° C. for 20 seconds, annealing at 55° C. for 30 seconds, and extension at 72° C. for 120 seconds. PCR-amplified fragments were ligated with the TaKaRa BKL kit (Takara Bio Inc.) to construct the pMIV-Km-lysE24dapA plasmid.

Figure 4:
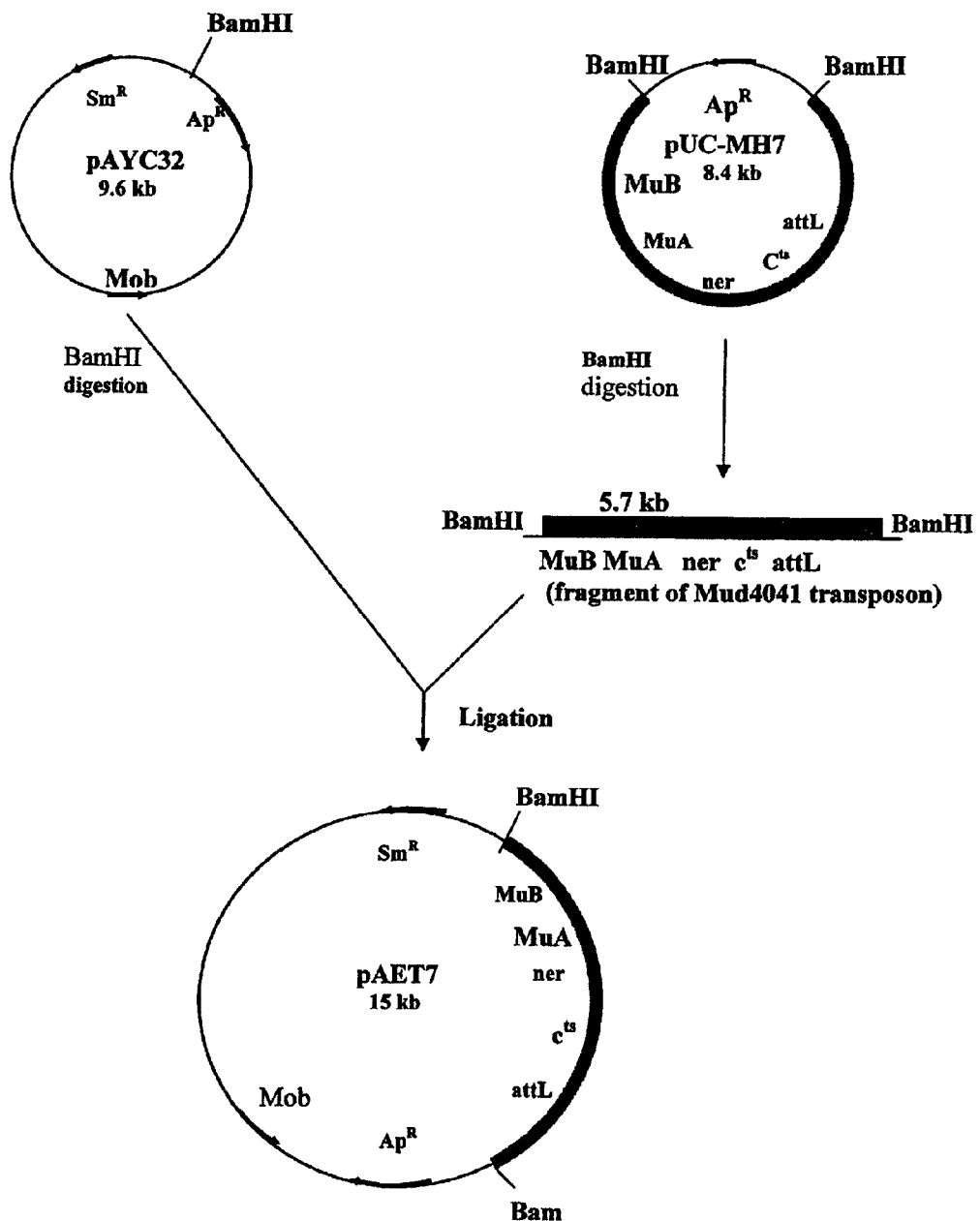
FIG. 4 is an illustration showing the construction of plasmid pAET7.
Figure 5:
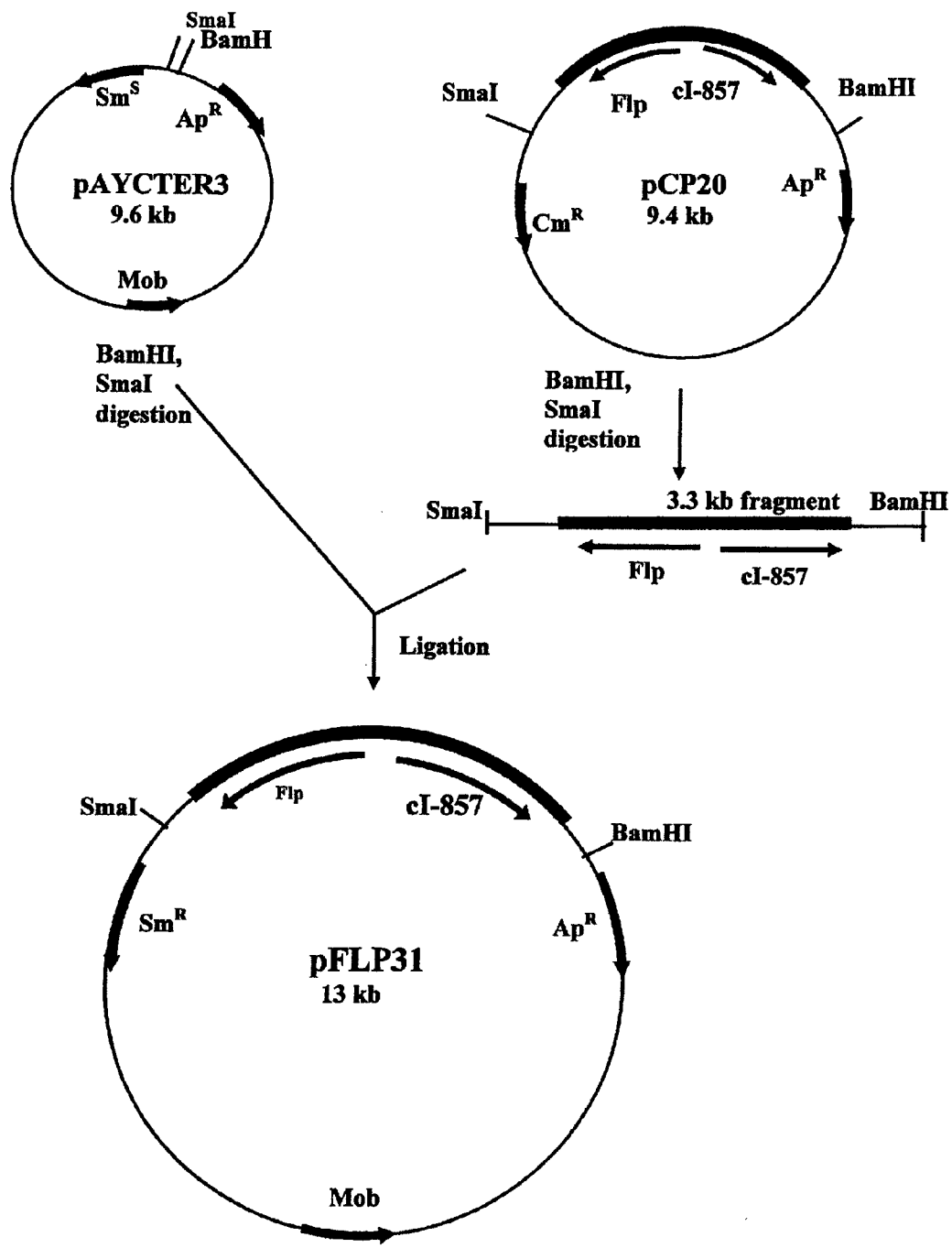
FIG. 5 is an illustration showing the construction of plasmid pFLP31.

Construction of pAET7 (FIG. 4)

pUC1918 (Gene, (1993) 134, 89-91) was digested with the EcoRI restriction enzyme, and the resulting fragment was blunt-ended. This fragment was used to insert the product obtained by blunt-ending a DNA fragment encoding Mu transposase, and a DNA fragment was obtained by digesting pMu4041 (Journal of Bacteriology, (1984), 158, 488-495) with ScaI-Eco47III. This plasmid was designated as pUC-MH7. pUC-MH7 was digested with BamHI, and the resulting DNA fragment encoding Mu transposase was inserted into the BamHI site of pAYC32 (Journal of General Microbiology 137, 169-178 (1991)) to obtain the pAET7 plasmid.

Example 2

Incorporation of the lysE24 and Mutant dapA Genes into the Chromosome of Methylophilus methylotrophus, and the Acquisition of VAE#1

First, pAET7 was introduced into the M. methylotrophus AS strain by electroporation, and the bacterium was inoculated onto an SEII plate containing 50 mg/l streptomycin. Then, the pMIV-Km-lysE24dapA plasmid was introduced into the resulting transformant to obtain strains that formed colonies on the SEII plate containing 20 mg/l kanamycin and 50 mg/l streptomycin. The mini-Mu cassette includes a kanamycin resistance gene, and the pMIV-Km-lysE24dapA plasmid, which cannot replicate in M. methylotrophus. Therefore, the kanamycin-resistant strain has the mini-Mu cassette inserted into the chromosome. Accordingly, 200 strains were selected randomly from these strains and spread onto an SEII plate containing 50 mg/l streptomycin and 20 mg/L kanamycin, followed by culturing at 37° C. overnight. Then, bacterial cells present on the medium surface of about 0.3 square centimeters were scraped off and inoculated into an SEII production medium (5 ml) containing 50 mg/l streptomycin and 20 mg/L kanamycin, and the cells were cultured with shaking at 37° C. for 34 hours. After completion of the culture, the bacterial cells were removed by centrifugation, and the concentration of L-lysine in each culture supernatant was measured using Biotech-analyzer AS-210 (manufactured by Sakura Seiki Co., Ltd.). The strain containing the highest concentration L-lysine was selected and designated as VAE#1.

Example 3

Acquisition of a Strain where lysE24 and Mutant dapA Genes are Incorporated at Higher Copy Numbers (VAE#8)

The VAE#1 strain was shown to have one or two copies of the mini-Mu cassette inserted into the chromosome. Therefore, in order to improve productivity of L-lysine, the mini-Mu cassette was amplified on the chromosome. A gene encoding the MuC protein, which is capable of suppressing the Mu transposase activity, is on the pAET7 plasmid carrying the Mu transposase. The MuC protein is temperature sensitive, and therefore, when the strain is cultured at 42° C., the Mu transposase activity is promoted, resulting in amplification of the mini-Mu cassette on the chromosome. Specifically, the VAE#1 strain was suspended in SEII liquid medium to an appropriate concentration, and the suspension was incubated at 42° C. for 1 hour and diluted to appropriate concentrations. The bacterial solutions were inoculated onto SEII plates containing 50 mg/L streptomycin and 20 mg/L kanamycin to form single colonies. From the single colonies, 200 colonies were selected randomly and spread on SEII plates containing 50 mg/L streptomycin and 20 mg/L kanamycin, followed by culturing at 37° C. overnight. Then, bacterial cells present on the medium surface of about 0.3 square centimeters were scraped off and inoculated into an SEII production medium (5 ml) containing 50 mg/L streptomycin and 20 mg/L kanamycin, and the cells were cultured with shaking at 37° C. for 34 hours. After completion of the culture, the bacterial cells were removed by centrifugation, and the concentration of L-lysine in each culture supernatant was measured using a Biotech-analyzer AS-210 (manufactured by Sakura Seiki Co., Ltd.) to select the strain with the highest concentration of L-lysine. The strain was designated as VAE#2. The procedure was repeated 8 times to obtain the VAE#8 strain. The amount of Lys produced by VAE#1 was defined as 100, and the relative value of the amount of Lys produced by the VAE#8 strain was calculated and is shown in Table 1.

TABLE 1

| Name of strain | Relative amount of produced Lys (%) |
|---|---|
| VAE#1 | 100 |
| VAE#8 | 800 |

Example 4

Determination of Transfer Site in VAE#8

Next, the site to which the mini-Mu cassette was transferred onto the chromosome of the VAE#8 strain was determined The chromosomal DNA of the VAE#8 strain was prepared and completely digested with the SalI restriction enzyme. The resulting fragment was ligated to the pHSG398 vector, and selection was performed in an LB agar medium containing 12.5 mg/L chloramphenicol and 25 mg/L kanamycin to prepare plasmid DNA from the colonies. There is a kanamycin resistance gene on the mini-Mu cassette and chromosomal DNA around the transfer site in the plasmid. The nucleotide sequence of the plasmid was determined using a sequencing primer (SEQ ID NO: 9), which was designed outwardly in the inside of attR present on the right hand edge of the mini-Mu cassette, to thereby determine the transfer site of the mini-Mu cassette which was transferred to the chromosome. It is also possible to construct a strain identical to VAE#8 based on the information of the transfer region determined by the above-described method.

Example 5

Imparting Met-Auxotrophy to VAE#8 (#403)

Next, methionine auxotrophy was imparted to the VAE#8 strain Imparting amino acid auxotrophy to an amino acid-producing bacterium is effective to control the number of bacterial cells during the culture. The VAE#8 strain was subjected to NTG-mutation treatment by a known method (WO 00/61723, U.S. Pat. No. 7,223,572) and appropriately diluted to a cell density to form a single colony, and the bacterium was inoculated into an SEII agar medium containing 0.5 g/L L-methionine. The cells were replicated on an SEII agar medium containing no L-methionine to obtain a strain that could not grow on the plate, that is, a strain auxotrophic for L-methionine. The strain was designated as #403. A plurality of genes from the #403 strain, which was known to be involved in biosynthesis of L-methionine, were cloned by a method well-known to a person skilled in the art based on the homology to another microorganism to determine the nucleotide sequences. As a result, it was found that part of the metF gene encoding 5,10-methylenetetrahydrofolate reductase was deleted. Specifically, it was found that the region between the $92^{nd}$ nucleotide and the $344^{th}$ nucleotide, as counted from the initiation codon of the metF gene, was deleted. It was possible to impart L-methionine auxotrophy by disrupting the metF gene of VAE#8 by a known method (JP 2004-229662 A, Homologous recombination method using linear DNA). Details are described in Example 19. The strain with an artificially disrupted metF was found to have the same properties as a strain auxotrophic for L-methionine obtained by the above-described NTG-mutation treatment, #403. A DNA fragment for gene disruption was prepared by Over-lap-PCR (Ho, S. N., Hunt, H. D., Horton, R. M., Pullen, J. K. and Pease, L. R., Gene, 77, 51-9. (1989)). When the #403 strain and the control strain VAE#8 were cultured in SEII production medium containing 0.075 g/L L-methionine and 2.5 g/L sodium pyruvate, the amount of Lys was increased. The amount of Lys produced by the VAE#8 strain was defined as 100, and the relative value of the amount of Lys produced by the #403 strain was calculated and is shown in Table 2.

TABLE 2

| Name of strain | Relative amount of produced Lys (%) |
|---|---|
| VAE8 | 100 |
| #403 | 156 |

Example 6

Figure 3:
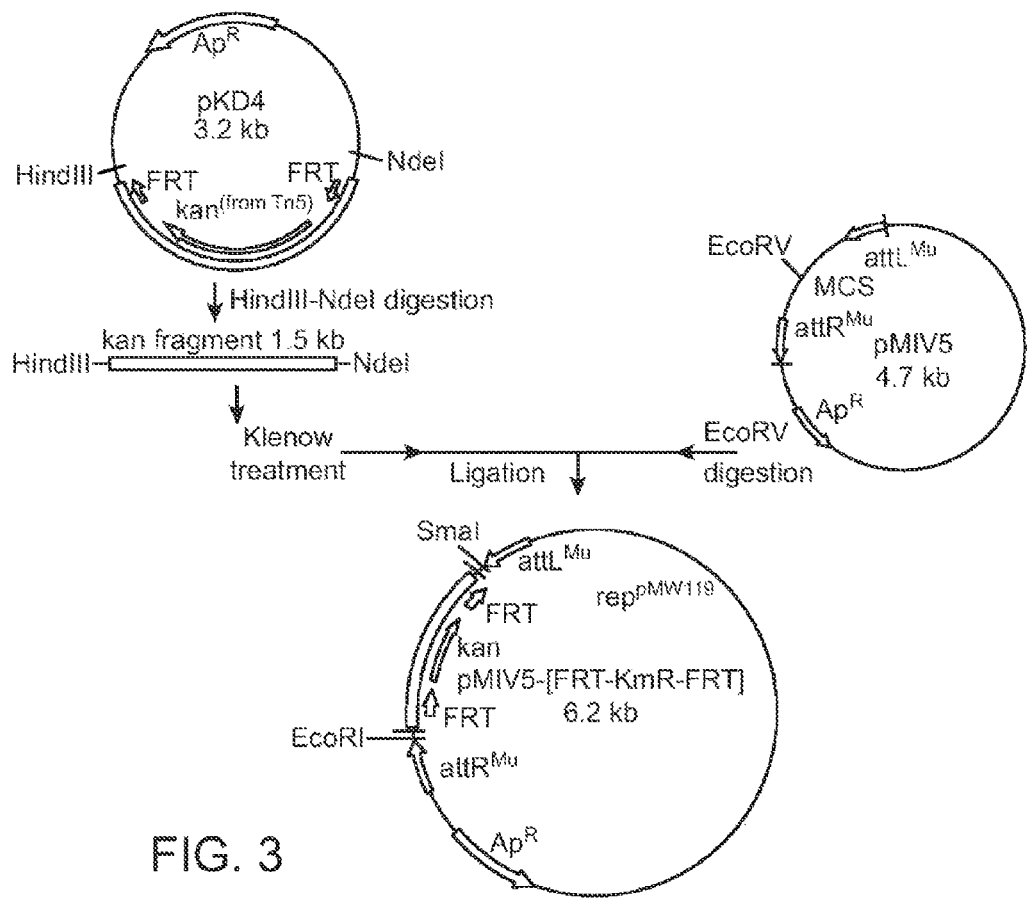
FIG. 3 is an illustration showing the construction of plasmid pMIV-FRTKmFRT.

Construction of the pMIV-FRTGmFRT and pMIV-FRTGmFRT-EA Plasmids (FIG. 3)

In order to further incorporate a mini-Mu cassette into the #403 strain, an insertion cassette having a gene resistant to an antibiotic other than kanamycin was constructed. Specifically, the pMIV5 plasmid was digested with EcoRV and used as a vector. Then, pKD4 (Proceedings of the National Academy of Sciences of the United States of America, (2000) 97, 6640-6645) was digested with HindIII-NdeI, and the resulting fragment was blunt-ended, followed by insertion of a fragment having the kanamycin resistance gene region. This plasmid was designated as pMIV-FRTKmFRT. The plasmid was digested with the BglII restriction enzyme, and the resulting fragment was blunt-ended, followed by insertion of the PCR-amplified gentamicin resistance gene fragment. PCR was performed using pML122 (Gene, 89, 37-46. (1990)) as the template and pGm-f (SEQ ID NO: 10) and pGm-r (SEQ ID NO: 11) as primers, under the following conditions for 25 cycles: denaturation at 94° C. for 20 seconds, annealing at 55° C. for 30 seconds, and extension at 72° C. for 60 seconds. The plasmid was designated as pMIV-FRTGmFRT. A gene of interest was inserted into the region between attL and attR to construct a mini-Mu cassette to amplify the gene of interest on the chromosome of *M. methylotrophus* (FIG. 3). Specifically, the pMIV-FRTGmFRT plasmid was digested with the SmaI restriction enzyme, followed by dephosphorylation. The lysE24+dapA* fragment was obtained by amplification with PCR using a known plasmid having the pRSlysEdapA gene (JP 2003-61687 A, U.S. Pat. No. 7,169,587) as the template and pRS-1s and dapA-r as primers. PCR was performed under the following conditions for 25 cycles: denaturation at 94° C. for 20 seconds, annealing at 55° C. for 30 seconds, and extension at 72° C. for 120 seconds. PCR-amplified fragments were phosphorylated using a TaKaRa BKL kit (Takara Bio Inc.) and ligated to a vector, to thereby construct the pMIV-FRTGmFRT-EA plasmid. The pKD4 and pCP20 plasmids were registered at the *E. coli* Genetic Stock Center as CGSC strains #7632 and #7629, respectively, and are available from the Center.

Example 7

Acquisition of a Strain in which the lysE24 and Mutant dapA Genes are Incorporated at Higher Copy Numbers Using pMIV-Gm-EA (#403-11-Gm)

First, pAET7 was introduced into the #403 strain, and the cells were inoculated onto an SEII plate containing 50 mg/l streptomycin. Then, the pMIV-FRTGmFRT-EA plasmid was introduced into the resulting pAET7 transformant by electroporation to obtain strains that formed colonies on an SEII plate containing 50 mg/l streptomycin. The mini-Mu cassette includes a gentamicin resistance gene, and the pMIV-FRTGmFRT-EA plasmid cannot replicate in *M. methylotrophus*. Therefore, the gentamicin-resistant strain has the mini-Mu cassette inserted into the chromosome. Accordingly, 200 strains were selected randomly from these strains and spread on an SEII plate containing 50 mg/L streptomycin and 20 mg/L gentamicin, followed by culturing at 37° C. overnight. Then, bacterial cells present on the medium surface of about 0.3 square centimeters were scraped off and inoculated into an SEII production medium (5 ml) containing 50 mg/l streptomycin and 20 mg/L gentamicin, and the cells were cultured with shaking at 37° C. for 48 hours. After completion of the culture, the bacterial cells were removed by centrifugation, and the concentration of L-lysine in each culture supernatant was measured using a Biotech-analyzer AS-210 (manufactured by Sakura Seiki Co., Ltd.) to select the strain with the highest concentration of L-lysine. The strain was designated as #403-11Gm.

Example 8

Determination of the Transfer Site in #403-11-gm

Next, the site to which the mini-Mu cassette was transferred onto the chromosome of the #403-11-Gm strain was determined The chromosomal DNA of the #403-11 strain was prepared and completely digested with the SalI restriction enzyme. The resulting fragment was ligated to the pHSG398 vector, and selection was performed in an LB agar medium containing 12.5 mg/L chloramphenicol and 25 mg/L gentamicin to prepare a plasmid DNA from the resulting colonies. There is a cloned kanamycin resistance gene on the mini-Mu cassette, as well as the chromosomal DNA around the transfer site in the plasmid. The nucleotide sequence of the plasmid was determined using a sequencing primer (SEQ ID NO: 12), which was designed in the attR region present on the right hand edge of the mini-Mu cassette, to thereby determine the transfer site of the mini-Mu cassette which had been transferred to the chromosome. It is also possible to construct a strain identical to #403-11Gm based on the information of the transfer region determined by the above-described method.

Example 9

Elimination of the Antibiotic-Resistant Marker from #403-11-Gm (pFLP31), and Acquisition of the #403-11 Strain Construction of pAYCTER3
Synthetic DNAs of SEQ ID NO: 13 and SEQ ID NO: 14, designed to contain the pUC19 multi-cloning site, were annealed by a well-known method to produce a polylinker. The polylinker was designed to have the same terminal as that of the fragment cleaved with restriction enzymes EcoRI and BglII. Moreover, the primers of SEQ ID NO: 15 and SEQ ID NO: 16 were synthesized, and the region encoding the rrnB terminator sequence was amplified by PCR from the chromosomal DNA of the *Escherichia coli* K-12 strain prepared by a conventional method (Saito and Miura [Biochim Biophys. Acta, 72, 619 (1963)]). The primers of SEQ ID NO: 13 and SEQ ID NO: 14 were designed to have the recognition sequence of the restriction enzyme BglII and the recognition sequence of the restriction enzyme BclI, respectively. PCR was performed using Pyrobest DNA polymerase (manufactured by Takara Bio Inc.) under reaction conditions recommended by the manufacturer. The resulting PCR fragment was digested with restriction enzymes BglII and BclI, and the PCR fragment was ligated to the above-mentioned polylinker, to produce a DNA fragment of about 400 bp. The ligation reaction was performed with a DNA Ligation Kit Ver.2.1 (manufactured by Takara Bio Inc.) under reaction conditions recommended by the manufacturer. Then, a fragment of about 9.2 kbp, obtained by cleaving pAYC32 (J. Gen. Microbiol., 137, 169-178 (1991)) with restriction enzymes EcoRI and BamHI, was collected, and the above-mentioned DNA fragment was inserted to construct the pAYCTER3 expression plasmid, which is capable of functioning in *M. methylotrophus* NCIMB 10515. pAYCTER3 lacks a sequence upstream on the 5' side of the strA gene, and alternatively has a pUC19 multi-cloning site and an rrnB terminator.

Construction of pFLP31
The gentamicin resistance gene of the #403-11Gm strain constructed in Example 7 was designed so that it is located between two FRT sequences, so the drug resistance gene can be eliminated from the chromosome by a reaction with FLP recombinase. pAYCTER3 constructed by the above-mentioned method was digested with BamHI-SmaI, and a 3.3-kbp fragment obtained by cleaving pCP20 (Proceedings of the National Academy of Sciences of the United States of America, (2000) 97, 6640-6645) with SmaI-BamHI containing an FLP recombinase was inserted. The resulting plasmid was designated as pFLP31. The plasmid pCP20 was registered at the *E. coli* Genetic Stock Center as CGSC strain #7629, and it is available from the Center.

Elimination of the Antibiotic-Resistance Marker pAET7 was eliminated from #403-11 Gm by a known method to obtain a streptomycin-sensitive strain. The above-mentioned plasmid pFLP31 was introduced into the strain by electroporation, and the cells were inoculated onto an SEII agar medium containing 50 mg/L streptomycin and 0.5 g/L L-methionine. The resulting strain was suspended to an appropriate concentration in an SEII agar medium containing 50 mg/L streptomycin and 0.5 g/L L-methionine. The suspension was heated to 42° C. for 1 hour and diluted to form single colonies, and the cells were inoculated onto an SEII agar medium containing 50 mg/L streptomycin and 0.5 g/L L-methionine. From the colonies, strains sensitive to gentamicin were selected. Then, pAET7 was eliminated from the strain to obtain a streptomycin-sensitive strain, which was designated as #403-11. When the #403-11 strain and a control strain (#403 strain) were cultured in an SEII production medium containing 0.075 g/L L-methionine and 2.5 g/L sodium pyruvate, the amount of Lys that was produced increased. The amount of Lys produced by the #403 strain was defined as 100, and the relative value of the amount of Lys produced by the #403-11 strain was calculated and shown in Table 3.

TABLE 3

| Name of strain | Relative amount of produced Lys (%) |
|---|---|
| #403 | 100 |
| #403-11 | 108 |

Example 10

Confirmation of Increased DDPS Activity

In #403-11 obtained as described above, 8 copies of the lysE24dapA cassette was transferred to the chromosome. Therefore, an increase in the activity of dihydrodipicolinate synthase encoded by dapA was confirmed for the #403-11 strain. The dihydrodipicolinate synthase activity was measured by modifying a known method (Journal of Biological Chemistry, 240, 4710-4716 (1965)). Specifically, a reaction solution was prepared so as to contain 50 mM imidazole-HCl (pH 7.4), 2 mM L-aspartate-β-semialdehyde, 2 mM sodium pyruvate, and a cell extract, and the final volume of the solution was adjusted to 1 ml. The results are shown in Table 4.

TABLE 4

| Name of bacterial strain | Specific activity (milliunit/milligram protein) |
|---|---|
| AS1 | 12 |
| #403-11 | 129 |

The amount of enzyme that produces 1 micromol of a product per minute was defined as 1 unit.

Example 11

Construction of the pBGEA Plasmid, and Construction of #403-11/pBGEA (1) Construction of the pBGEA Plasmid Carrying an L-Lysine Biosynthetic Enzyme Gene (dapA*) and a Gene Having L-Lysine Export Activity (lysE24)

In order to introduce the dapA* and LysE24 genes into a bacterium belonging to the genus *Methylophilus*, pBHR1 (Antoine, R. and Locht, C., Molecular Microbiology, 6, 1785-99. (1992)) was used to construct pBGEA for expressing dapA* and LysE24. First, pBHR1 was digested with the DraI restriction enzyme, and the resulting fragment was added to a phenol/chloroform solution and mixed to terminate the reaction. After the reaction mixture was centrifuged, the upper layer was collected, and DNA was collected by ethanol precipitation. The resulting DNA fragment was blunt-ended using a DNA Blunting kit (manufactured by Takara Shuzo).

On the other hand, the dapA* and LysE24 genes were obtained from pRSlysEdapA (JP 2003-61687 A, U.S. Pat. No. 7,169,587). The *E. coli* JM109 strain transformed with the pRSlysEdapA plasmid was designated as AJ13832 and deposited at National Institute of Advanced Industrial Science and Technology, International Patent Organism Depositary on Jun. 4, 2001 under the accession number FERM P-18371. Then, the deposit was converted to an international deposit under the provisions of the Budapest Treaty on May 13, 2002 under the accession number FERM BP-8042. First, pRSlysEdapA was digested with restriction enzymes EcoRI and BglII, and the resulting fragment was added to a phenol/chloroform solution and mixed to terminate the reaction. After the reaction mixture was centrifuged, the upper layer was collected, and DNA was collected by ethanol precipitation. Then, the DNA fragment of interest was separated by electrophoresis on an 0.8% agarose gel, and the DNA fragment of about 2.0 Kbp was collected by using EASY TRAP ver. 2 (DNA collection kit, manufactured by Takara Shuzo). The resulting DNA fragment was blunt-ended with a BKL kit (manufactured by Takara Shuzo) and phosphorylated.

The digestion product of pBHR1, and the dapA* and LysE24 gene region fragments prepared as described above were ligated by using a DNA Ligation Kit Ver. 2 (manufactured by Takara Shuzo). This ligation product was used to transform *Escherichia coli* (*E. coli* JM109 competent cells, manufactured by Takara Shuzo), and the cells were inoculated onto an LB agar medium containing 20 mg/L of kanamycin and incubated overnight at 37° C. The colonies that appeared on the agar medium were inoculated into an LB liquid medium containing 20 mg/L of kanamycin and cultured at 37° C. for 8 hours with shaking. Plasmid DNA was extracted from each culture medium by the alkali-SDS method, and the structure of each plasmid was confirmed by digestion with restriction enzymes and determination of the nucleotide sequence. A plasmid with identical transcription directions of the chloramphenicol resistance gene and the dapA* and lysE24 genes was selected as pBHR-EA.

A gentamicin resistant marker was introduced into pBHR-EA obtained as described above to construct the pBGEA plasmid. First, pBHR-EA was digested with the restriction enzyme NcoI, and the resulting fragment was added to a phenol/chloroform solution and mixed to terminate the reaction. After the reaction mixture was centrifuged, the upper layer was collected, and DNA was collected by ethanol precipitation. The resulting DNA fragment was blunt-ended by using a DNA Blunting kit (manufactured by Takara Shuzo). On the other hand, the gentamicin resistance gene region was amplified by PCR using pML122 (Monika Labes, Alfred Puhler, and Reinhard Simon, Gene, 89, (1990), 37-46) as the template DNA and pGm-f (SEQ ID NO: 17) and pGm-r (SEQ ID NO: 18) as primers, and PCR was performed under the following conditions: denaturation at 94° C. for 10 seconds, annealing at 60° C. for 30 seconds, and extension at 72° C. for 90 seconds. The PCR was performed using Pyrobest DNA polymerase (manufactured by Takara Shuzo). The resulting gentamicin resistance gene fragment was blunt-ended by using a BKL kit (manufactured by Takara Shuzo) and phosphorylated.

The digestion product of pBHR-EA and the gentamicin resistance gene region fragment prepared as described above were ligated by using a DNA Ligation Kit Ver. 2 (manufactured by Takara Shuzo). This ligation product was used to transform *Escherichia coli* (*E. coli* JM109 competent cells, manufactured by Takara Shuzo), and the cells were inoculated onto an LB agar medium containing 20 mg/L of gentamicin and incubated overnight at 37° C. The colonies that appeared on the agar medium were inoculated into an LB liquid medium containing 20 mg/L of gentamicin and cultured at 37° C. for 8 hours with shaking. Plasmid DNA was extracted from each culture medium by the alkali-SDS method, and the structure of each plasmid was confirmed by digestion with restriction enzymes and determination of the nucleotide sequence to obtain pBGEA. pBGEA was then introduced into the #403-11 strain prepared in Example 9, in which the lysE24 and dapA* genes had been incorporated into the chromosome, to enhance the lysE24 and dapA* genes. The strain was designated as #403-11/pBGEA. When #403-11/pBGEA and a control strain #403-11 were cultured in an SEII production medium containing 20 mg/L kanamycin, 50 mg/L gentamicin (the medium for the control strain contains no gentamicin), 0.075 g/L L-methionine, and 2.5 g/L sodium pyruvate, the amount of Lys was increased. The amount of Lys produced by the #403-11 strain was defined as 100, and the relative value of the amount of Lys produced by the #403-11/pBGEA strain was calculated and shown in Table 5. It was found that the introduction of the plasmid increased the amount of Lys produced by the #403-11 strain.

TABLE 5

| Name of strain | Relative amount of produced Lys (%) |
|---|---|
| #403-11 | 100 |
| #403-11/pBGEA | 111 |

Example 12

Construction of the pRSlysA, pRSddh, pRSdapB, pRSasd, and pRSask Plasmids, Introduction of the Plasmids into the #403-11/pBGEA Strain, and Evaluation of L-Lysine Productivity Next, expression plasmids carrying each Lys biosynthetic gene were constructed, and the plasmids were introduced into the #403-11/pBGEA strain, and the effects on L-lysine productivity were investigated.

<1> Construction of the pRSlysA Plasmid

The diaminopimelate decarboxylase gene (lysA) from *Methylophilus methylotrophus* was obtained by PCR using two oligonucleotide primers prepared based on a known sequence (SEQ ID NO: 13 in WO2000/061723) and using the chromosomal DNA of *Methylophilus methylotrophus* as the template. PCR was performed using plysA-f (SEQ ID NO: 19:) and plysA-r (SEQ ID NO: 20) as primers, under the following conditions for 25 cycles: denaturation at 94° C. for 20 seconds, annealing at 55° C. for 30 seconds, and extension at 72° C. for 60 seconds. The amplified lysA gene fragment from *M. methylotrophus* was digested with Sse8387I-XbaI, recognition sites of which had been added into the primer sequence, and the resulting fragment was ligated to pRStac (JP 2003-61687 A, U.S. Pat. No. 7,169,587) which had been digested with Sse8387I-XbaI. The plasmid was designated as pRSlysA.

<2> pRSddh

The diaminopimelate hydrogenase gene (ddh) from *Brevibacterium lactofermentum* was obtained by amplification with PCR using two kinds of oligonucleotide primers prepared based on the known nucleotide sequence of ddh based on *Corynebacterium glutamicum* (Ishino, S. et al. Nucleic acid res. 15, 3917 (1987)) and using the chromosomal DNA of *Brevibacterium lactofermentum* 2256 strain (ATCC 13869 strain) as the template. PCR was performed using pddh-f (SEQ ID NO: 21) and pddh-r (SEQ ID NO: 22) as primers, under the following conditions for 25 cycles: denaturation at 94° C. for 20 seconds, annealing at 55° C. for 30 seconds, and extension at 72° C. for 60 seconds. The amplified ddh gene fragment was digested with Sse8387I-XbaI, recognition sites of which had been added into the primer sequence, and the resulting fragment was ligated to pRStac (JP 2003-61687 A, U.S. Pat. No. 7,169,587) digested with Sse8387I-XbaI. The plasmid was designated as pRSddh.

<3> pRSdapB

The dihydrodipicolinate reductase gene (dapB) from *E. coli* was amplified by PCR using two oligonucleotide primers prepared based on the known nucleotide sequence and using the chromosomal DNA of *E. coli* as the template. PCR was performed using pdapB-f (SEQ ID NO: 23:) and pdapB-r (SEQ ID NO: 24) as primers, under the following conditions for 25 cycles: denaturation at 94° C. for 20 seconds, annealing at 55° C. for 30 seconds, and extension at 72° C. for 60 seconds. The amplified dapB gene fragment was digested with Sse8387I-XbaI, recognition sites of which had been added into the primer sequence, and the resulting fragment was ligated to pRStac (JP 2003-61687 A, U.S. Pat. No. 7,169, 587) which had been digested with Sse8387I-XbaI. The plasmid was designated as pRSdapB.

<4> pRSlasd

The aspartate-semialdehyde dehydrogenase gene (asd) from *E. coli* was amplified by PCR using two oligonucleotide primers prepared based on the known nucleotide sequence using the chromosomal DNA of *E. coli* as the template. PCR was performed using pasd-f (SEQ ID NO: 25) and pasd-r (SEQ ID NO: 26) as primers, under the following conditions for 25 cycles: denaturation at 94° C. for 20 seconds, annealing at 55° C. for 30 seconds, and extension at 72° C. for 60 seconds. The amplified ddh gene fragment was digested with Sse8387I-XbaI, recognition sites of which had been added into the primer sequence, and the resulting fragment was ligated to pRStac (JP 2003-61687 A, U.S. Pat. No. 7,169,587) which had been digested with Sse8387I-XbaI. The plasmid was designated as pRSasd.

<5> pRSask

The aspartokinase gene (ask) from *Methylophilus methylotrophus* was obtained by PCR using two oligonucleotide primers prepared based on a known sequence (SEQ ID NO: 5 in WO2000/061723) and using a chromosomal DNA of *Methylophilus methylotrophus* as a template. PCR was performed using pask-f (SEQ ID NO: 27:) and pask-r (SEQ ID NO: 28:) as primers. The following cycle was repeated 25 times: denaturation at 94° C. for 20 seconds, annealing at 55°

C. for 30 seconds, and extension at 72° C. for 90 seconds. The amplified ask gene fragment from *M. methylotrophus* was digested with Sse8387I-XbaI, recognition sites of which had been added into the primer and blunt-ended, and the resulting fragment was ligated to pRStac (JP 2003-61687 A, U.S. Pat. No. 7,169,587) which had been digested with Sse8387I and blunt-ended. The plasmid was designated as pRSask.

<6> Introduction and Evaluation of the Plasmids

The five plasmids prepared as described above were separately introduced into the #403-11/pBGEA strain prepared in Example 11, and the resulting strains were cultured in an SEII production medium containing 0.075 g/L L-methionine and 2.5 g/L sodium pyruvate. However, Lys productivity was not improved in all the strains. In the strain with ddh, Lys productivity was reduced.

Example 13

Enhancement of ddh+lysA in Combination, Construction of the pDA Plasmid, and Evaluation of Productivity of L-Lysine In order to determine the next limiting factor in Lys production using the #403-11 strain which was modified so that expression of the lysE24 and dapA* genes effective for improving Lys production in *M. methylotrophus* was sufficiently enhanced by gene incorporation and plasmid introduction, the genes were separately enhanced as shown in Example 12 to investigate the effects, but an effective gene was not determined. Therefore, various plasmids were constructed to enhance the genes in combination, each carrying two genes, and introduced into the #403-11 strain. As a result, it was found that enhancing lysA and ddh in combination improved productivity of L-lysine.

Diaminopimelate dehydrogenase encoded by ddh was thought to reversibly catalyze both the production and degradation reactions of diaminopimelic acid, and that enhancing ddh alone promoted not only production but also degradation of diaminopimelic acid. On the other hand, diaminopimelate decarboxylase which catalyzes the reaction subsequent to that of the diaminopimelate dehydrogenase is an irreversible enzyme that causes a decarboxylation reaction prior to L-lysine production. It was thought that enhancing both diaminopimelate dehydrogenase and diaminopimelate decarboxylase prevented degradation of diaminopimelic acid by diaminopimelate dehydrogenase and promoted synthesis of diaminopimelic acid.

Specifically, the pRSddh plasmid was digested with SapI, and the resulting fragment was blunt-ended and dephosphorylated to produce a vector, into which a PCR-amplified DNA fragment including the lysA gene region containing the tac promoter region. PCR amplification was performed using the pRSlysA plasmid as the template and ptac-f (SEQ ID NO: 29:) and plysA-r (SEQ ID NO: 20:) as primers. The following cycle was repeated 25 times: denaturation at 94° C. for 20 seconds, annealing at 55° C. for 30 seconds, and extension at 72° C. for 60 seconds. The resulting PCR-amplified fragment was digested with XbaI, and the resulting fragment was blunt-ended and ligated to the above-mentioned vector. In the resulting plasmid, the transcription directions of the ddh and lysA genes were identical, and the plasmid was designated as pDA. When a strain into which the pDA was introduced (#403-11/pBGEA/pDA) and the control strain #403-11/pBGEA were cultured in an SEII production medium containing 20 mg/L kanamycin, 50 mg/L gentamicin, and 50 mg/L streptomycin (the medium for the control strain contains no streptomycin), 0.075 g/L L-methionine, and 2.5 g/L sodium pyruvate, the amount of Lys increased. The amount of Lys produced by the #403-11/pBGEA strain was defined as 100, and the relative value of the amount of Lys produced by the #403-11/pBGEA/pDA strain was calculated and shown in Table 6.

TABLE 6

| Name of strain | Relative amount of produced Lys (%) |
|---|---|
| #403-11/pBGEA | 100 |
| #403-11/pBGEA/pDA | 120 |

Example 14

Enhancement of Further L-Lysine Biosynthetic Genes in Combination, Construction of pBDAS (lysA+ddh+dapB+asd), and Evaluation of L-Lysine Productivity It was found that the L-lysine productivity was improved by enhancing the ddh and lysA genes in combination, since these genes are capable of catalyzing two sequential reactions in the biosynthesis pathway. The effect of enhancing other enzyme genes in combination with ddh+lysA was investigated and it was found that the use of dapB and asd in combination with ddh and lysA improved L-lysine production.

Specifically, the pRSdapB plasmid was digested with EcoRI, and the resulting fragment was blunt-ended and dephosphorylated to prepare a vector. The plasmid pDA was digested with HpaI-SapI, and the resulting DNA fragment of 2.5 kbp, which includes lysA and ddh which each have a tac promoter upstream of the genes, was collected and blunt-ended to be ligated to the vector, to thereby construct pBDA. The plasmid was found to have the ddh and lysA genes inserted upstream of dapB so that the direction of ddh and lysA and the direction of dapB were identical. The pBDA plasmid was further digested with SapI, and the resulting fragment was blunt-ended and dephosphorylated to prepare a vector. A PCR-amplified DNA fragment including the asd gene region containing a tac promoter region was then inserted into the vector. PCR amplification was performed using the pRSasd plasmid as the template and ptac-f and pasd-r as primers. The following cycle was repeated 25 times: denaturation at 94° C. for 20 seconds, annealing at 55° C. for 30 seconds, and extension at 72° C. for 90 seconds. The resulting PCR-amplified fragment was blunt-ended and phosphorylated, and the fragment was ligated to the above-mentioned vector. The resulting plasmid was designated as pBDAS. When a strain into which the pBDAS plasmid was introduced (#403-11/pBGEA/pBDAS) and a control strain #403-11/pBGEA were cultured in an SEII production medium containing 20 mg/L kanamycin, 50 mg/L gentamicin, and 50 mg/L streptomycin (the medium for the control strain contains no streptomycin), 0.075 g/L L-methionine, and 2.5 g/L sodium pyruvate, the amount of Lys increased. The amount of Lys produced by the #403-11/pBGEA strain was defined as 100, and the relative value of the amount of Lys produced by the #403-11/pBGEA/pBDAS strain was calculated and is shown in Table 7.

TABLE 7

| Name of strain | Relative amount of produced Lys (%) |
|---|---|
| #403-11/pBGEA | 100 |
| #403-11/pBGEA/pDA | 120 |
| #403-11/pBGEA/pBDAS | 143 |

Example 15

Construction of pCBDAS (lysA+ddh+dapB+asd+lysC), Introduction of the Plasmid into the #403-11/pBGEA Strain, and Evaluation of L-Lysine Productivity There was not a restriction site suitable for introduction of an additional biosynthetic gene into the pBDAS plasmid, and it was difficult to insert an additional gene Therefore, genes of interest were cloned into the pMW119 vector and cleaved. First, the pMW119 vector was digested with XbaI, and the resulting fragment was ligated to a DNA fragment having Ptac+dapB which had been obtained by cleaving pRSdapB with XbaI. Subsequently, the plasmid was digested with BamHI, and the resulting fragment was blunt-ended and dephosphorylated to prepare a vector, which was then ligated to a DNA fragment having Ptac+ddh+Ptac+lysA obtained by cleaving the pDA plasmid with HapI-SapI. The plasmid was digested with SmaI, and the resulting fragment was dephosphorylated to prepare a vector, which was then ligated to a DNA fragment having Ptac+asd prepared in the same way as Example 14. The plasmid constructed as described above was designated as pMWBDAS. In the plasmid, the directions of ddh, lysA, and asd were identical, while the direction of dapB was the opposite. The dapB, ddh, lysA, and asd genes are located on pMW119 in the stated order from the direction of the lac promoter. When the plasmid is digested with SalI-SacI, a fragment containing dapB, ddh, lysA, and asd each containing a tac promoter is obtained. The above-mentioned pRSask plasmid was digested with SapI and blunt-ended, and the fragment was ligated thereto, to thereby construct pCBDAS. When a strain into which the pCBDAS plasmid was introduced (#403-11/pBGEA/pCBDAS) was cultured in an SEII production medium containing 20 mg/L kanamycin, 50 mg/L gentamicin, 50 mg/L streptomycin (the medium for the control strain contains no streptomycin), 0.075 g/L L-methionine, and 2.5 g/L sodium pyruvate and supplemented with ammonium sulfate to a final concentration of 6 g/L, the amount of Lys which was produced was increased. The amount of Lys produced by the #403-11/pBGEA strain was defined as 100, and the relative value of the amount of Lys produced by the #403-11/pBGEA/pBDAS strain was calculated and shown in Table 8.

TABLE 8

| Name of strain | Relative amount of produced Lys (%) |
|---|---|
| #403-11/pBGEA | 100 |
| #403-11/pBGEA/pDA | 120 |
| #403-11/pBGEA/pBDAS | 143 |
| #403-11/pBGEA/pCBDAS | 160 |

Example 16

Construction of the Transfer Unit for Reconstruction of a Producing Bacterium Capable of Eliminating the Drug-Resistant Marker (V12Sα), and Construction of the V12Sα Strain (lysE24+dapA* Gene-Amplified Strain)

Next, a method of producing a strain containing no antibiotic-resistant gene marker and carrying Lys biosynthetic genes in the chromosome will be described. The pMIV-FRT-KmFRT plasmid (see Example 6) was digested with SmaI, and the PCR-amplified lysE+dapA* fragment was inserted. The lysE+dapA* fragment was obtained by the method shown in Example 6. The resulting plasmid was designated as pMIV-FRTKmFRT-EA. The plasmid has a drug-resistant gene different from that of pMIV-FRTGmFRT-EA.

First, the pAET7 plasmid described in Example 1 was introduced into a wild-type strain of M. methylotrophus AS1 (NCIMB10515), and a transformant was selected in an SEII agar medium containing 50 mg/L streptomycin. The pMIV-FRTKmFRT-EA plasmid was introduced into the strain by electroporation in accordance with the method described in Example 2, and strains to which the mini-Mu cassette (EA unit) including the lysE24+dapA* genes was transferred to the chromosome were selected in an SEII agar medium containing 50 mg/L streptomycin and 20 mg/L kanamycin. From the strains, 200 strains were selected randomly and inoculated on SEII plates containing 50 mg/L streptomycin and 20 mg/L kanamycin, followed by culturing at 37° C. overnight. Then, bacterial cells present on the medium surface of about 0.3 square centimeters were scraped off and inoculated into an SEII production medium (5 ml) containing 50 mg/l streptomycin and 20 mg/L kanamycin, and the cells were cultured with shaking at 37° C. for 34 hours. After completion of culture, the bacterial cells were removed by centrifugation, and the concentration of L-lysine in each culture supernatant was measured using a Biotech-analyzer AS-210 (manufactured by Sakura Seiki Co., Ltd.) to select the strain having the highest concentration of L-lysine. The strain was designated as V1. Transfer was repeated 12 times in the same way as Example 3 to obtain the V12 strain. The amount of Lys produced by V1 was defined as 100, and the relative value of the amount of Lys produced by the V12 strain was calculated and shown in Table 9.

TABLE 9

| Name of strain | Relative amount of produced Lys (%) |
|---|---|
| V1 | 100 |
| V12 | 1066 |

Next, the transfer site of the mini-Mu cassette on the chromosome of the V12 strain was determined in accordance with the same method as in Example 4. Based on the information, it is possible to construct a strain identical to the V12 strain.

Subsequently, the pFLP31 plasmid (see Example 9) was introduced into the V12 strain, and the kanamycin-resistant gene region was eliminated from the mini-Mu cassette on the chromosome by the method described in Example 9. The kanamycin-sensitive strain obtained by the above-mentioned procedure was designated as V12Sα. The V12Sα was designated as AJ110196, and the strain was deposited under the provisions of Budapest Treaty at the National Institute of Advanced Industrial Science and Technology, International Patent Organism Depositary (Tsukuba Central 6, 1-1, Higashi 1-Chome, Tsukuba-shi, Ibaraki-ken, 305-5466, Japan) on Oct. 12, 2005 and received the accession number FERM BP-10434.

Example 17

Construction of the lysE24+dapA*+lysA+ddh+ dapB+asd+lysC Transfer Unit

As shown in Example 15, it was found that enhancing various Lys biosynthetic genes, in addition to enhancing lysE24+dapA*, improved the production of Lys, so a plasmid for incorporating these genes into the chromosome was constructed. First, pMIV-FRTKmFRT was digested with EcoRI, and the resulting fragment was blunt-ended and dephosphorylated, followed by insertion of the PCR-amplified lysE24+dapA* fragment to construct pMIV-FRTKmFRT-EA#1. The plasmid was digested with SmaI, and the resulting fragment was dephosphorylated to prepare a vector, followed by the insertion of the PCR-amplified Ptac+dapB fragment. PCR amplification was performed using the pRSdapB plasmid as the template and ptac-f and pdapB-r as primers, and was repeated for 25 cycles: denaturation at 94° C. for 20 seconds, annealing at 55° C. for 30 seconds, and extension at 72° C. for 90 seconds. The PCR-amplified fragment was blunt-ended and phosphorylated to be ligated to the above-mentioned vector to obtain pMIV-FRTKmFRT-EAB#1. The transcription directions of the dapA and dapB genes were identical. Then, the plasmid was digested with HindIII, and the resulting fragment was blunt-ended and dephosphorylated, which was then ligated to a DNA fragment including lysA and ddh obtained by the method described in Example 14 to obtain pMIV-FRTKmFRT-EABDA#12. The transcription direction of the ddh gene was opposite to that of dapA and dapB. The plasmid was digested with SalI, and the resulting fragment was blunt-ended and dephosphorylated, followed by insertion of a DNA fragment including the asd gene region containing the tac promoter region which had been prepared by the method described in Example 14. In this procedure, the asd fragment was inserted into the blunt-ended fragment, and therefore, a plasmid where two asd fragments were inserted was obtained and designated as pMIV-FRTKmFRT-EABDAS#10. The directions of both the asd genes were opposite to that of dapA and dapB. In the resulting pMIV-FRTKmFRT-EABDAS#10, the genes lysE, dapA, dapB, asd, asd, lysA, and ddh were located in the stated order. As described above, a plasmid for transferring a gene cassette containing the six genes to the chromosome was constructed.

Example 18

Construction of lysE24+dapA*+lysA+ddh+dapB+asd+lysC-Amplified Strains (Vmac3 Strain, Vmac3S Strain) and Evaluation of L-Lysine Productivity pAET7 was introduced into V12Sα obtained in Example 16, and the pMIV-FRTKmFRT-EABDAS#10 plasmid was also introduced to obtain the V12Sα strains where the lysE, dapA, dapB, asd, lysA, and ddh genes were introduced into the chromosome by the method described in Example 16. Randomly selected 200 strains were cultured in an SEII production medium containing 50 mg/L streptomycin and 20 mg/L kanamycin to select a strain which produced the most L-lysine, and was designated as Vmac1. A streptomycin-sensitive strain was selected form the Vmac1 strains to obtain a strain where pAET7 was eliminated. The pFLP31 plasmid shown in Example 9 was introduced into the strain, and a kanamycin-resistant gene region was eliminated from the mini-Mu cassette on the chromosome by the method described in Example 9. The kanamycin-sensitive strains obtained by the procedure were designated as Vmac1S strain. A streptomycin-sensitive strain was selected from the Vmac1S strain to obtain a strain where the pFLP31 plasmid was eliminated. The pAET7 plasmid was introduced again into this strain, and the plasmid pMIV-FRTKmFRT-EABDAS#10 was also introduced again. Then, the strain which produced the most L-lysine was selected and designated as the Vmac2 strain. In the same way as described above, the Vmac2S strain, Vmac3 strain, and Vmac3S strain were obtained. The amount of Lys produced by V12 was defined as 100, and the relative value of the amount of Lys produced by the Vmac3S strain was calculated and shown in Table 10.

TABLE 10

| Name of strain | Relative amount of produced Lys (%) |
|---|---|
| V12 | 100 |
| V12Sα | 100 |
| Vmac3S | 188 |

Example 19

Impartation of L-Met Auxotrophy by Deletion of metF, Construction of the V3E2F Strain, and Evaluation of L-Lysine Productivity The amount of produced L-lysine was further increased by introducing the pBGEA plasmid into the Vmac3S strain. Also, lysE24+dapA* was effective to increase the yield of L-lysine in the Vmac3S strain, and therefore, a mini-Mu cassette of lysE24+dapA* was incorporated into the chromosome again. Specifically, pAET7 was introduced into the Vmac3S strain, and the pMIV-FRTKmFRT-EA plasmid was introduced. The strain was cultured in an SEII agar medium containing 50 mg/L streptomycin and 20 mg/L kanamycin to select Vmac3S strains where lysE24+dapA* was incorporated in the chromosome. Randomly selected 200 strains were cultured in an SEII production medium containing 50 mg/L streptomycin and 20 mg/L kanamycin to select a strain which produced the most L-lysine, which was designated as Vmac3EA. Transfer was repeated three times in accordance with the same method as in Example 3, and the strains which produced the most lysine was selected and designated as the V3E2 strain. An antibiotic-resistant marker was eliminated from the strain by the above-mentioned method to produce a kanamycin-sensitive strain, which was designated as V3E2S.

Next, L-methionine auxotrophy was imparted to VAE#8, to improve L-lysione production. Specifically, three PCR-amplified DNA fragments with overlapping regions were mixed, and the mixture was used as the template to perform PCR again, to prepare a DNA fragment for gene disruption, where a kanamycin-resistant gene was inserted into nearly the center of the target gene. A fragment 1 (N-terminal side fragment) was amplified by PCR using a chromosomal DNA of M. methylotrophus AS1 strain as the template and metF-fn1 (SEQ ID NO: 30) and metF-rn (SEQ ID NO: 32) as primers. PCR was performed under the following conditions for 25 cycles: denaturation at 94° C. for 30 seconds, annealing at 60° C. for 30 seconds, and extension at 72° C. for 30 seconds. In the same way as described above, a fragment 2 (C-terminal side fragment) was amplified by PCR using the chromosomal DNA of M. methylotrophus AS1 strain as the template and metF-rc1 (SEQ ID NO: 33) and metF-fc (SEQ ID NO: 35) as primers. PCR was performed under the following conditions for 25 cycles: denaturation at 94° C. for 30 seconds, annealing at 60° C. for 30 seconds, and extension at 72° C. for 30 seconds. The fragment 3 (Km-resistant gene fragment) amplified by PCR using the pKD4 plasmid as the template and pKD-Kmf (SEQ ID NO: 36) and pKD-KmGmr (SEQ ID NO: 37) as primers. PCR was performed under the following conditions for 25 cycles: denaturation at 94° C. for 30 seconds, annealing at 60° C. for 30 seconds, and extension at 72° C. for 30 seconds. The fragments 1 and 2 were separated in a 1% low-melting-point agarose gel and purified by Wizard PCR Preps DNA purification system manufactured by Promega. The concentrations of the fragments were measured, and PCR was performed using a mixture of the fragments 1, 2, and 3 at a concentration ratio of 2:2:1 as the template and metF-fn2 (SEQ ID NO: 31) and metF-rc2 (SEQ ID NO: 34) as primers. PCR was performed under the following conditions for 25 cycles: denaturation at 98° C. for 20 seconds and extension at 68° C. for 3 minutes. In this amplification, LA taq polymerase (Takara Bio Inc.) was used. The amplified DNA fragment has a kanamycin-resistant gene inserted into nearly the center of the gene fragment containing the metF gene. About 3 micrograms of the DNA fragment were prepared and introduced into the V3E2S strain by electroporation. Recovery culture was performed in an SEII liquid medium containing 0.4 g/L L-methionine, and the cells were inoculated onto an SEII agar medium containing 20 mg/L kanamycin, 0.4 g/L L-methionine, and 2.5 g/L sodium pyruvate. A strain which could not grow on an SEII agar medium containing no L-methionine, that is, a strain auxotrophic for L-methionine, was selected and designated as V3E3F. When the strain was cultured in an SEII production medium containing 0.075 g/L L-methionine and 2.5 g/L sodium pyruvate and supplemented with ammonium sulfate to a final concentration of 6 g/L, the amount of Lys produced was increased. The amount of Lys produced by Vmac3S was defined as 100, and the relative value of the amount of Lys produced by the V3E2F strain was calculated and shown in Table 11. The increase in the amount of L-lysine was thought to be caused by the decrease in the amount of cells due to the L-methionine auxotrophy. Table 12 shows the dapA activities of the wild-type strain and the V3E2F strain.

TABLE 11

| Name of strain | Relative amount of produced Lys (%) |
|---|---|
| Vmac3S | 100 |
| V3E2 | 128 |
| V3E2F | 150 |

TABLE 12

| Name of bacterium | Specific activity (milliunit/milligram protein) |
|---|---|
| AS1 | 12 |
| V3E2F | 188 |

The amount of an enzyme that produces 1 micromol of a product per minute was defined as 1 unit.

Example 20

Construction of the pBG-lysC Plasmid, Construction of the V3E2F/pBGlysC Strain, and Evaluation of L-Lysine Productivity Although the above-mentioned studies reveal that enhancing aspartokinase activity in M. methylotrophus can improve L-lysine productivity, as shown in Example 15, enhancing wild-type AK derived from M. methylotrophus has been performed so far. However, the activity of aspartokinase encoded by the ask gene is subject to feedback inhibition by L-lysine and L-threonine. In order to improve L-lysine productivity, it is desirable that the activity is not subject to feedback inhibition by L-lysine and L-threonine. Therefore, a mutant AKIII which is derived from E. coli and is not subject to feedback inhibition by L-lysine was prepared. A mutant lysC gene encoding a mutant AKIII that is desensitized to feedback inhibition by L-lysine was prepared by PCR using two oligonucleotide primers designed based on the known sequence and RSFD80 (WO95/16042, U.S. Pat. No. 6,040,160) as the template. Primers used were plysC-f (SEQ ID NO: 38:) and plysC-r (SEQ ID NO 39), and PCR was performed under the following conditions for 25 cycles: denaturation at 94° C. for 20 seconds, annealing at 55° C. for 30 seconds, and extension at 72° C. for 90 seconds. The resulting product was digested with Sse8387I and SapI, and this fragment was ligated to a fragment obtained by digesting pRStac (JP 2003-61687 A) with Sse83871-SapI. The obtained plasmid was designated as pRSlysC*. Next, the pRSlysC* was digested with EcoRI-SapI to excise the lysC* fragment containing the tac promoter sequence, and the resulting product was ligated to a fragment obtained by digesting pBHR1 with the DraI restriction enzyme followed by blunt-ending and dephosphorylation. The plasmid was designated as pBHR-lysC. It was digested with NcoI, and the resulting fragment was blunt-ended and dephosphorylated to obtain a vector, into which a gentamicin-resistant gene fragment prepared in the same way as in Example 11, was inserted to construct the pBGlysC plasmid. When the pBGlysC plasmid was introduced into the V3E2F strain prepared in Example 19, the amount of L-lysine produced was increased. Moreover, when pRSlysEdapA (see JP 2003-61687 A) was introduced into the V3E2F/pBGlysC strain, the amount of L-lysine produced was increased. When the V3E2F/pBGlysC and V3E2F/pBGlysC/pRSlysEdapA strains were each cultured in an SEII production medium containing 50 mg/L gentamicin, 50 mg/L streptomycin (the medium for the control strain contained neither gentamicin nor streptomycin), 0.08 g/L L-methionine, and 2.5 g/L sodium pyruvate and supplemented with ammonium sulfate to a final concentration of 6 g/L, the amount of Lys produced was increased. The amount of Lys produced by V3E2F was defined as 100, and the relative values of the amounts of Lys produced by V3E2F/pBGlysC and V3E2F/pBGlysC/pRSlysEdapA strains were calculated and shown in Table 13.

TABLE 13

| Name of strain | Relative amount of produced Lys (%) |
|---|---|
| V3E2F | 100 |
| V3E2F/pBGlysC | 115 |
| V3E2F/pBGlysC/pRSlysEdapA | 132 |

INDUSTRIAL APPLICABILITY

According to the present invention, L-lysine productivity by a methanol-assimilating bacterium is improved.

The invention claimed is:

1. A methanol-assimilating bacterium comprising:
   a DNA encoding dihydrodipicolinate synthase which is desensitized to feedback inhibition by L-lysine; and
   a DNA encoding a LysE protein which has been mutated to promote the export of L-lysine to the outside of said methanol-assimilating bacterium,
   wherein said bacterium is modified to enhance the intracellular activities of diaminopimelate dehydrogenase, diaminopimelate decarboxylase, dihydrodipicolinate reductase, and aspartate-semialdehyde dehydrogenase, wherein the DNA encoding dihydrodipicolinate synthase, the DNA encoding dihydrodipicolinate reductase, and the DNA encoding aspartate-semialdehyde dehydrogenase are from *Escherichia coli*, the DNA encoding diaminopimelate decarboxylase is from *Methylophilus methylotrophus*, and the DNA encoding diaminopimelate dehydrogenase and the DNA encoding LysE are from *Brevibacterium lactofermentum*.

2. The methanol-assimilating bacterium according to claim 1, further comprising:
   a DNA encoding aspartokinase which is desensitized to feedback inhibition by L-lysine, wherein the DNA encoding aspartokinase is from *Escherichia coli*.

3. The methanol-assimilating bacterium according to claim 1, wherein the DNAs are introduced in the bacterium by a method selected from the group consisting of
   i) introduction of said DNAs into the chromosomal DNA of said bacterium, and
   ii) transformation of the bacterium with a plasmid(s) carrying said DNAs, and
   iii) combinations thereof.

4. The methanol-assimilating bacterium according to claim 1, wherein said bacterium belongs to the genus *Methylophilus*.

5. The methanol-assimilating bacterium according to claim 1, wherein said bacterium is *Methylophilus methylotrophus* AJ110196 (FERM BP-10434).

6. A method of producing L-lysine comprising
   culturing the methanol-assimilating bacterium according to claim 1 in a medium; and
   collecting L-lysine from the medium or the bacterium.

7. The method of producing L-lysine according to claim 6, wherein the main carbon source in the medium is methanol.

8. *Methylophilus methylotrophus* AJ110196 (FERM BP-10434).

9. The methanol-assimilating bacterium according to claim 1, wherein said dihydrodipicolinate synthase is a protein having at least 95% homology to the entire amino acid sequence of SEQ ID NO: 41, and includes replacement of the histidine residue at position 118 of SEQ ID NO: 41 with a tyrosine residue.

10. The methanol-assimilating bacterium according to claim 1, wherein said LysE protein has not less than 95% homology to the entire amino acid sequence of SEQ ID NO: 51 and can promote export of L-lysine to the outside of a methanol-assimilating bacterium when it is introduced into a methanol-assimilating bacterium.

11. The methanol-assimilating bacterium according to claim 1, wherein said LysE protein has not less than 95% homology to SEQ ID NO: 55, and includes replacement of the glycine residue at position 56 with another amino acid residue, and can promote export of L-lysine to the outside of a methanol-assimilating bacterium when it is introduced into a methanol-assimilating bacterium.

12. The methanol-assimilating bacterium according to claim 1, wherein said DNA encoding the LysE protein is able to hybridize with a complementary strand of the nucleotide sequence of SEQ ID NO: 56 under stringent conditions comprising washing at 60° C. with 0.1×SSC and 0.1% SDS, and encodes a protein having activity for promoting export of L-lysine to the outside of a methanol-assimilating bacterium when it is introduced into a methanol-assimilating bacterium.

13. The methanol-assimilating bacterium according to claim 1, wherein said diaminopimelate dehydrogenase is a protein having not less than 95% homology to the entire amino acid sequence of SEQ ID NO: 53.

14. The methanol-assimilating bacterium according to claim 1, wherein said diaminopimelate decarboxylase is a protein having not less than 95% homology to the entire amino acid sequence of SEQ ID NO: 49.

15. The methanol-assimilating bacterium according to claim 1, wherein said dihydrodipicolinate reductase is a protein having not less than 95% homology to the entire amino acid sequence of SEQ ID NO: 43.

16. The methanol-assimilating bacterium according to claim 1, wherein said aspartate-semialdehyde dehydrogenase is a protein having not less than 95% homology to the entire amino acid sequence of SEQ ID NO: 45.

17. The methanol-assimilating bacterium according to claim 2, wherein said aspartokinase is a protein having not less than 95% homology to the entire amino acid sequence of SEQ ID NO: 47, and includes replacement of the threonine residue at position 352 with an isoleucine residue.

* * * * *

SEQUENCE LISTING

<160> NUMBER OF SEQ ID NOS: 59

<210> SEQ ID NO 1
<211> LENGTH: 25
<212> TYPE: DNA
<213> ORGANISM: Artificial sequence
<220> FEATURE:
<223> OTHER INFORMATION: primer

<400> SEQUENCE: 1
aaaaagctta acacagaaaa aagcc                                    25

<210> SEQ ID NO 2
<211> LENGTH: 28
<212> TYPE: DNA
<213> ORGANISM: Artificial sequence
<220> FEATURE:
<223> OTHER INFORMATION: primer

<400> SEQUENCE: 2
aaactgcagt ggtcgaaaaa aaaagccc                                 28

<210> SEQ ID NO 3
<211> LENGTH: 23
<212> TYPE: DNA
<213> ORGANISM: Artificial sequence
<220> FEATURE:
<223> OTHER INFORMATION: primer

<400> SEQUENCE: 3
aaagaattcg agctcggtac ctc                                      23

<210> SEQ ID NO 4
<211> LENGTH: 23
<212> TYPE: DNA
<213> ORGANISM: Artificial sequence
<220> FEATURE:
<223> OTHER INFORMATION: primer

<400> SEQUENCE: 4
aaaaagcttg catgcaggcc tct                                      23

<210> SEQ ID NO 5
<211> LENGTH: 21
<212> TYPE: DNA
<213> ORGANISM: Artificial sequence
<220> FEATURE:
<223> OTHER INFORMATION: primer

<400> SEQUENCE: 5
aaaggatccg catgccgttg a                                        21

<210> SEQ ID NO 6
<211> LENGTH: 93
<212> TYPE: DNA
<213> ORGANISM: Artificial sequence
<220> FEATURE:
<223> OTHER INFORMATION: primer

<400> SEQUENCE: 6
aaagaattcc gatacaatta aaggctcctt ttggagcctt tttttggag attttcaacg    60 tgaaaaaatt attattcgca attccaagct aat                           93

<210> SEQ ID NO 7

```
<211> LENGTH: 36
<212> TYPE: DNA
<213> ORGANISM: Artificial sequence
<220> FEATURE:
<223> OTHER INFORMATION: primer

<400> SEQUENCE: 7
cattctagat ccctaaactt tacagcaaac cggcat                                36

<210> SEQ ID NO 8
<211> LENGTH: 22
<212> TYPE: DNA
<213> ORGANISM: Artificial sequence
<220> FEATURE:
<223> OTHER INFORMATION: primer

<400> SEQUENCE: 8
cacagagaca tattgcccgt tg                                               22

<210> SEQ ID NO 9
<211> LENGTH: 29
<212> TYPE: DNA
<213> ORGANISM: Artificial sequence
<220> FEATURE:
<223> OTHER INFORMATION: primer

<400> SEQUENCE: 9
catctgtttc atttgaagcg cgaaagcta                                        29

<210> SEQ ID NO 10
<211> LENGTH: 21
<212> TYPE: DNA
<213> ORGANISM: Artificial sequence
<220> FEATURE:
<223> OTHER INFORMATION: primer

<400> SEQUENCE: 10
cgccagccag gacagaaatg c                                                21

<210> SEQ ID NO 11
<211> LENGTH: 22
<212> TYPE: DNA
<213> ORGANISM: Artificial sequence
<220> FEATURE:
<223> OTHER INFORMATION: primer

<400> SEQUENCE: 11
gtccagcggt ttttcttggg ct                                               22

<210> SEQ ID NO 12
<211> LENGTH: 29
<212> TYPE: DNA
<213> ORGANISM: Artificial sequence
<220> FEATURE:
<223> OTHER INFORMATION: primer

<400> SEQUENCE: 12
catctgtttc atttgaagcg cgaaagcta                                        29

<210> SEQ ID NO 13
<211> LENGTH: 57
<212> TYPE: DNA
<213> ORGANISM: Artificial sequence
<220> FEATURE:
<223> OTHER INFORMATION: primer

<400> SEQUENCE: 13
```

```
aattcgagct cggtacccgg ggatcctcta gagtcgacct gcaggcatgc aagctta        57

<210> SEQ ID NO 14
<211> LENGTH: 57
<212> TYPE: DNA
<213> ORGANISM: Artificial sequence
<220> FEATURE:
<223> OTHER INFORMATION: primer

<400> SEQUENCE: 14
gatctaagct tgcatgcctg caggtcgact ctagaggatc cccgggtacc gagctcg        57

<210> SEQ ID NO 15
<211> LENGTH: 30
<212> TYPE: DNA
<213> ORGANISM: Artificial sequence
<220> FEATURE:
<223> OTHER INFORMATION: primer

<400> SEQUENCE: 15
ctatgatcat ttgcctggcg gcagtagcgc                                       30

<210> SEQ ID NO 16
<211> LENGTH: 31
<212> TYPE: DNA
<213> ORGANISM: Artificial sequence
<220> FEATURE:
<223> OTHER INFORMATION: primer

<400> SEQUENCE: 16
cttagatctc aaaaagagtt tgtagaaacg c                                     31

<210> SEQ ID NO 17
<211> LENGTH: 21
<212> TYPE: DNA
<213> ORGANISM: Artificial sequence
<220> FEATURE:
<223> OTHER INFORMATION: primer

<400> SEQUENCE: 17
cgccagccag gacagaaatg c                                                21

<210> SEQ ID NO 18
<211> LENGTH: 22
<212> TYPE: DNA
<213> ORGANISM: Artificial sequence
<220> FEATURE:
<223> OTHER INFORMATION: primer

<400> SEQUENCE: 18
gtccagcggt ttttcttggg ct                                               22

<210> SEQ ID NO 19
<211> LENGTH: 39
<212> TYPE: DNA
<213> ORGANISM: Artificial sequence
<220> FEATURE:
<223> OTHER INFORMATION: primer

<400> SEQUENCE: 19
aaacccgggg atcctgagcg ccaatacccT caaacgcct                             39

<210> SEQ ID NO 20
<211> LENGTH: 43
<212> TYPE: DNA
<213> ORGANISM: Artificial sequence
<220> FEATURE:
```

<223> OTHER INFORMATION: primer

<400> SEQUENCE: 20
tttcccgggc ttggcggctt cggttttttt attaggggtt gcc         43

<210> SEQ ID NO 21
<211> LENGTH: 41
<212> TYPE: DNA
<213> ORGANISM: Artificial sequence
<220> FEATURE:
<223> OTHER INFORMATION: primer

<400> SEQUENCE: 21
acccctgcag ggccaccaca attttggagg attacaagaa c         41

<210> SEQ ID NO 22
<211> LENGTH: 33
<212> TYPE: DNA
<213> ORGANISM: Artificial sequence
<220> FEATURE:
<223> OTHER INFORMATION: primer

<400> SEQUENCE: 22
tcctctagac tcgagctaaa ttagacgtcg cgt         33

<210> SEQ ID NO 23
<211> LENGTH: 35
<212> TYPE: DNA
<213> ORGANISM: Artificial sequence
<220> FEATURE:
<223> OTHER INFORMATION: primer

<400> SEQUENCE: 23
gcgcctgcag gcgctggtta ctctgaaaac ggtct         35

<210> SEQ ID NO 24
<211> LENGTH: 46
<212> TYPE: DNA
<213> ORGANISM: Artificial sequence
<220> FEATURE:
<223> OTHER INFORMATION: primer

<400> SEQUENCE: 24
gcatctagag acaatttaaa aacataacac caaaaataaa agggcc         46

<210> SEQ ID NO 25
<211> LENGTH: 40
<212> TYPE: DNA
<213> ORGANISM: Artificial sequence
<220> FEATURE:
<223> OTHER INFORMATION: primer

<400> SEQUENCE: 25 gccctgcag gccggcacat ttatacagca cacatctttg         40

<210> SEQ ID NO 26
<211> LENGTH: 35
<212> TYPE: DNA
<213> ORGANISM: Artificial sequence
<220> FEATURE:
<223> OTHER INFORMATION: primer

<400> SEQUENCE: 26
taatctagaa agattacgcc agttgacgaa gcatc         35

<210> SEQ ID NO 27

-continued

```
<211> LENGTH: 40
<212> TYPE: DNA
<213> ORGANISM: Artificial sequence
<220> FEATURE:
<223> OTHER INFORMATION: primer

<400> SEQUENCE: 27
agggaattct aaaccggata tggcgatggc aggtggtact                           40

<210> SEQ ID NO 28
<211> LENGTH: 39
<212> TYPE: DNA
<213> ORGANISM: Artificial sequence
<220> FEATURE:
<223> OTHER INFORMATION: primer

<400> SEQUENCE: 28
taactgcagg aagttttaat agtaccaaca cagcgcatg                            39

<210> SEQ ID NO 29
<211> LENGTH: 39
<212> TYPE: DNA
<213> ORGANISM: Artificial sequence
<220> FEATURE:
<223> OTHER INFORMATION: primer

<400> SEQUENCE: 29
aaaagatctc ccgttctgga taatgttttt tgcgccgac                            39

<210> SEQ ID NO 30
<211> LENGTH: 20
<212> TYPE: DNA
<213> ORGANISM: Artificial sequence
<220> FEATURE:
<223> OTHER INFORMATION: primer

<400> SEQUENCE: 30
tggactgacg gtggctactc                                                 20

<210> SEQ ID NO 31
<211> LENGTH: 18
<212> TYPE: DNA
<213> ORGANISM: Artificial sequence
<220> FEATURE:
<223> OTHER INFORMATION: primer

<400> SEQUENCE: 31
gaccacgtca ttttccct                                                   18

<210> SEQ ID NO 32
<211> LENGTH: 58
<212> TYPE: DNA
<213> ORGANISM: Artificial sequence
<220> FEATURE:
<223> OTHER INFORMATION: primer

<400> SEQUENCE: 32
ccagcctaca caatcgctca agacgtgtaa tgcacttccg gatgaaactc agggtaag       58

<210> SEQ ID NO 33
<211> LENGTH: 19
<212> TYPE: DNA
<213> ORGANISM: Artificial sequence
<220> FEATURE:
<223> OTHER INFORMATION: primer

<400> SEQUENCE: 33
```

-continued tgccaaatac gggctactg                                                    19

<210> SEQ ID NO 34
<211> LENGTH: 18
<212> TYPE: DNA
<213> ORGANISM: Artificial sequence
<220> FEATURE:
<223> OTHER INFORMATION: primer

<400> SEQUENCE: 34
tccgggctca attcactc                                                     18

<210> SEQ ID NO 35
<211> LENGTH: 53
<212> TYPE: DNA
<213> ORGANISM: Artificial sequence
<220> FEATURE:
<223> OTHER INFORMATION: primer

<400> SEQUENCE: 35
gagaatagga acttcggaat aggaactaag gaggagctgg ttgcgtttac gtc              53

<210> SEQ ID NO 36
<211> LENGTH: 30
<212> TYPE: DNA
<213> ORGANISM: Artificial sequence
<220> FEATURE:
<223> OTHER INFORMATION: primer

<400> SEQUENCE: 36
gcattacacg tcttgagcga ttgtgtaggc                                        30

<210> SEQ ID NO 37
<211> LENGTH: 34
<212> TYPE: DNA
<213> ORGANISM: Artificial sequence
<220> FEATURE:
<223> OTHER INFORMATION: primer

<400> SEQUENCE: 37
cctccttagt tcctattccg aagttcctat tctc                                   34

<210> SEQ ID NO 38
<211> LENGTH: 35
<212> TYPE: DNA
<213> ORGANISM: Artificial sequence
<220> FEATURE:
<223> OTHER INFORMATION: primer

<400> SEQUENCE: 38
gaacctgcag gccctgacac gaggtagatt atgtc                                  35

<210> SEQ ID NO 39
<211> LENGTH: 55
<212> TYPE: DNA
<213> ORGANISM: Artificial sequence
<220> FEATURE:
<223> OTHER INFORMATION: primer

<400> SEQUENCE: 39
ctttcggcta aagagcgag atgcagataa aaaaattaaa ggcaattatt ctccg             55

<210> SEQ ID NO 40
<211> LENGTH: 879
<212> TYPE: DNA
<213> ORGANISM: Escherichia coli
<220> FEATURE:

<221> NAME/KEY: CDS
<222> LOCATION: (1)..(876)

<400> SEQUENCE: 40

```
atg ttc acg gga agt att gtc gcg att gtt act ccg atg gat gaa aaa      48
Met Phe Thr Gly Ser Ile Val Ala Ile Val Thr Pro Met Asp Glu Lys
1               5                   10                  15 ggt aat gtc tgt cgg gct agc ttg aaa aaa ctg att gat tat cat gtc      96
Gly Asn Val Cys Arg Ala Ser Leu Lys Lys Leu Ile Asp Tyr His Val
            20                  25                  30 gcc agc ggt act tcg gcg atc gtt tct gtt ggc acc act ggc gag tcc     144
Ala Ser Gly Thr Ser Ala Ile Val Ser Val Gly Thr Thr Gly Glu Ser
        35                  40                  45 gct acc tta aat cat gac gaa cat gct gat gtg gtg atg atg acg ctg     192
Ala Thr Leu Asn His Asp Glu His Ala Asp Val Val Met Met Thr Leu
    50                  55                  60 gat ctg gct gat ggg cgc att ccg gta att gcc ggg acc ggc gct aac     240
Asp Leu Ala Asp Gly Arg Ile Pro Val Ile Ala Gly Thr Gly Ala Asn
65                  70                  75                  80 gct act gcg gaa gcc att agc ctg acg cag cgc ttc aat gac agt ggt     288
Ala Thr Ala Glu Ala Ile Ser Leu Thr Gln Arg Phe Asn Asp Ser Gly
                85                  90                  95 atc gtc ggc tgc ctg acg gta acc cct tac tac aat cgt ccg tcg caa     336
Ile Val Gly Cys Leu Thr Val Thr Pro Tyr Tyr Asn Arg Pro Ser Gln
            100                 105                 110 gaa ggt ttg tat cag cat ttc aaa gcc atc gct gag cat act gac ctg     384
Glu Gly Leu Tyr Gln His Phe Lys Ala Ile Ala Glu His Thr Asp Leu
        115                 120                 125 ccg caa att ctg tat aat gtg ccg tcc cgt act ggc tgc gat ctg ctc     432
Pro Gln Ile Leu Tyr Asn Val Pro Ser Arg Thr Gly Cys Asp Leu Leu
    130                 135                 140 ccg gaa acg gtg ggc cgt ctg gcg aaa gta aaa aat att atc gga atc     480
Pro Glu Thr Val Gly Arg Leu Ala Lys Val Lys Asn Ile Ile Gly Ile
145                 150                 155                 160 aaa gag gca aca ggg aac tta acg cgt gta aac cag atc aaa gag ctg     528
Lys Glu Ala Thr Gly Asn Leu Thr Arg Val Asn Gln Ile Lys Glu Leu
                165                 170                 175 gtt tca gat gat ttt gtt ctg ctg agc ggc gat gat gcg agc gcg ctg     576
Val Ser Asp Asp Phe Val Leu Leu Ser Gly Asp Asp Ala Ser Ala Leu
            180                 185                 190 gac ttc atg caa ttg ggc ggt cat ggg gtt att tcc gtt acg gct aac     624
Asp Phe Met Gln Leu Gly Gly His Gly Val Ile Ser Val Thr Ala Asn
        195                 200                 205 gtc gca gcg cgt gat atg gcc cag atg tgc aaa ctg gca gca gaa ggg     672
Val Ala Ala Arg Asp Met Ala Gln Met Cys Lys Leu Ala Ala Glu Gly
    210                 215                 220 cat ttt gcc gag gca cgc gtt att aat cag cgt ctg atg cca tta cac     720
His Phe Ala Glu Ala Arg Val Ile Asn Gln Arg Leu Met Pro Leu His
225                 230                 235                 240 aac aaa cta ttt gtc gaa ccc aat cca atc ccg gtg aaa tgg gca tgt     768
Asn Lys Leu Phe Val Glu Pro Asn Pro Ile Pro Val Lys Trp Ala Cys
                245                 250                 255 aag gaa ctg ggt ctt gtg gcg acc gat acg ctg cgc ctg cca atg aca     816
Lys Glu Leu Gly Leu Val Ala Thr Asp Thr Leu Arg Leu Pro Met Thr
            260                 265                 270 cca atc acc gac agt ggt cgt gag acg gtc aga gcg gcg ctt aag cat     864
Pro Ile Thr Asp Ser Gly Arg Glu Thr Val Arg Ala Ala Leu Lys His
        275                 280                 285 gcc ggt ttg ctg taa                                                  879
Ala Gly Leu Leu
    290
```

<210> SEQ ID NO 41
<211> LENGTH: 292
<212> TYPE: PRT
<213> ORGANISM: Escherichia coli

<400> SEQUENCE: 41

Met Phe Thr Gly Ser Ile Val Ala Ile Val Thr Pro Met Asp Glu Lys
1               5                   10                  15

Gly Asn Val Cys Arg Ala Ser Leu Lys Lys Leu Ile Asp Tyr His Val
                20                  25                  30

Ala Ser Gly Thr Ser Ala Ile Val Ser Val Gly Thr Thr Gly Glu Ser
            35                  40                  45

Ala Thr Leu Asn His Asp Glu His Ala Asp Val Val Met Met Thr Leu
    50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Ala Asn
        195                 200                 205

Val Ala Ala Arg Asp Met Ala Gln Met Cys Lys Leu Ala Ala Glu Gly
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
    290

<210> SEQ ID NO 42
<211> LENGTH: 822
<212> TYPE: DNA
<213> ORGANISM: Escherichia coli
<220> FEATURE:
<221> NAME/KEY: CDS
<222> LOCATION: (1)..(822)

<400> SEQUENCE: 42 atg cat gat gca aac atc cgc gtt gcc atc gcg gga gcc ggg ggg cgt    48
Met His Asp Ala Asn Ile Arg Val Ala Ile Ala Gly Ala Gly Gly Arg
1               5                   10                  15

```
atg ggc cgc cag ttg att cag gcg gcg ctg gca tta gag ggc gtg cag       96
Met Gly Arg Gln Leu Ile Gln Ala Ala Leu Ala Leu Glu Gly Val Gln
         20                  25                  30 ttg ggc gct gcg ctg gag cgt gaa gga tct tct tta ctg ggc agc gac      144
Leu Gly Ala Ala Leu Glu Arg Glu Gly Ser Ser Leu Leu Gly Ser Asp
             35                  40                  45 gcc ggt gag ctg gcc gga gcc ggg aaa aca ggc gtt acc gtg caa agc      192
Ala Gly Glu Leu Ala Gly Ala Gly Lys Thr Gly Val Thr Val Gln Ser
 50                  55                  60 agc ctc gat gcg gta aaa gat gat ttt gat gtg ttt atc gat ttt acc      240
Ser Leu Asp Ala Val Lys Asp Asp Phe Asp Val Phe Ile Asp Phe Thr
 65                  70                  75                  80 cgt ccg gaa ggt acg ctg aac cat ctc gct ttt tgt cgc cag cat ggc      288
Arg Pro Glu Gly Thr Leu Asn His Leu Ala Phe Cys Arg Gln His Gly
                 85                  90                  95 aaa ggg atg gtg atc ggc act acg ggg ttt gac gaa gcc ggt aaa caa      336
Lys Gly Met Val Ile Gly Thr Thr Gly Phe Asp Glu Ala Gly Lys Gln
            100                 105                 110 gca att cgt gac gcc gct gcc gat att gcg att gtc ttt gct gcc aat      384
Ala Ile Arg Asp Ala Ala Ala Asp Ile Ala Ile Val Phe Ala Ala Asn
        115                 120                 125 ttt agc gtt ggc gtt aac gtc atg ctt aag ctg ctg gag aaa gca gcc      432
Phe Ser Val Gly Val Asn Val Met Leu Lys Leu Leu Glu Lys Ala Ala
    130                 135                 140 aaa gtg atg ggt gac tac acc gat atc gaa att att gaa gca cat cat      480
Lys Val Met Gly Asp Tyr Thr Asp Ile Glu Ile Ile Glu Ala His His
145                 150                 155                 160 aga cat aaa gtt gat gcg ccg tca ggc acc gca ctg gca atg gga gag      528
Arg His Lys Val Asp Ala Pro Ser Gly Thr Ala Leu Ala Met Gly Glu
                165                 170                 175 gcg atc gcc cac gcc ctt gat aaa gat ctg aaa gat tgc gcg gtc tac      576
Ala Ile Ala His Ala Leu Asp Lys Asp Leu Lys Asp Cys Ala Val Tyr
            180                 185                 190 agt cgt gaa ggc cac acc ggt gaa cgt gtg cct ggc acc att ggt ttt      624
Ser Arg Glu Gly His Thr Gly Glu Arg Val Pro Gly Thr Ile Gly Phe
        195                 200                 205 gcc acc gtg cgt gca ggt gac atc gtt ggt gaa cat acc gcg atg ttt      672
Ala Thr Val Arg Ala Gly Asp Ile Val Gly Glu His Thr Ala Met Phe
    210                 215                 220 gcc gat att ggc gag cgt ctg gag atc acc cat aag gcg tcc agc cgt      720
Ala Asp Ile Gly Glu Arg Leu Glu Ile Thr His Lys Ala Ser Ser Arg
225                 230                 235                 240 atg aca ttt gct aac ggc gcg gta aga tcg gct ttg tgg ttg agt ggt      768
Met Thr Phe Ala Asn Gly Ala Val Arg Ser Ala Leu Trp Leu Ser Gly
                245                 250                 255 aag gaa agc ggt ctt ttt gat atg cga gat gta ctt gat ctc aat aat      816
Lys Glu Ser Gly Leu Phe Asp Met Arg Asp Val Leu Asp Leu Asn Asn
            260                 265                 270 ttg taa                                                              822
Leu

<210> SEQ ID NO 43
<211> LENGTH: 273
<212> TYPE: PRT
<213> ORGANISM: Escherichia coli

<400> SEQUENCE: 43

Met His Asp Ala Asn Ile Arg Val Ala Ile Ala Gly Ala Gly Gly Arg
1               5                   10                  15

Met Gly Arg Gln Leu Ile Gln Ala Ala Leu Ala Leu Glu Gly Val Gln
```

```
                20                  25                  30
Leu Gly Ala Ala Leu Glu Arg Glu Gly Ser Ser Leu Leu Gly Ser Asp
            35                  40                  45

Ala Gly Glu Leu Ala Gly Ala Gly Lys Thr Gly Val Thr Val Gln Ser
        50                  55                  60

Ser Leu Asp Ala Val Lys Asp Phe Asp Val Phe Ile Asp Phe Thr
65                  70                  75                  80

Arg Pro Glu Gly Thr Leu Asn His Leu Ala Phe Cys Arg Gln His Gly
                85                  90                  95

Lys Gly Met Val Ile Gly Thr Thr Gly Phe Asp Glu Ala Gly Lys Gln
            100                 105                 110

Ala Ile Arg Asp Ala Ala Asp Ile Ala Ile Val Phe Ala Ala Asn
        115                 120                 125

Phe Ser Val Gly Val Asn Val Met Leu Lys Leu Leu Glu Lys Ala Ala
        130                 135                 140

Lys Val Met Gly Asp Tyr Thr Asp Ile Glu Ile Ile Glu Ala His His
145                 150                 155                 160

Arg His Lys Val Asp Ala Pro Ser Gly Thr Ala Leu Ala Met Gly Glu
                165                 170                 175

Ala Ile Ala His Ala Leu Asp Lys Asp Leu Lys Asp Cys Ala Val Tyr
            180                 185                 190

Ser Arg Glu Gly His Thr Gly Glu Arg Val Pro Gly Thr Ile Gly Phe
        195                 200                 205

Ala Thr Val Arg Ala Gly Asp Ile Val Gly Glu His Thr Ala Met Phe
        210                 215                 220

Ala Asp Ile Gly Glu Arg Leu Glu Ile Thr His Lys Ala Ser Ser Arg
225                 230                 235                 240

Met Thr Phe Ala Asn Gly Ala Val Arg Ser Ala Leu Trp Leu Ser Gly
                245                 250                 255

Lys Glu Ser Gly Leu Phe Asp Met Arg Asp Val Leu Asp Leu Asn Asn
            260                 265                 270

Leu

<210> SEQ ID NO 44
<211> LENGTH: 1104
<212> TYPE: DNA
<213> ORGANISM: Escherichia coli
<220> FEATURE:
<221> NAME/KEY: CDS
<222> LOCATION: (1)..(1104)

<400> SEQUENCE: 44 atg aaa aat gtt ggt ttt atc ggc tgg cgc ggt atg gtc ggc tcc gtt      48
Met Lys Asn Val Gly Phe Ile Gly Trp Arg Gly Met Val Gly Ser Val
1               5                   10                  15 ctc atg caa cgc atg gtt gaa gag cgc gac ttc gac gcc att cgc cct      96
Leu Met Gln Arg Met Val Glu Glu Arg Asp Phe Asp Ala Ile Arg Pro
            20                  25                  30 gtc ttc ttt tct act tct cag ctt ggc cag gct gcg ccg tct ttt ggc     144
Val Phe Phe Ser Thr Ser Gln Leu Gly Gln Ala Ala Pro Ser Phe Gly
        35                  40                  45 gga acc act ggc aca ctt cag gat gcc ttt gat ctg gag gcg cta aag     192
Gly Thr Thr Gly Thr Leu Gln Asp Ala Phe Asp Leu Glu Ala Leu Lys
    50                  55                  60 gcc ctc gat atc att gtg acc tgt cag ggc ggc gat tat acc aac gaa     240
Ala Leu Asp Ile Ile Val Thr Cys Gln Gly Gly Asp Tyr Thr Asn Glu
65                  70                  75                  80
```

```
atc tat cca aag ctt cgt gaa agc gga tgg caa ggt tac tgg att gac        288
Ile Tyr Pro Lys Leu Arg Glu Ser Gly Trp Gln Gly Tyr Trp Ile Asp
             85                  90                  95 gca gca tcg tct ctg cgc atg aaa gat gac gcc atc atc att ctt gac        336
Ala Ala Ser Ser Leu Arg Met Lys Asp Asp Ala Ile Ile Ile Leu Asp
        100                 105                 110 ccc gtc aat cag gac gtc att acc gac gga tta aat aat ggc atc agg        384
Pro Val Asn Gln Asp Val Ile Thr Asp Gly Leu Asn Asn Gly Ile Arg
            115                 120                 125 act ttt gtt ggc ggt aac tgt acc gta agc ctg atg ttg atg tcg ttg        432
Thr Phe Val Gly Gly Asn Cys Thr Val Ser Leu Met Leu Met Ser Leu
130                 135                 140 ggt ggt tta ttc gcc aat gat ctt gtt gat tgg gtg tcc gtt gca acc        480
Gly Gly Leu Phe Ala Asn Asp Leu Val Asp Trp Val Ser Val Ala Thr
145                 150                 155                 160 tac cag gcc gct tcc ggc ggt ggt gcg cga cat atg cgt gag tta tta        528
Tyr Gln Ala Ala Ser Gly Gly Gly Ala Arg His Met Arg Glu Leu Leu
                165                 170                 175 acc cag atg ggc cat ctg tat ggc cat gtg gca gat gaa ctc gcg acc        576
Thr Gln Met Gly His Leu Tyr Gly His Val Ala Asp Glu Leu Ala Thr
            180                 185                 190 ccg tcc tct gct att ctc gat atc gaa cgc aaa gtc aca acc tta acc        624
Pro Ser Ser Ala Ile Leu Asp Ile Glu Arg Lys Val Thr Thr Leu Thr
        195                 200                 205 cgt agc ggt gag ctg ccg gtg gat aac ttt ggc gtg ccg ctg gcg ggt        672
Arg Ser Gly Glu Leu Pro Val Asp Asn Phe Gly Val Pro Leu Ala Gly
    210                 215                 220 agc ctg att ccg tgg atc gac aaa cag ctc gat aac ggt cag agc cgc        720
Ser Leu Ile Pro Trp Ile Asp Lys Gln Leu Asp Asn Gly Gln Ser Arg
225                 230                 235                 240 gaa gag tgg aaa ggg cag gcg gaa acc aac aag atc ctc aac aca tct        768
Glu Glu Trp Lys Gly Gln Ala Glu Thr Asn Lys Ile Leu Asn Thr Ser
                245                 250                 255 tcc gta att ccg gta gat ggt tta tgt gtg cgt gtc ggg gca ttg cgc        816
Ser Val Ile Pro Val Asp Gly Leu Cys Val Arg Val Gly Ala Leu Arg
            260                 265                 270 tgc cac agc cag gca ttc act att aaa ttg aaa aaa gat gtg tct att        864
Cys His Ser Gln Ala Phe Thr Ile Lys Leu Lys Lys Asp Val Ser Ile
        275                 280                 285 ccg acc gtg gaa gaa ctg ctg gct gcg cac aat ccg tgg gcg aaa gtc        912
Pro Thr Val Glu Glu Leu Leu Ala Ala His Asn Pro Trp Ala Lys Val
    290                 295                 300 gtt ccg aac gat cgg gaa atc act atg cgt gag cta acc cca gct gcc        960
Val Pro Asn Asp Arg Glu Ile Thr Met Arg Glu Leu Thr Pro Ala Ala
305                 310                 315                 320 gtt acc ggc acg ctg acc acg ccg gta ggc cgc ctg cgt aag ctg aat       1008
Val Thr Gly Thr Leu Thr Thr Pro Val Gly Arg Leu Arg Lys Leu Asn
                325                 330                 335 atg gga cca gag ttc ctg tca gcc ttt acc gtg ggc gac cag ctg ctg       1056
Met Gly Pro Glu Phe Leu Ser Ala Phe Thr Val Gly Asp Gln Leu Leu
            340                 345                 350 tgg ggg gcc gcg gag ccg ctg cgt cgg atg ctt cgt caa ctg gcg taa       1104
Trp Gly Ala Ala Glu Pro Leu Arg Arg Met Leu Arg Gln Leu Ala
        355                 360                 365

<210> SEQ ID NO 45
<211> LENGTH: 367
<212> TYPE: PRT
<213> ORGANISM: Escherichia coli

<400> SEQUENCE: 45
```

| | | | | | | | | | | | |
|---|---|---|---|---|---|---|---|---|---|---|---|
| Met | Lys | Asn | Val | Gly | Phe | Ile | Gly | Trp | Arg | Gly | Met | Val | Gly | Ser | Val |
| 1 | | | | 5 | | | | | 10 | | | | | 15 | |
| Leu | Met | Gln | Arg | Met | Val | Glu | Glu | Arg | Asp | Phe | Asp | Ala | Ile | Arg | Pro |
| | | | 20 | | | | | 25 | | | | | 30 | | |
| Val | Phe | Phe | Ser | Thr | Ser | Gln | Leu | Gly | Gln | Ala | Ala | Pro | Ser | Phe | Gly |
| | | | 35 | | | | | 40 | | | | | 45 | | |
| Gly | Thr | Thr | Gly | Thr | Leu | Gln | Asp | Ala | Phe | Asp | Leu | Glu | Ala | Leu | Lys |
| | | | 50 | | | | | 55 | | | | | 60 | | |
| Ala | Leu | Asp | Ile | Ile | Val | Thr | Cys | Gln | Gly | Gly | Asp | Tyr | Thr | Asn | Glu |
| 65 | | | | | 70 | | | | | 75 | | | | | 80 |
| Ile | Tyr | Pro | Lys | Leu | Arg | Glu | Ser | Gly | Trp | Gln | Gly | Tyr | Trp | Ile | Asp |
| | | | | 85 | | | | | 90 | | | | | 95 | |
| Ala | Ala | Ser | Ser | Leu | Arg | Met | Lys | Asp | Asp | Ala | Ile | Ile | Ile | Leu | Asp |
| | | | 100 | | | | | 105 | | | | | 110 | | |
| Pro | Val | Asn | Gln | Asp | Val | Ile | Thr | Asp | Gly | Leu | Asn | Asn | Gly | Ile | Arg |
| | | | 115 | | | | | 120 | | | | | 125 | | |
| Thr | Phe | Val | Gly | Gly | Asn | Cys | Thr | Val | Ser | Leu | Met | Leu | Met | Ser | Leu |
| | | 130 | | | | | 135 | | | | | 140 | | | |
| Gly | Gly | Leu | Phe | Ala | Asn | Asp | Leu | Val | Asp | Trp | Val | Ser | Val | Ala | Thr |
| 145 | | | | | 150 | | | | | 155 | | | | | 160 |
| Tyr | Gln | Ala | Ala | Ser | Gly | Gly | Ala | Arg | His | Met | Arg | Glu | Leu | Leu |
| | | | | 165 | | | | | 170 | | | | | 175 | |
| Thr | Gln | Met | Gly | His | Leu | Tyr | Gly | His | Val | Ala | Asp | Glu | Leu | Ala | Thr |
| | | | 180 | | | | | 185 | | | | | 190 | | |
| Pro | Ser | Ser | Ala | Ile | Leu | Asp | Ile | Glu | Arg | Lys | Val | Thr | Thr | Leu | Thr |
| | | 195 | | | | | 200 | | | | | 205 | | | |
| Arg | Ser | Gly | Glu | Leu | Pro | Val | Asp | Asn | Phe | Gly | Val | Pro | Leu | Ala | Gly |
| 210 | | | | | 215 | | | | | 220 | | | | | |
| Ser | Leu | Ile | Pro | Trp | Ile | Asp | Lys | Gln | Leu | Asp | Asn | Gly | Gln | Ser | Arg |
| 225 | | | | | 230 | | | | | 235 | | | | | 240 |
| Glu | Glu | Trp | Lys | Gly | Gln | Ala | Glu | Thr | Asn | Lys | Ile | Leu | Asn | Thr | Ser |
| | | | | 245 | | | | | 250 | | | | | 255 | |
| Ser | Val | Ile | Pro | Val | Asp | Gly | Leu | Cys | Val | Arg | Val | Gly | Ala | Leu | Arg |
| | | | 260 | | | | | 265 | | | | | 270 | | |
| Cys | His | Ser | Gln | Ala | Phe | Thr | Ile | Lys | Leu | Lys | Lys | Asp | Val | Ser | Ile |
| | | 275 | | | | | 280 | | | | | 285 | | | |
| Pro | Thr | Val | Glu | Glu | Leu | Leu | Ala | Ala | His | Asn | Pro | Trp | Ala | Lys | Val |
| | 290 | | | | | 295 | | | | | 300 | | | | |
| Val | Pro | Asn | Asp | Arg | Glu | Ile | Thr | Met | Arg | Glu | Leu | Thr | Pro | Ala | Ala |
| 305 | | | | | 310 | | | | | 315 | | | | | 320 |
| Val | Thr | Gly | Thr | Leu | Thr | Thr | Pro | Val | Gly | Arg | Leu | Arg | Lys | Leu | Asn |
| | | | | 325 | | | | | 330 | | | | | 335 | |
| Met | Gly | Pro | Glu | Phe | Leu | Ser | Ala | Phe | Thr | Val | Gly | Asp | Gln | Leu | Leu |
| | | | 340 | | | | | 345 | | | | | 350 | | |
| Trp | Gly | Ala | Ala | Glu | Pro | Leu | Arg | Arg | Met | Leu | Arg | Gln | Leu | Ala |
| | 355 | | | | | 360 | | | | | 365 | | | | |

<210> SEQ ID NO 46
<211> LENGTH: 1350
<212> TYPE: DNA
<213> ORGANISM: Escherichia coli
<220> FEATURE:
<221> NAME/KEY: CDS
<222> LOCATION: (1)..(1350)

<400> SEQUENCE: 46

```
atg tct gaa att gtt gtc tcc aaa ttt ggc ggt acc agc gta gct gat    48
Met Ser Glu Ile Val Val Ser Lys Phe Gly Gly Thr Ser Val Ala Asp
1               5                   10                  15 ttt gac gcc atg aac cgc agc gct gat att gtg ctt tct gat gcc aac    96
Phe Asp Ala Met Asn Arg Ser Ala Asp Ile Val Leu Ser Asp Ala Asn
                20                  25                  30 gtg cgt tta gtt gtc ctc tcg gct tct gct ggt atc act aat ctg ctg   144
Val Arg Leu Val Val Leu Ser Ala Ser Ala Gly Ile Thr Asn Leu Leu
            35                  40                  45 gtc gct tta gct gaa gga ctg gaa cct ggc gag cga ttc gaa aaa ctc   192
Val Ala Leu Ala Glu Gly Leu Glu Pro Gly Glu Arg Phe Glu Lys Leu
        50                  55                  60 gac gct atc cgc aac atc cag ttt gcc att ctg gaa cgt ctg cgt tac   240
Asp Ala Ile Arg Asn Ile Gln Phe Ala Ile Leu Glu Arg Leu Arg Tyr
65                  70                  75                  80 ccg aac gtt atc cgt gaa gag att gaa cgt ctg ctg gag aac att act   288
Pro Asn Val Ile Arg Glu Glu Ile Glu Arg Leu Leu Glu Asn Ile Thr
                85                  90                  95 gtt ctg gca gaa gcg gcg ctg gca acg tct ccg gcg ctg aca gat       336
Val Leu Ala Glu Ala Ala Leu Ala Thr Ser Pro Ala Leu Thr Asp
            100                 105                 110 gag ctg gtc agc cac ggc gag ctg atg tcg acc ctg ctg ttt gtt gag   384
Glu Leu Val Ser His Gly Glu Leu Met Ser Thr Leu Leu Phe Val Glu
        115                 120                 125 atc ctg cgc gaa cgc gat gtt cag gca cag tgg ttt gat gta cgt aaa   432
Ile Leu Arg Glu Arg Asp Val Gln Ala Gln Trp Phe Asp Val Arg Lys
    130                 135                 140 gtg atg cgt acc aac gac cga ttt ggt cgt gca gag cca gat ata gcc   480
Val Met Arg Thr Asn Asp Arg Phe Gly Arg Ala Glu Pro Asp Ile Ala
145                 150                 155                 160 gcg ctg gcg gaa ctg gcc gcg ctg cag ctg ctc cca cgt ctc aat gaa   528
Ala Leu Ala Glu Leu Ala Ala Leu Gln Leu Leu Pro Arg Leu Asn Glu
                165                 170                 175 ggc tta gtg atc acc cag gga ttt atc ggt agc gaa aat aaa ggt cgt   576
Gly Leu Val Ile Thr Gln Gly Phe Ile Gly Ser Glu Asn Lys Gly Arg
            180                 185                 190 aca acg acg ctt ggc cgt gga ggc agc gat tat acg gca gcc ttg ctg   624
Thr Thr Thr Leu Gly Arg Gly Gly Ser Asp Tyr Thr Ala Ala Leu Leu
        195                 200                 205 gcg gag gct tta cac gca tct cgt gtt gat atc tgg acc gac gtc ccg   672
Ala Glu Ala Leu His Ala Ser Arg Val Asp Ile Trp Thr Asp Val Pro
    210                 215                 220 ggc atc tac acc acc gat cca cgc gta gtt tcc gca gca aaa cgc att   720
Gly Ile Tyr Thr Thr Asp Pro Arg Val Val Ser Ala Ala Lys Arg Ile
225                 230                 235                 240 gat gaa atc gcg ttt gcc gaa gcg gca gag atg gca act ttt ggt gca   768
Asp Glu Ile Ala Phe Ala Glu Ala Ala Glu Met Ala Thr Phe Gly Ala
                245                 250                 255 aaa gta ctg cat ccg gca acg ttg cta ccc gca gta cgc agc gat atc   816
Lys Val Leu His Pro Ala Thr Leu Leu Pro Ala Val Arg Ser Asp Ile
            260                 265                 270 ccg gtc ttt gtc ggc tcc agc aaa gac cca cgc gca ggt ggt acg ctg   864
Pro Val Phe Val Gly Ser Ser Lys Asp Pro Arg Ala Gly Gly Thr Leu
        275                 280                 285 gtg tgc aat aaa act gaa aat ccg ccg ctg ttc cgc gct ctg gcg ctt   912
Val Cys Asn Lys Thr Glu Asn Pro Pro Leu Phe Arg Ala Leu Ala Leu
    290                 295                 300 cgt cgc aat cag act ctg ctc act ttg cac agc ctg aat atg ctg cat   960
Arg Arg Asn Gln Thr Leu Leu Thr Leu His Ser Leu Asn Met Leu His
305                 310                 315                 320
```

```
tct cgc ggt ttc ctc gcg gaa gtt ttc ggc atc ctc gcg cgg cat aat    1008
Ser Arg Gly Phe Leu Ala Glu Val Phe Gly Ile Leu Ala Arg His Asn
            325                 330                 335 att tcg gta gac tta atc acc acg tca gaa gtg agc gtg gca tta acc    1056
Ile Ser Val Asp Leu Ile Thr Thr Ser Glu Val Ser Val Ala Leu Thr
        340                 345                 350 ctt gat acc acc ggt tca acc tcc act ggc gat acg ttg ctg acg caa    1104
Leu Asp Thr Thr Gly Ser Thr Ser Thr Gly Asp Thr Leu Leu Thr Gln
    355                 360                 365 tct ctg ctg atg gag ctt tcc gca ctg tgt cgg gtg gag gtg gaa gaa    1152
Ser Leu Leu Met Glu Leu Ser Ala Leu Cys Arg Val Glu Val Glu Glu
370                 375                 380 ggt ctg gcg ctg gtc gcg ttg att ggc aat gac ctg tca aaa gcc tgc    1200
Gly Leu Ala Leu Val Ala Leu Ile Gly Asn Asp Leu Ser Lys Ala Cys
385                 390                 395                 400 ggc gtt ggc aaa gag gta ttc ggc gta ctg gaa ccg ttc aac att cgc    1248
Gly Val Gly Lys Glu Val Phe Gly Val Leu Glu Pro Phe Asn Ile Arg
                405                 410                 415 atg att tgt tat ggc gca tcc agc cat aac ctg tgc ttc ctg gtg ccc    1296
Met Ile Cys Tyr Gly Ala Ser Ser His Asn Leu Cys Phe Leu Val Pro
            420                 425                 430 ggc gaa gat gcc gag cag gtg gtg caa aaa ctg cat agt aat ttg ttt    1344
Gly Glu Asp Ala Glu Gln Val Val Gln Lys Leu His Ser Asn Leu Phe
        435                 440                 445 gag taa                                                            1350
Glu

<210> SEQ ID NO 47
<211> LENGTH: 449
<212> TYPE: PRT
<213> ORGANISM: Escherichia coli

<400> SEQUENCE: 47

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
```

```
                195                 200                 205
Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Glu Met Ala Thr Phe Gly Ala
                245                 250                 255

Lys Val Leu His Pro Ala Thr Leu Leu Pro Ala Val Arg Ser Asp Ile
                260                 265                 270

Pro Val Phe Val Gly Ser Ser Lys Asp Pro Arg Ala Gly Gly Thr Leu
                275                 280                 285

Val Cys Asn Lys Thr Glu Asn Pro Pro Leu Phe Arg Ala Leu Ala Leu
    290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
                355                 360                 365

Ser Leu Leu Met Glu Leu Ser Ala Leu Cys Arg Val Glu Val Glu Glu
    370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
                435                 440                 445

Glu

<210> SEQ ID NO 48
<211> LENGTH: 1245
<212> TYPE: DNA
<213> ORGANISM: Methylophilus methylotrophus
<220> FEATURE:
<221> NAME/KEY: CDS
<222> LOCATION: (1)..(1245)

<400> SEQUENCE: 48 gtg acc gct ttt tca atc caa caa ggc cta cta cat gcc gag aat gta      48
Val Thr Ala Phe Ser Ile Gln Gln Gly Leu Leu His Ala Glu Asn Val
1               5                   10                  15 gcc ctg cgt gac att gca caa acg cat caa acg ccc act tac gtc tat      96
Ala Leu Arg Asp Ile Ala Gln Thr His Gln Thr Pro Thr Tyr Val Tyr
                20                  25                  30 tca cgt gcc gcc ttg acg act gct ttc gag cgt ttt cag gca ggc ctg     144
Ser Arg Ala Ala Leu Thr Thr Ala Phe Glu Arg Phe Gln Ala Gly Leu
            35                  40                  45 act gga cat gac cat ttg atc tgc ttt gct gtc aaa gcc aac cca agc     192
Thr Gly His Asp His Leu Ile Cys Phe Ala Val Lys Ala Asn Pro Ser
        50                  55                  60 ctg gcc att ctc aac ctg ttt gcg cga atg gga gcg ggc ttt gat att     240
Leu Ala Ile Leu Asn Leu Phe Ala Arg Met Gly Ala Gly Phe Asp Ile
65                  70                  75                  80
```

```
gtg tcc ggt ggt gag ctg gca cgc gtc ttg gcc gca ggt ggc gac ccg     288
Val Ser Gly Gly Glu Leu Ala Arg Val Leu Ala Ala Gly Gly Asp Pro
            85                  90                  95 aaa aaa gtg gtg ttt tct ggt gtg ggc aaa tcc cat gcg gaa atc aaa     336
Lys Lys Val Val Phe Ser Gly Val Gly Lys Ser His Ala Glu Ile Lys
        100                 105                 110 gcc gcg ctt gaa gcg ggc att ctt tgc ttc aac gtg gaa tca gtg aat     384
Ala Ala Leu Glu Ala Gly Ile Leu Cys Phe Asn Val Glu Ser Val Asn
    115                 120                 125 gag cta gac cgc atc cag cag gtg gcg gcc agc ctg ggc aaa aaa gcg     432
Glu Leu Asp Arg Ile Gln Gln Val Ala Ala Ser Leu Gly Lys Lys Ala
130                 135                 140 cct att tcc ctg cgc gtg aac ccc aat gtg gat gcc aaa acc cat ccc     480
Pro Ile Ser Leu Arg Val Asn Pro Asn Val Asp Ala Lys Thr His Pro
145                 150                 155                 160 tat att tcc acc ggc ctc aaa aac aat aaa ttt ggt gtg gca ttt gaa     528
Tyr Ile Ser Thr Gly Leu Lys Asn Asn Lys Phe Gly Val Ala Phe Glu
            165                 170                 175 gat gcc ttg ggc ctc tat gaa aaa gcg gcg caa ctg cca aac atc gag     576
Asp Ala Leu Gly Leu Tyr Glu Lys Ala Ala Gln Leu Pro Asn Ile Glu
        180                 185                 190 gta cac ggc gta gat tgc cat atc ggc tcg caa atc act gag ctg tca     624
Val His Gly Val Asp Cys His Ile Gly Ser Gln Ile Thr Glu Leu Ser
    195                 200                 205 cct ttc ctc gat gcc ttg gat aaa gta ttg ggc ctg gta gat gca ttg     672
Pro Phe Leu Asp Ala Leu Asp Lys Val Leu Gly Leu Val Asp Ala Leu
210                 215                 220 gcc gcc aaa ggc att cat atc cag cat ata gac gtt ggc ggc ggt gtc     720
Ala Ala Lys Gly Ile His Ile Gln His Ile Asp Val Gly Gly Gly Val
225                 230                 235                 240 ggt att act tac agc gac gaa acg cca cca gac ttt gca gcc tac act     768
Gly Ile Thr Tyr Ser Asp Glu Thr Pro Pro Asp Phe Ala Ala Tyr Thr
            245                 250                 255 gca gcg att ctt aaa aag ctg gca ggc agg aat gta aaa gtg ttg ttt     816
Ala Ala Ile Leu Lys Lys Leu Ala Gly Arg Asn Val Lys Val Leu Phe
        260                 265                 270 gag ccc ggc cgt gcc ctg gtg ggt aac gcc ggt gtg ctg ctg acc aag     864
Glu Pro Gly Arg Ala Leu Val Gly Asn Ala Gly Val Leu Leu Thr Lys
    275                 280                 285 gtc gaa tac ctg aaa cct ggc gaa acc aaa aac ttt gcg att gtc gat     912
Val Glu Tyr Leu Lys Pro Gly Glu Thr Lys Asn Phe Ala Ile Val Asp
290                 295                 300 gcc gcc atg aac gac ctc atg cgc ccg gct ttg tat gat gct ttc cac     960
Ala Ala Met Asn Asp Leu Met Arg Pro Ala Leu Tyr Asp Ala Phe His
305                 310                 315                 320 aac att acg acc att gcc act tct gca gcc ccc gca caa atc tat gag    1008
Asn Ile Thr Thr Ile Ala Thr Ser Ala Ala Pro Ala Gln Ile Tyr Glu
            325                 330                 335 atc gtt ggc ccg gtt tgc gag agt ggt gac ttt tta ggc cat gac cgt    1056
Ile Val Gly Pro Val Cys Glu Ser Gly Asp Phe Leu Gly His Asp Arg
        340                 345                 350 aca ctt gcg atc gaa gaa ggt gat tac ctg gcg att cac tcc gca ggc    1104
Thr Leu Ala Ile Glu Glu Gly Asp Tyr Leu Ala Ile His Ser Ala Gly
    355                 360                 365 gct tat ggc atg agc atg gcc agc aac tac aac acg cgc gcc cgt gcc    1152
Ala Tyr Gly Met Ser Met Ala Ser Asn Tyr Asn Thr Arg Ala Arg Ala
370                 375                 380 gca gag gta ttg gtt gat ggt gac cag gtg cat gtg atc cgt gaa cgt    1200
Ala Glu Val Leu Val Asp Gly Asp Gln Val His Val Ile Arg Glu Arg
385                 390                 395                 400
```

```
gaa caa att gcc gac ctg ttt aaa ctg gag cgt acg ctg cca taa         1245
Glu Gln Ile Ala Asp Leu Phe Lys Leu Glu Arg Thr Leu Pro
            405                 410
```

<210> SEQ ID NO 49
<211> LENGTH: 414
<212> TYPE: PRT
<213> ORGANISM: Methylophilus methylotrophus

<400> SEQUENCE: 49

```
Val Thr Ala Phe Ser Ile Gln Gln Gly Leu Leu His Ala Glu Asn Val
 1               5                  10                  15

Ala Leu Arg Asp Ile Ala Gln Thr His Gln Thr Pro Thr Tyr Val Tyr
            20                  25                  30

Ser Arg Ala Ala Leu Thr Thr Ala Phe Glu Arg Phe Gln Ala Gly Leu
        35                  40                  45

Thr Gly His Asp His Leu Ile Cys Phe Ala Val Lys Ala Asn Pro Ser
    50                  55                  60

Leu Ala Ile Leu Asn Leu Phe Ala Arg Met Gly Ala Gly Phe Asp Ile
65                  70                  75                  80

Val Ser Gly Gly Glu Leu Ala Arg Val Leu Ala Ala Gly Gly Asp Pro
                85                  90                  95

Lys Lys Val Val Phe Ser Gly Val Gly Lys Ser His Ala Glu Ile Lys
            100                 105                 110

Ala Ala Leu Glu Ala Gly Ile Leu Cys Phe Asn Val Glu Ser Val Asn
        115                 120                 125

Glu Leu Asp Arg Ile Gln Gln Val Ala Ala Ser Leu Gly Lys Lys Ala
    130                 135                 140

Pro Ile Ser Leu Arg Val Asn Pro Asn Val Asp Ala Lys Thr His Pro
145                 150                 155                 160

Tyr Ile Ser Thr Gly Leu Lys Asn Asn Lys Phe Gly Val Ala Phe Glu
                165                 170                 175

Asp Ala Leu Gly Leu Tyr Glu Lys Ala Ala Gln Leu Pro Asn Ile Glu
            180                 185                 190

Val His Gly Val Asp Cys His Ile Gly Ser Gln Ile Thr Glu Leu Ser
        195                 200                 205

Pro Phe Leu Asp Ala Leu Asp Lys Val Leu Gly Leu Val Asp Ala Leu
    210                 215                 220

Ala Ala Lys Gly Ile His Ile Gln His Ile Asp Val Gly Gly Gly Val
225                 230                 235                 240

Gly Ile Thr Tyr Ser Asp Glu Thr Pro Pro Asp Phe Ala Ala Tyr Thr
                245                 250                 255

Ala Ala Ile Leu Lys Lys Leu Ala Gly Arg Asn Val Lys Val Leu Phe
            260                 265                 270

Glu Pro Gly Arg Ala Leu Val Gly Asn Ala Gly Val Leu Leu Thr Lys
        275                 280                 285

Val Glu Tyr Leu Lys Pro Gly Glu Thr Lys Asn Phe Ala Ile Val Asp
    290                 295                 300

Ala Ala Met Asn Asp Leu Met Arg Pro Ala Leu Tyr Asp Ala Phe His
305                 310                 315                 320

Asn Ile Thr Thr Ile Ala Thr Ser Ala Ala Pro Ala Gln Ile Tyr Glu
                325                 330                 335

Ile Val Gly Pro Val Cys Glu Ser Gly Asp Phe Leu Gly His Asp Arg
            340                 345                 350

Thr Leu Ala Ile Glu Glu Gly Asp Tyr Leu Ala Ile His Ser Ala Gly
        355                 360                 365
```

```
Ala Tyr Gly Met Ser Met Ala Ser Asn Tyr Asn Thr Arg Ala Arg Ala
    370                 375                 380

Ala Glu Val Leu Val Asp Gly Asp Gln Val His Val Ile Arg Glu Arg
385                 390                 395                 400

Glu Gln Ile Ala Asp Leu Phe Lys Leu Glu Arg Thr Leu Pro
            405                 410

<210> SEQ ID NO 50
<211> LENGTH: 712
<212> TYPE: DNA
<213> ORGANISM: Brevibacterium lactofermentum
<220> FEATURE:
<221> NAME/KEY: CDS
<222> LOCATION: (1)..(375)

<400> SEQUENCE: 50 atg gtg atc atg gaa atc ttc att aca ggt ctg ctt ttg ggg gcc agt         48
Met Val Ile Met Glu Ile Phe Ile Thr Gly Leu Leu Leu Gly Ala Ser
1               5                   10                  15 ctt ttg ctg tcc atc gga ccg cag aat gta ctg gtg att aaa caa gga         96
Leu Leu Leu Ser Ile Gly Pro Gln Asn Val Leu Val Ile Lys Gln Gly
                20                  25                  30 att aag cgc gaa gga ctc att gcg gtt ctc ctc gtg tgt tta att tct        144
Ile Lys Arg Glu Gly Leu Ile Ala Val Leu Leu Val Cys Leu Ile Ser
            35                  40                  45 gac gtc ttt ttg ttc atc gcc ggc acc ttg ggc gtt gat ctt ttg tcc        192
Asp Val Phe Leu Phe Ile Ala Gly Thr Leu Gly Val Asp Leu Leu Ser
    50                  55                  60 aat gcc gcg ccg atc gtg ctc gat att atg cgc tgg ggt ggc atc gct        240
Asn Ala Ala Pro Ile Val Leu Asp Ile Met Arg Trp Gly Gly Ile Ala
65                  70                  75                  80 tac ctg tta tgg ttt gcc gtc atg gca gcg aaa gac gcc atg aca aac        288
Tyr Leu Leu Trp Phe Ala Val Met Ala Ala Lys Asp Ala Met Thr Asn
                85                  90                  95 aag gtg gaa gcg cca cag atc att gaa gaa aca gaa cca acc gtg ccc        336
Lys Val Glu Ala Pro Gln Ile Ile Glu Glu Thr Glu Pro Thr Val Pro
                100                 105                 110 gat gac acg cct ttg ggc gtg ttc ggc ggt ggc cac tga cacgcgcaac         385
Asp Asp Thr Pro Leu Gly Val Phe Gly Gly Gly His
            115                 120 cgggtgcggg tggaggtgag cgtcgataag cagcgggttt gggtgaagcc catgttgatg      445
gcaatcgtgc tgacctggtt gaacccgaat gcgtatttgg acgcgtttgt gtttatcggc      505
ggcgtcggcg cgcaatacgg cgacaccgga cggtggattt tcgccgctgg cgcgttcgcg      565
gcaagcctga tctggttccc gctggtgggt ttcggcgcag cagcattgtc acgcccgctg      625
tccagcccca aggtgtggcg ctggatcaac gtcgtcgtgg cagttgtgat gaccgcattg      685
gccatcaaac tgatgttgat gggttag                                          712

<210> SEQ ID NO 51
<211> LENGTH: 124
<212> TYPE: PRT
<213> ORGANISM: Brevibacterium lactofermentum

<400> SEQUENCE: 51

Met Val Ile Met Glu Ile Phe Ile Thr Gly Leu Leu Leu Gly Ala Ser
1               5                   10                  15

Leu Leu Leu Ser Ile Gly Pro Gln Asn Val Leu Val Ile Lys Gln Gly
                20                  25                  30

Ile Lys Arg Glu Gly Leu Ile Ala Val Leu Leu Val Cys Leu Ile Ser
```

```
                    35                  40                  45
Asp Val Phe Leu Phe Ile Ala Gly Thr Leu Gly Val Asp Leu Leu Ser
 50                  55                  60

Asn Ala Ala Pro Ile Val Leu Asp Ile Met Arg Trp Gly Gly Ile Ala
 65                  70                  75                  80

Tyr Leu Leu Trp Phe Ala Val Met Ala Ala Lys Asp Ala Met Thr Asn
                 85                  90                  95

Lys Val Glu Ala Pro Gln Ile Ile Glu Thr Glu Pro Thr Val Pro
            100                 105                 110

Asp Asp Thr Pro Leu Gly Val Phe Gly Gly Gly His
        115                 120

<210> SEQ ID NO 52
<211> LENGTH: 963
<212> TYPE: DNA
<213> ORGANISM: Brevibacterium lactofermentum
<220> FEATURE:
<221> NAME/KEY: CDS
<222> LOCATION: (1)..(963)

<400> SEQUENCE: 52 atg acc aac atc cgc gta gct atc gtg ggc tac gga aac ctg gga cgc      48
Met Thr Asn Ile Arg Val Ala Ile Val Gly Tyr Gly Asn Leu Gly Arg
 1               5                  10                  15 agc gtc gaa aag ctt att gcc aag cag ccc gac atg gac ctt gta gga      96
Ser Val Glu Lys Leu Ile Ala Lys Gln Pro Asp Met Asp Leu Val Gly
                20                  25                  30 atc ttc tcg cgc cgg gcc acc ctc gac aca aag acg cca gtc ttt gat     144
Ile Phe Ser Arg Arg Ala Thr Leu Asp Thr Lys Thr Pro Val Phe Asp
            35                  40                  45 gtc gcc gac gtg gac aag cac gcc gac gac gtg gac gtg ctg ttc ctg     192
Val Ala Asp Val Asp Lys His Ala Asp Asp Val Asp Val Leu Phe Leu
 50                  55                  60 tgc atg ggc tcc gcc acc gac atc cct gag cag gca cca aag ttc gcg     240
Cys Met Gly Ser Ala Thr Asp Ile Pro Glu Gln Ala Pro Lys Phe Ala
 65                  70                  75                  80 cag ttc gcc tgc acc gta gac acc tac gac aac cac cgc gac atc cca     288
Gln Phe Ala Cys Thr Val Asp Thr Tyr Asp Asn His Arg Asp Ile Pro
                 85                  90                  95 cgc cac cgc cag gtc atg aac gaa gcc gcc acc gca gcc ggc aac gtt     336
Arg His Arg Gln Val Met Asn Glu Ala Ala Thr Ala Ala Gly Asn Val
            100                 105                 110 gca ctg gtc tct acc ggc tgg gat cca gga atg ttc tcc atc aac cgc     384
Ala Leu Val Ser Thr Gly Trp Asp Pro Gly Met Phe Ser Ile Asn Arg
        115                 120                 125 gtc tac gca gcg gca gtc tta gcc gag cac cag cag cac acc ttc tgg     432
Val Tyr Ala Ala Ala Val Leu Ala Glu His Gln Gln His Thr Phe Trp
    130                 135                 140 ggc cca ggt ttg tca cag ggc cac tcc gat gct ttg cga cgc atc cct     480
Gly Pro Gly Leu Ser Gln Gly His Ser Asp Ala Leu Arg Arg Ile Pro
145                 150                 155                 160 ggc gtt caa aag gca gtc cag tac acc ctc cca tcc gaa gac gcc ctg     528
Gly Val Gln Lys Ala Val Gln Tyr Thr Leu Pro Ser Glu Asp Ala Leu
                165                 170                 175 gaa aag gcc cgc cgc ggc gaa gcc ggc gac ctt acc gga aag caa acc     576
Glu Lys Ala Arg Arg Gly Glu Ala Gly Asp Leu Thr Gly Lys Gln Thr
            180                 185                 190 cac aag cgc caa tgc ttc gtg gtt gcc gac gcg gcc gat cac gag cgc     624
His Lys Arg Gln Cys Phe Val Val Ala Asp Ala Ala Asp His Glu Arg
        195                 200                 205
```

```
atc gaa aac gac atc cgc acc atg cct gat tac ttc gtt ggc tac gaa    672
Ile Glu Asn Asp Ile Arg Thr Met Pro Asp Tyr Phe Val Gly Tyr Glu
    210                 215                 220 gtc gaa gtc aac ttc atc gac gaa gca acc ttc gac tcc gag cac acc    720
Val Glu Val Asn Phe Ile Asp Glu Ala Thr Phe Asp Ser Glu His Thr
225                 230                 235                 240 ggc atg cca cac ggt ggc cac gtg att acc acc ggc gac acc ggt ggc    768
Gly Met Pro His Gly Gly His Val Ile Thr Thr Gly Asp Thr Gly Gly
                245                 250                 255 ttc aac cac acc gtg gaa tac atc ctc aag ctg gac cga aac cca gat    816
Phe Asn His Thr Val Glu Tyr Ile Leu Lys Leu Asp Arg Asn Pro Asp
            260                 265                 270 ttc acc gct tcc tca cag atc gct ttc ggt cgc gca gct cac cgc atg    864
Phe Thr Ala Ser Ser Gln Ile Ala Phe Gly Arg Ala Ala His Arg Met
        275                 280                 285 aag cag cag ggc caa agc gga gct ttc acc gtc ctc gaa gtt gct cca    912
Lys Gln Gln Gly Gln Ser Gly Ala Phe Thr Val Leu Glu Val Ala Pro
    290                 295                 300 tac ctg ctc tcc cca gag aac ttg gac gat ctg atc gca cgc gac gtc    960
Tyr Leu Leu Ser Pro Glu Asn Leu Asp Asp Leu Ile Ala Arg Asp Val
305                 310                 315                 320 taa                                                                 963

<210> SEQ ID NO 53
<211> LENGTH: 320
<212> TYPE: PRT
<213> ORGANISM: Brevibacterium lactofermentum

<400> SEQUENCE: 53

Met Thr Asn Ile Arg Val Ala Ile Val Gly Tyr Gly Asn Leu Gly Arg
1               5                   10                  15

Ser Val Glu Lys Leu Ile Ala Lys Gln Pro Asp Met Asp Leu Val Gly
            20                  25                  30

Ile Phe Ser Arg Arg Ala Thr Leu Asp Thr Lys Thr Pro Val Phe Asp
        35                  40                  45

Val Ala Asp Val Asp Lys His Ala Asp Val Asp Val Leu Phe Leu
    50                  55                  60

Cys Met Gly Ser Ala Thr Asp Ile Pro Glu Gln Ala Pro Lys Phe Ala
65                  70                  75                  80

Gln Phe Ala Cys Thr Val Asp Thr Tyr Asp Asn His Arg Asp Ile Pro
                85                  90                  95

Arg His Arg Gln Val Met Asn Glu Ala Ala Thr Ala Ala Gly Asn Val
            100                 105                 110

Ala Leu Val Ser Thr Gly Trp Asp Pro Gly Met Phe Ser Ile Asn Arg
        115                 120                 125

Val Tyr Ala Ala Ala Val Leu Ala Glu His Gln Gln His Thr Phe Trp
    130                 135                 140

Gly Pro Gly Leu Ser Gln Gly His Ser Asp Ala Leu Arg Arg Ile Pro
145                 150                 155                 160

Gly Val Gln Lys Ala Val Gln Tyr Thr Leu Pro Ser Glu Asp Ala Leu
                165                 170                 175

Glu Lys Ala Arg Arg Gly Glu Ala Gly Asp Leu Thr Gly Lys Gln Thr
            180                 185                 190

His Lys Arg Gln Cys Phe Val Val Ala Asp Ala Ala Asp His Glu Arg
        195                 200                 205

Ile Glu Asn Asp Ile Arg Thr Met Pro Asp Tyr Phe Val Gly Tyr Glu
    210                 215                 220
```

-continued

```
Val Glu Val Asn Phe Ile Asp Glu Ala Thr Phe Asp Ser Glu His Thr
225                 230                 235                 240

Gly Met Pro His Gly His Val Ile Thr Thr Gly Asp Thr Gly Gly
                245                 250                 255

Phe Asn His Thr Val Glu Tyr Ile Leu Lys Leu Asp Arg Asn Pro Asp
                260                 265                 270

Phe Thr Ala Ser Ser Gln Ile Ala Phe Gly Arg Ala Ala His Arg Met
            275                 280                 285

Lys Gln Gln Gly Gln Ser Gly Ala Phe Thr Val Leu Glu Val Ala Pro
290                 295                 300

Tyr Leu Leu Ser Pro Glu Asn Leu Asp Asp Leu Ile Ala Arg Asp Val
305                 310                 315                 320
```

<210> SEQ ID NO 54
<211> LENGTH: 711
<212> TYPE: DNA
<213> ORGANISM: Brevibacterium lactofermentum
<220> FEATURE:
<221> NAME/KEY: CDS
<222> LOCATION: (1)..(711)

<400> SEQUENCE: 54

```
atg gtg atc atg gaa atc ttc att aca ggt ctg ctt ttg ggg gcc agt      48
Met Val Ile Met Glu Ile Phe Ile Thr Gly Leu Leu Leu Gly Ala Ser
1               5                   10                  15 ctt tta ctg tcc atc gga ccg cag aat gta ctg gtg att aaa caa gga      96
Leu Leu Leu Ser Ile Gly Pro Gln Asn Val Leu Val Ile Lys Gln Gly
                20                  25                  30 att aag cgc gaa gga ctc att gcg gtt ctt ctc gtg tgt tta att tct     144
Ile Lys Arg Glu Gly Leu Ile Ala Val Leu Leu Val Cys Leu Ile Ser
            35                  40                  45 gac gtc ttt ttg ttc atc gcc ggc acc ttg ggc gtt gat ctt ttg tcc     192
Asp Val Phe Leu Phe Ile Ala Gly Thr Leu Gly Val Asp Leu Leu Ser
        50                  55                  60 aat gcc gcg ccg atc gtg ctc gat att atg cgc tgg ggt ggc atc gct     240
Asn Ala Ala Pro Ile Val Leu Asp Ile Met Arg Trp Gly Gly Ile Ala
65                  70                  75                  80 tac ctg tta tgg ttt gcc gtc atg gca gcg aaa gac gcc atg aca aac     288
Tyr Leu Leu Trp Phe Ala Val Met Ala Ala Lys Asp Ala Met Thr Asn
                85                  90                  95 aag gtg gaa gcg cca cag atc att gaa gaa aca gaa cca acc gtg ccc     336
Lys Val Glu Ala Pro Gln Ile Ile Glu Glu Thr Glu Pro Thr Val Pro
                100                 105                 110 gat gac acg cct ttg ggc ggt tcg gcg gtg gcc act gac acg cgc aac     384
Asp Asp Thr Pro Leu Gly Gly Ser Ala Val Ala Thr Asp Thr Arg Asn
            115                 120                 125 cgg gtg cgg gtg gag gtg agc gtc gat aag cag cgg gtt tgg gta aag     432
Arg Val Arg Val Glu Val Ser Val Asp Lys Gln Arg Val Trp Val Lys
        130                 135                 140 ccc atg ttg atg gca atc gtg ctg acc tgg ttg aac ccg aat gcg tat     480
Pro Met Leu Met Ala Ile Val Leu Thr Trp Leu Asn Pro Asn Ala Tyr
145                 150                 155                 160 ttg gac gcg ttt gtg ttt atc ggc ggt gtc ggc gcg caa tac ggc gac     528
Leu Asp Ala Phe Val Phe Ile Gly Gly Val Gly Ala Gln Tyr Gly Asp
                165                 170                 175 acc gga cgg tgg att ttc gcc gct ggc gcg ttc gca gca agc ctg atc     576
Thr Gly Arg Trp Ile Phe Ala Ala Gly Ala Phe Ala Ala Ser Leu Ile
            180                 185                 190 tgg ttc ccg ctg gtg ggt ttc ggc gca gca gca ttg tca cgc ccg ctg     624
Trp Phe Pro Leu Val Gly Phe Gly Ala Ala Ala Leu Ser Arg Pro Leu
        195                 200                 205
```

```
tcc agc ccc aag gtg tgg cgc tgg atc aac gtc gtc gtg gca gtt gtg      672
Ser Ser Pro Lys Val Trp Arg Trp Ile Asn Val Val Val Ala Val Val
    210                 215                 220 atg acc gca ttg gcc atc aaa ctg atg ttg atg ggt tag                  711
Met Thr Ala Leu Ala Ile Lys Leu Met Leu Met Gly
225                 230                 235
```

<210> SEQ ID NO 55
<211> LENGTH: 236
<212> TYPE: PRT
<213> ORGANISM: Brevibacterium lactofermentum

<400> SEQUENCE: 55

```
Met Val Ile Met Glu Ile Phe Ile Thr Gly Leu Leu Leu Gly Ala Ser
1               5                   10                  15

Leu Leu Leu Ser Ile Gly Pro Gln Asn Val Leu Val Ile Lys Gln Gly
                20                  25                  30

Ile Lys Arg Glu Gly Leu Ile Ala Val Leu Leu Val Cys Leu Ile Ser
            35                  40                  45

Asp Val Phe Leu Phe Ile Ala Gly Thr Leu Gly Val Asp Leu Leu Ser
        50                  55                  60

Asn Ala Ala Pro Ile Val Leu Asp Ile Met Arg Trp Gly Gly Ile Ala
65                  70                  75                  80

Tyr Leu Leu Trp Phe Ala Val Met Ala Ala Lys Asp Ala Met Thr Asn
                85                  90                  95

Lys Val Glu Ala Pro Gln Ile Ile Glu Glu Thr Glu Pro Thr Val Pro
                100                 105                 110

Asp Asp Thr Pro Leu Gly Gly Ser Ala Val Ala Thr Asp Thr Arg Asn
            115                 120                 125

Arg Val Arg Val Glu Val Ser Val Asp Lys Gln Arg Val Trp Val Lys
        130                 135                 140

Pro Met Leu Met Ala Ile Val Leu Thr Trp Leu Asn Pro Asn Ala Tyr
145                 150                 155                 160

Leu Asp Ala Phe Val Phe Ile Gly Gly Val Gly Ala Gln Tyr Gly Asp
                165                 170                 175

Thr Gly Arg Trp Ile Phe Ala Ala Gly Ala Phe Ala Ala Ser Leu Ile
            180                 185                 190

Trp Phe Pro Leu Val Gly Phe Gly Ala Ala Ala Leu Ser Arg Pro Leu
        195                 200                 205

Ser Ser Pro Lys Val Trp Arg Trp Ile Asn Val Val Val Ala Val Val
210                 215                 220

Met Thr Ala Leu Ala Ile Lys Leu Met Leu Met Gly
225                 230                 235
```

<210> SEQ ID NO 56
<211> LENGTH: 761
<212> TYPE: DNA
<213> ORGANISM: Brevibacterium lactofermentum
<220> FEATURE:
<221> NAME/KEY: CDS
<222> LOCATION: (1)..(372)
<220> FEATURE:
<221> NAME/KEY: CDS
<222> LOCATION: (401)..(712)

<400> SEQUENCE: 56

```
atg gtg atc atg gaa atc ttc att aca ggt ctg ctt ttg ggg gcc agt       48
Met Val Ile Met Glu Ile Phe Ile Thr Gly Leu Leu Leu Gly Ala Ser
1               5                   10                  15
```

```
ctt ttg ctg tcc atc gga ccg cag aat gta ctg gta att aaa caa gga      96
Leu Leu Leu Ser Ile Gly Pro Gln Asn Val Leu Val Ile Lys Gln Gly
            20                  25                  30 att aag cgc gaa gga ctc att gcg gtt ctc ctc gtg tgt tta att tct     144
Ile Lys Arg Glu Gly Leu Ile Ala Val Leu Leu Val Cys Leu Ile Ser
        35                  40                  45 gac gtc ttt ttg ttc atc gcc ggc acc ttg ggc gtt gat ctt ttg tcc     192
Asp Val Phe Leu Phe Ile Ala Gly Thr Leu Gly Val Asp Leu Leu Ser
    50                  55                  60 aat gcc gcg ccg atc gtg ctc gat att atg cgc tgg ggt ggc atc gct     240
Asn Ala Ala Pro Ile Val Leu Asp Ile Met Arg Trp Gly Gly Ile Ala
65                  70                  75                  80 tac ctg tta tgg ttt gcc gtc atg gca gcg aaa gac gcc atg aca aac     288
Tyr Leu Leu Trp Phe Ala Val Met Ala Ala Lys Asp Ala Met Thr Asn
                85                  90                  95 aag gtg gaa gcg cca cag atc att gaa gaa aca gaa cca acc gtg ccc     336
Lys Val Glu Ala Pro Gln Ile Ile Glu Glu Thr Glu Pro Thr Val Pro
            100                 105                 110 gat gac acg cct ttg ggc gtg ttc ggc ggt ggc cac tgactagcta          382
Asp Asp Thr Pro Leu Gly Val Phe Gly Gly Gly His
        115                 120 aaccgggtgc gggtggag gtg agc gtc gat aag cag cgg gtt tgg gtg aag     433
                    Val Ser Val Asp Lys Gln Arg Val Trp Val Lys
                                125                 130                 135 ccc atg ttg atg gca atc gtg ctg acc tgg ttg aac ccg aat gcg tat     481
Pro Met Leu Met Ala Ile Val Leu Thr Trp Leu Asn Pro Asn Ala Tyr
                140                 145                 150 ttg gac gcg ttt gtg ttt atc ggc ggc gtc ggc gcg caa tac ggc gac     529
Leu Asp Ala Phe Val Phe Ile Gly Gly Val Gly Ala Gln Tyr Gly Asp
            155                 160                 165 acc gga cgg tgg att ttc gcc gct ggc gcg ttc gcg gca agc ctg atc     577
Thr Gly Arg Trp Ile Phe Ala Ala Gly Ala Phe Ala Ala Ser Leu Ile
        170                 175                 180 tgg ttc ccg ctg gtg ggt ttc ggc gca gca ttg tca cgc ccg ctg         625
Trp Phe Pro Leu Val Gly Phe Gly Ala Ala Leu Ser Arg Pro Leu
    185                 190                 195 tcc agc ccc aag gtg tgg cgc tgg atc aac gtc gtc gtg gca gtt gtg     673
Ser Ser Pro Lys Val Trp Arg Trp Ile Asn Val Val Val Ala Val Val
200                 205                 210                 215 atg acc gca ttg gcc atc aaa ctg atg ttg atg ggt tag ttttcgcggg      722
Met Thr Ala Leu Ala Ile Lys Leu Met Leu Met Gly
                220                 225 ttttggagct cttctagcag aagagcatac atctggaag                           761

<210> SEQ ID NO 57
<211> LENGTH: 124
<212> TYPE: PRT
<213> ORGANISM: Brevibacterium lactofermentum

<400> SEQUENCE: 57

Met Val Ile Met Glu Ile Phe Ile Thr Gly Leu Leu Leu Gly Ala Ser
1               5                   10                  15

Leu Leu Leu Ser Ile Gly Pro Gln Asn Val Leu Val Ile Lys Gln Gly
            20                  25                  30

Ile Lys Arg Glu Gly Leu Ile Ala Val Leu Leu Val Cys Leu Ile Ser
        35                  40                  45

Asp Val Phe Leu Phe Ile Ala Gly Thr Leu Gly Val Asp Leu Leu Ser
    50                  55                  60

Asn Ala Ala Pro Ile Val Leu Asp Ile Met Arg Trp Gly Gly Ile Ala
65                  70                  75                  80
```

```
Tyr Leu Leu Trp Phe Ala Val Met Ala Ala Lys Asp Ala Met Thr Asn
                85                  90                  95

Lys Val Glu Ala Pro Gln Ile Ile Glu Glu Thr Pro Thr Val Pro
            100                 105                 110

Asp Asp Thr Pro Leu Gly Val Phe Gly Gly Gly His
            115                 120

<210> SEQ ID NO 58
<211> LENGTH: 828
<212> TYPE: DNA
<213> ORGANISM: Methylophilus methylotrophus
<220> FEATURE:
<221> NAME/KEY: CDS
<222> LOCATION: (1)..(825)

<400> SEQUENCE: 58
```

| | | | | | | | | | | | | | | | | |
|---|---|---|---|---|---|---|---|---|---|---|---|---|---|---|---|---|
| gtg | aat | aat | aat | atc | tct | tac | agt | ttt | gaa | ttc | ttc | ccg | ccc | aag | acg | 48 |
| Val | Asn | Asn | Asn | Ile | Ser | Tyr | Ser | Phe | Glu | Phe | Phe | Pro | Pro | Lys | Thr | |
| 1 | | | | 5 | | | | | 10 | | | | | 15 | | |
| gta | gaa | ggc | atg | gcc | aat | ctg | cgc | aat | gtg | cgc | aat | gag | ctg | gcg | gca | 96 |
| Val | Glu | Gly | Met | Ala | Asn | Leu | Arg | Asn | Val | Arg | Asn | Glu | Leu | Ala | Ala | |
| | | | 20 | | | | | 25 | | | | | 30 | | | |
| ttt | tca | ccc | gaa | ttt | ttc | tcg | gtc | act | ttt | ggc | gca | ggt | ggc | tcc | acg | 144 |
| Phe | Ser | Pro | Glu | Phe | Phe | Ser | Val | Thr | Phe | Gly | Ala | Gly | Gly | Ser | Thr | |
| | | 35 | | | | | 40 | | | | | 45 | | | | |
| cgt | gac | cgt | acc | atg | gaa | agc | gtg | ctg | gaa | atc | cag | gcg | gaa | ggc | cat | 192 |
| Arg | Asp | Arg | Thr | Met | Glu | Ser | Val | Leu | Glu | Ile | Gln | Ala | Glu | Gly | His | |
| | 50 | | | | | 55 | | | | | 60 | | | | | |
| ggg | gca | gca | cct | cat | att | tcc | tgt | att | tcc | tct | agt | aaa | gaa | gaa | att | 240 |
| Gly | Ala | Ala | Pro | His | Ile | Ser | Cys | Ile | Ser | Ser | Ser | Lys | Glu | Glu | Ile | |
| 65 | | | | | 70 | | | | | 75 | | | | | 80 | |
| cgt | gag | tta | tta | cag | gct | tat | caa | gcc | aaa | ggc | atc | aag | cga | ctg | gtc | 288 |
| Arg | Glu | Leu | Leu | Gln | Ala | Tyr | Gln | Ala | Lys | Gly | Ile | Lys | Arg | Leu | Val | |
| | | | | 85 | | | | | 90 | | | | | 95 | | |
| acc | ttg | cgc | ggc | gat | atc | cct | tca | ggc | gaa | gtg | agt | gct | ggc | gat | ttt | 336 |
| Thr | Leu | Arg | Gly | Asp | Ile | Pro | Ser | Gly | Glu | Val | Ser | Ala | Gly | Asp | Phe | |
| | | | 100 | | | | | 105 | | | | | 110 | | | |
| aaa | tat | gcc | aat | gag | ctg | gtg | agt | ttt | atc | cgt | gct | gaa | acc | ggt | gac | 384 |
| Lys | Tyr | Ala | Asn | Glu | Leu | Val | Ser | Phe | Ile | Arg | Ala | Glu | Thr | Gly | Asp | |
| | | 115 | | | | | 120 | | | | | 125 | | | | |
| tgg | ttt | cac | ctc | gaa | gtg | gcg | gct | tac | cct | gag | ttt | cat | ccg | gaa | gca | 432 |
| Trp | Phe | His | Leu | Glu | Val | Ala | Ala | Tyr | Pro | Glu | Phe | His | Pro | Glu | Ala | |
| | 130 | | | | | 135 | | | | | 140 | | | | | |
| ggt | tct | gca | caa | aaa | gac | ctg | gaa | aac | ttc | aaa | cgt | aaa | atc | gat | gcc | 480 |
| Gly | Ser | Ala | Gln | Lys | Asp | Leu | Glu | Asn | Phe | Lys | Arg | Lys | Ile | Asp | Ala | |
| 145 | | | | | 150 | | | | | 155 | | | | | 160 | |
| ggt | gcc | gat | tct | gcc | att | acg | cag | tac | ttt | tac | aat | atg | gat | gcg | tat | 528 |
| Gly | Ala | Asp | Ser | Ala | Ile | Thr | Gln | Tyr | Phe | Tyr | Asn | Met | Asp | Ala | Tyr | |
| | | | | 165 | | | | | 170 | | | | | 175 | | |
| ttc | cgt | ttt | gtg | gaa | gcg | gcg | caa | aaa | atg | ggt | gtt | aca | gcg | cct | atc | 576 |
| Phe | Arg | Phe | Val | Glu | Ala | Ala | Gln | Lys | Met | Gly | Val | Thr | Ala | Pro | Ile | |
| | | | 180 | | | | | 185 | | | | | 190 | | | |
| att | ccc | ggc | atc | atg | ccg | atc | tac | aat | tac | acg | cag | ctg | gcg | cgt | ttt | 624 |
| Ile | Pro | Gly | Ile | Met | Pro | Ile | Tyr | Asn | Tyr | Thr | Gln | Leu | Ala | Arg | Phe | |
| | | 195 | | | | | 200 | | | | | 205 | | | | |
| tcc | aat | gta | tgt | ggt | gca | gag | att | cca | cgc | tgg | ttg | cgt | tta | cgt | ctg | 672 |
| Ser | Asn | Val | Cys | Gly | Ala | Glu | Ile | Pro | Arg | Trp | Leu | Arg | Leu | Arg | Leu | |
| | 210 | | | | | 215 | | | | | 220 | | | | | |
| gaa | gct | tat | ggt | gat | gac | ttg | gct | tca | tta | cgt | gct | ttt | ggc | gtg | gat | 720 |
| Glu | Ala | Tyr | Gly | Asp | Asp | Leu | Ala | Ser | Leu | Arg | Ala | Phe | Gly | Val | Asp | |
| 225 | | | | | 230 | | | | | 235 | | | | | 240 | |

```
gta gtc acc gat att tgc gcc aag ctg att gcg tct ggc gtg gat aaa     768
Val Val Thr Asp Ile Cys Ala Lys Leu Ile Ala Ser Gly Val Asp Lys
                245                 250                 255 atg cat ttc tat acg ctg aac cag gct ggc att att ggc cag att atc     816
Met His Phe Tyr Thr Leu Asn Gln Ala Gly Ile Ile Gly Gln Ile Ile
            260                 265                 270 cgg caa ctg taa                                                     828
Arg Gln Leu
    275

<210> SEQ ID NO 59
<211> LENGTH: 275
<212> TYPE: PRT
<213> ORGANISM: Methylophilus methylotrophus

<400> SEQUENCE: 59

Val Asn Asn Asn Ile Ser Tyr Ser Phe Glu Phe Pro Pro Lys Thr
 1               5                  10                  15

Val Glu Gly Met Ala Asn Leu Arg Asn Val Arg Asn Glu Leu Ala Ala
            20                  25                  30

Phe Ser Pro Glu Phe Phe Ser Val Thr Phe Gly Ala Gly Gly Ser Thr
        35                  40                  45

Arg Asp Arg Thr Met Glu Ser Val Leu Glu Ile Gln Ala Glu Gly His
    50                  55                  60

Gly Ala Ala Pro His Ile Ser Cys Ile Ser Ser Lys Glu Ile
65                  70                  75                  80

Arg Glu Leu Leu Gln Ala Tyr Gln Ala Lys Gly Ile Lys Arg Leu Val
                85                  90                  95

Thr Leu Arg Gly Asp Ile Pro Ser Gly Glu Val Ser Ala Gly Asp Phe
            100                 105                 110

Lys Tyr Ala Asn Glu Leu Val Ser Phe Ile Arg Ala Glu Thr Gly Asp
        115                 120                 125

Trp Phe His Leu Glu Val Ala Ala Tyr Pro Gly Phe His Pro Glu Ala
    130                 135                 140

Gly Ser Ala Gln Lys Asp Leu Glu Asn Phe Lys Arg Lys Ile Asp Ala
145                 150                 155                 160

Gly Ala Asp Ser Ala Ile Thr Gln Tyr Phe Tyr Asn Met Asp Ala Tyr
                165                 170                 175

Phe Arg Phe Val Glu Ala Ala Gln Lys Met Gly Val Thr Ala Pro Ile
            180                 185                 190

Ile Pro Gly Ile Met Pro Ile Tyr Asn Tyr Thr Gln Leu Ala Arg Phe
        195                 200                 205

Ser Asn Val Cys Gly Ala Glu Ile Pro Arg Trp Leu Arg Leu Arg Leu
    210                 215                 220

Glu Ala Tyr Gly Asp Asp Leu Ala Ser Leu Arg Ala Phe Gly Val Asp
225                 230                 235                 240

Val Val Thr Asp Ile Cys Ala Lys Leu Ile Ala Ser Gly Val Asp Lys
                245                 250                 255

Met His Phe Tyr Thr Leu Asn Gln Ala Gly Ile Ile Gly Gln Ile Ile
            260                 265                 270

Arg Gln Leu
    275
```